United States Patent
Hess et al.

(10) Patent No.: US 9,364,519 B2
(45) Date of Patent: Jun. 14, 2016

(54) PHARMACEUTICAL COMPOSITION FOR USE IN THE TREATMENT OF A NEURODEGENERATIVE DISEASE

(75) Inventors: Sibylle Hess, Frankfurt am Main (DE); Christian Hoelscher, Northern Ireland (GB); Andrees Boehme, Paris (FR); Agnes Menut, Paris (FR); Laurent Pradier, Paris (FR); Veronique Taupin, Paris (FR)

(73) Assignees: SANOFI-AVENTIS DEUTSCHLAND GMBH, Frankfurt am Main (DE); UNIVERSITY OF ULSTER, Coleraine (GB)

( * ) Notice: Subject to any disclaimer, the term of this patent is extended or adjusted under 35 U.S.C. 154(b) by 0 days.

(21) Appl. No.: 13/602,913

(22) Filed: Sep. 4, 2012

(65) Prior Publication Data
US 2013/0116179 A1     May 9, 2013

Related U.S. Application Data

(60) Provisional application No. 61/530,146, filed on Sep. 1, 2011.

(30) Foreign Application Priority Data

Sep. 1, 2011  (EP) ..................................... 11179784

(51) Int. Cl.
*A61K 38/26* (2006.01)
*A61P 25/28* (2006.01)

(52) U.S. Cl.
CPC ....................... *A61K 38/26* (2013.01)

(58) Field of Classification Search
CPC ........ A61K 38/26; A61K 38/00; C07K 14/605
USPC ....................................................... 514/11.7
See application file for complete search history.

(56) References Cited

U.S. PATENT DOCUMENTS

| | | |
|---|---|---|
| 3,758,683 A | 9/1973 | Jackson |
| 3,868,358 A | 2/1975 | Jackson |
| 3,984,696 A | 10/1976 | Collica et al. |
| 4,153,689 A | 5/1979 | Hirai et al. |
| 4,258,134 A | 3/1981 | Yoshida et al. |
| 4,367,737 A | 1/1983 | Kozam et al. |
| 4,608,364 A | 8/1986 | Grau |
| 4,614,730 A | 9/1986 | Hansen et al. |
| 4,644,057 A | 2/1987 | Bicker et al. |
| 4,689,042 A | 8/1987 | Sarnoff et al. |
| 4,701,440 A | 10/1987 | Grau |
| 4,731,405 A | 3/1988 | Kirsch et al. |
| 4,783,441 A | 11/1988 | Thurow |
| 4,839,341 A | 6/1989 | Massey et al. |
| 4,863,902 A | 9/1989 | Amagase et al. |
| 4,885,164 A | 12/1989 | Thurow |
| 4,923,162 A | 5/1990 | Fleming et al. |
| 4,959,351 A | 9/1990 | Grau |
| 4,960,702 A | 10/1990 | Rice et al. |
| 4,994,439 A | 2/1991 | Longenecker et al. |
| 5,006,718 A | 4/1991 | Lenhart |
| 5,008,241 A | 4/1991 | Markussen et al. |
| 5,034,415 A | 7/1991 | Rubin |
| 5,070,186 A | 12/1991 | Joergensen |
| 5,101,013 A | 3/1992 | Dorschug et al. |
| 5,177,058 A | 1/1993 | Dorschug |
| 5,187,177 A | 2/1993 | Garzaran |
| 5,227,293 A | 7/1993 | Stengelin et al. |
| 5,253,785 A | 10/1993 | Haber et al. |
| 5,272,135 A | 12/1993 | Takruri |
| 5,358,708 A | 10/1994 | Patel |
| 5,358,857 A | 10/1994 | Stengelin et al. |
| 5,370,629 A | 12/1994 | Michel et al. |
| 5,397,771 A | 3/1995 | Bechgaard et al. |
| 5,407,609 A | 4/1995 | Tice et al. |
| 5,424,286 A | 6/1995 | Eng |
| 5,428,006 A | 6/1995 | Bechgaard et al. |
| 5,473,049 A | 12/1995 | Obermeier et al. |
| 5,474,978 A | 12/1995 | Bakaysa et al. |

(Continued)

FOREIGN PATENT DOCUMENTS

| | | |
|---|---|---|
| AU | 1986-62066 | 3/1987 |
| AU | 1987-75916 | 1/1988 |

(Continued)

OTHER PUBLICATIONS

Hölscher et al., "New roles for insulin-like hormones in neuronal signaling and protection: new hopes for novel treatments of Alzheimer's disease?" Neuro. Aging 31:1495-1502 (2008).*
Margolis, R. "Diagnosis of Huntington's Disease,"Clin. Chem. 49:1726-32 (2003).*
Broderick et al., "Guidelines for the Management of Spontaneous Intracerebral Hemorrhage in Adults," Circulation 116:e391-e413 (2007).*
Holscher et al., "New roles for insulin-like hormones in neuronal signaling and protection: new hopes for novel treatments of Alzheimer's disease?" Neuro. Aging 31:1495-1502 (2008).*
Abbas et al., "Impairment of synaptic plasticity and memory formation in GLP-1 receptor KO mice: Interaction between type 2 diabetes and Alzheimer's disease," Behav. Brain Res. 205:265-271 (2009).*

(Continued)

*Primary Examiner* — Julie Ha
*Assistant Examiner* — Kristina M Hellman
(74) *Attorney, Agent, or Firm* — McDonnell Boehnen Hulbert & Berghoff LLP

(57) ABSTRACT

The present application relates to a pharmaceutical composition for use in the prevention or/and treatment of a neurodegenerative disease, the composition comprising desPro$^{36}$Exendin-4(1-39)-Lys$_6$-NH$_2$ or/and a pharmaceutically acceptable salt thereof, and optionally a pharmaceutically acceptable carrier, adjuvant, or/and auxiliary substance. In addition, the present application relates to the use of the pharmaceutical composition for the treatment and prevention of a neurodegenerative disease.

4 Claims, 10 Drawing Sheets

(56) References Cited

U.S. PATENT DOCUMENTS

Figure 1:
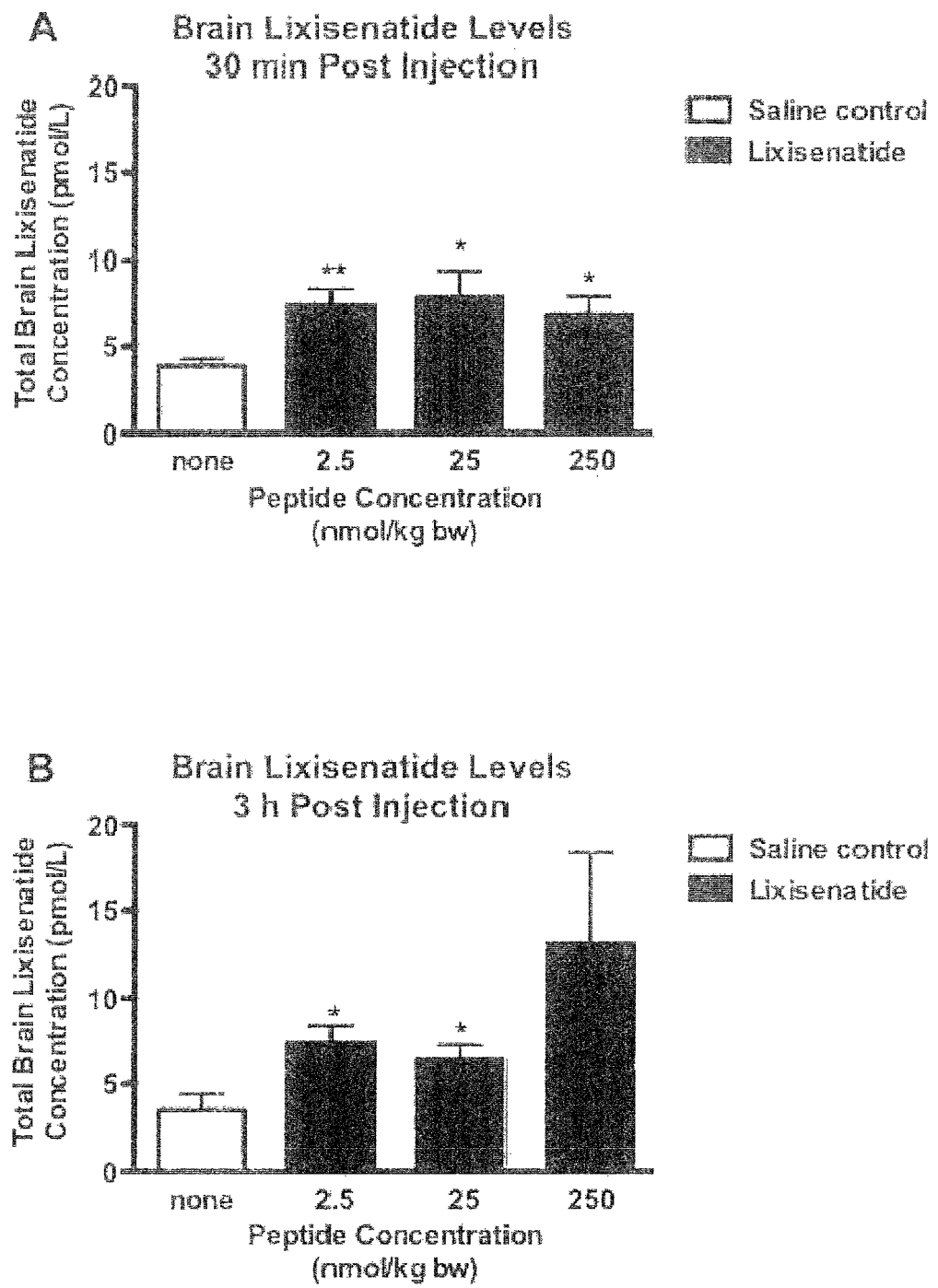

| | | |
|---|---|---|
| 5,478,323 A | 12/1995 | Westwood et al. |
| 5,496,924 A | 3/1996 | Habermann et al. |
| 5,506,203 A | 4/1996 | Backstrom et al. |
| 5,509,905 A | 4/1996 | Michel et al. |
| 5,514,646 A | 5/1996 | Chance et al. |
| 5,524,286 A | 6/1996 | Chiesa et al. |
| 5,535,488 A | 7/1996 | Hoffmann |
| 5,545,618 A | 8/1996 | Buckley et al. |
| 5,547,929 A | 8/1996 | Anderson, Jr. et al. |
| 5,559,094 A | 9/1996 | Brems et al. |
| 5,595,756 A | 1/1997 | Bally et al. |
| 5,597,796 A | 1/1997 | Brange |
| 5,614,219 A | 3/1997 | Wunderlich et al. |
| 5,614,492 A | 3/1997 | Habener |
| 5,631,224 A | 5/1997 | Efendic et al. |
| 5,654,008 A | 8/1997 | Herbert et al. |
| 5,656,722 A | 8/1997 | Dorschug |
| 5,663,291 A | 9/1997 | Obermeier et al. |
| 5,670,360 A | 9/1997 | Thorens |
| 5,693,608 A | 12/1997 | Bechgaard et al. |
| 5,700,662 A | 12/1997 | Chance et al. |
| 5,707,641 A | 1/1998 | Gertner et al. |
| 5,783,556 A | 7/1998 | Clark et al. |
| 5,824,638 A | 10/1998 | Burnside et al. |
| 5,846,747 A | 12/1998 | Thorens et al. |
| 5,846,937 A | 12/1998 | Drucker |
| 5,948,751 A | 9/1999 | Kimer et al. |
| 5,952,297 A | 9/1999 | DeFelippis et al. |
| 5,981,964 A | 11/1999 | McAuley et al. |
| 5,985,309 A | 11/1999 | Edwards et al. |
| 6,006,753 A | 12/1999 | Efendic |
| 6,034,054 A | 3/2000 | DeFelippis et al. |
| 6,043,214 A | 3/2000 | Jensen et al. |
| 6,051,551 A | 4/2000 | Hughes et al. |
| 6,051,689 A | 4/2000 | Thorens |
| 6,100,376 A | 8/2000 | Dorschug |
| 6,110,703 A | 8/2000 | Egei-Mitani et al. |
| 6,174,856 B1 | 1/2001 | Langballe et al. |
| 6,191,102 B1 | 2/2001 | DiMarchi et al. |
| 6,211,144 B1 | 4/2001 | Havelund |
| 6,227,819 B1 | 5/2001 | Gettel et al. |
| 6,248,363 B1 | 6/2001 | Patel et al. |
| 6,267,981 B1 | 7/2001 | Okamoto et al. |
| 6,268,335 B1 | 7/2001 | Brader |
| 6,268,343 B1 | 7/2001 | Knudsen et al. |
| 6,271,241 B1 | 8/2001 | DeSimone et al. |
| 6,284,725 B1 | 9/2001 | Coolidge et al. |
| 6,309,663 B1 | 10/2001 | Patel et al. |
| 6,310,038 B1 | 10/2001 | Havelund |
| 6,329,336 B1 | 12/2001 | Briden et al. |
| 6,335,316 B1 | 1/2002 | Hughes et al. |
| 6,344,180 B1 | 2/2002 | Holst et al. |
| 6,358,924 B1 | 3/2002 | Hoffmann |
| 6,384,016 B1 | 5/2002 | Kaarsholm |
| 6,388,053 B1 | 5/2002 | Galloway et al. |
| 6,395,767 B2 | 5/2002 | Robl et al. |
| 6,410,508 B1 | 6/2002 | Isales et al. |
| 6,417,164 B1 | 7/2002 | Kolterman |
| 6,444,641 B1 | 9/2002 | Flora |
| 6,468,959 B1 | 10/2002 | Wunderlich et al. |
| 6,489,292 B1 | 12/2002 | Havelund et al. |
| 6,528,486 B1 | 3/2003 | Larsen et al. |
| 6,734,162 B2 | 5/2004 | Van Antwerp et al. |
| 6,767,887 B1 | 7/2004 | Hoffmann et al. |
| 6,818,738 B2 | 11/2004 | Havelund |
| 6,852,694 B2 | 2/2005 | Van Antwerp et al. |
| 6,875,589 B1 | 4/2005 | Dorschug et al. |
| 6,908,610 B1 | 6/2005 | Sato |
| 6,908,897 B2 | 6/2005 | Brandenburg et al. |
| 6,960,561 B2 | 11/2005 | Boderke |
| 6,969,702 B2 | 11/2005 | Bertilsson et al. |
| 7,022,674 B2 | 4/2006 | DeFelippis |
| 7,115,563 B2 | 10/2006 | Younis |
| 7,119,086 B2 | 10/2006 | Di Malta et al. |
| 7,192,919 B2 | 3/2007 | Tzannis et al. |
| 7,205,276 B2 | 4/2007 | Boderke |
| 7,205,277 B2 | 4/2007 | Boderke |
| 7,238,663 B2 | 7/2007 | DeFelippis et al. |
| 7,405,196 B2 | 7/2008 | Rosskamp et al. |
| 7,476,652 B2 | 1/2009 | Brunner-Schwarz et al. |
| 7,544,656 B2 | 6/2009 | Sabetsky |
| 7,544,657 B2 | 6/2009 | Ebbehoj et al. |
| 7,576,050 B2 | 8/2009 | Greig et al. |
| 7,713,930 B2 | 5/2010 | Brunner-Schwarz et al. |
| 7,803,763 B2 | 9/2010 | Thurow et al. |
| 7,807,242 B2 | 10/2010 | Soerensen et al. |
| 7,918,833 B2 | 4/2011 | Veasey et al. |
| 7,939,293 B2 | 5/2011 | Habermann et al. |
| 7,977,310 B2 | 7/2011 | Rosskamp et al. |
| 8,048,854 B2 | 11/2011 | Habermann et al. |
| 8,084,420 B2 | 12/2011 | Steiner et al. |
| 8,092,421 B2 | 1/2012 | Seiferlein et al. |
| 8,092,422 B2 | 1/2012 | Seiferlein et al. |
| 8,178,495 B2 | 5/2012 | Chilkoti |
| 8,574,214 B2 | 11/2013 | Kuhn et al. |
| 8,633,156 B2 | 1/2014 | Habermann et al. |
| 8,735,349 B2 | 5/2014 | Silvestre et al. |
| 2001/0012829 A1 | 8/2001 | Anderson et al. |
| 2001/0033868 A1 | 10/2001 | Rossling et al. |
| 2001/0039260 A1 | 11/2001 | Havelund |
| 2001/0047084 A1 | 11/2001 | Knudsen et al. |
| 2002/0107265 A1 | 8/2002 | Chen et al. |
| 2002/0132760 A1 | 9/2002 | Van Antwerp et al. |
| 2002/0177151 A1 | 11/2002 | Gimeno |
| 2002/0198140 A1 | 12/2002 | Havelund |
| 2003/0004096 A1 | 1/2003 | Boderke |
| 2003/0026872 A1 | 2/2003 | Dake et al. |
| 2003/0104983 A1 | 6/2003 | DeFelippis et al. |
| 2003/0170691 A1 | 9/2003 | Gimeno |
| 2004/0048783 A1 | 3/2004 | Brunner-Schwarz et al. |
| 2004/0092590 A1 | 5/2004 | Arteburn et al. |
| 2004/0097410 A1 | 5/2004 | Zheng et al. |
| 2004/0106547 A1 | 6/2004 | Larsen et al. |
| 2004/0186046 A1 | 9/2004 | Burgess et al. |
| 2004/0229774 A1 | 11/2004 | Rosskamp et al. |
| 2004/0235710 A1 | 11/2004 | DeFelippis et al. |
| 2005/0014679 A1 | 1/2005 | Beals et al. |
| 2005/0079996 A1 | 4/2005 | Horiguchi et al. |
| 2005/0106147 A1 | 5/2005 | Jordan et al. |
| 2005/0171009 A1 | 8/2005 | Brunner-Schwarz et al. |
| 2005/0209142 A1* | 9/2005 | Bertilsson et al. .............. 514/12 |
| 2006/0004049 A1 | 1/2006 | Yao et al. |
| 2006/0014678 A1 | 1/2006 | Cowley et al. |
| 2006/0019347 A1 | 1/2006 | Cho et al. |
| 2006/0057137 A1 | 3/2006 | Steiness |
| 2006/0073213 A1 | 4/2006 | Hotamisligil et al. |
| 2006/0093576 A1 | 5/2006 | Chen et al. |
| 2006/0194719 A1 | 8/2006 | Ebbehoj et al. |
| 2006/0239933 A1 | 10/2006 | Nilsson et al. |
| 2006/0287221 A1 | 12/2006 | Knudsen et al. |
| 2007/0027063 A1 | 2/2007 | Boss et al. |
| 2007/0111940 A1 | 5/2007 | Larsen et al. |
| 2007/0128193 A1 | 6/2007 | O'Neil et al. |
| 2007/0135338 A1 | 6/2007 | O'Neil et al. |
| 2007/0155653 A1 | 7/2007 | Boderke |
| 2007/0191271 A1 | 8/2007 | Mayhew et al. |
| 2007/0237827 A1 | 10/2007 | Sung et al. |
| 2008/0146490 A1 | 6/2008 | Joabsson et al. |
| 2008/0234200 A1 | 9/2008 | Quay et al. |
| 2008/0248999 A1 | 10/2008 | Steiner |
| 2008/0260840 A1 | 10/2008 | Alessi et al. |
| 2008/0267907 A1 | 10/2008 | Poulsen |
| 2009/0082255 A1 | 3/2009 | Brunner-Schwarz et al. |
| 2009/0088369 A1 | 4/2009 | Steiness |
| 2009/0099064 A1 | 4/2009 | Lougheed |
| 2009/0175840 A1 | 7/2009 | Kashyap et al. |
| 2009/0176692 A1 | 7/2009 | Habermann et al. |
| 2009/0180953 A1 | 7/2009 | Gotthardt et al. |
| 2009/0186819 A1 | 7/2009 | Carrier et al. |
| 2009/0208565 A1 | 8/2009 | Ebbehoj et al. |
| 2009/0214657 A1 | 8/2009 | Qazi |
| 2009/0304665 A1 | 12/2009 | Frost et al. |
| 2009/0312236 A1 | 12/2009 | Beals et al. |
| 2009/0324701 A1 | 12/2009 | Williams |

(56) References Cited

U.S. PATENT DOCUMENTS

| | | |
|---|---|---|
| 2010/0029558 A1 | 2/2010 | Bristow |
| 2010/0055049 A1 | 3/2010 | Kuo et al. |
| 2010/0057194 A1 | 3/2010 | Ryan |
| 2010/0069292 A1 | 3/2010 | Pohl et al. |
| 2010/0069293 A1 | 3/2010 | Bolotin et al. |
| 2010/0227816 A1 | 9/2010 | Flatt et al. |
| 2010/0279931 A1 | 11/2010 | Garibay et al. |
| 2010/0311112 A1 | 12/2010 | Rissom et al. |
| 2011/0020294 A1 | 1/2011 | Hammerman |
| 2011/0021423 A1 | 1/2011 | Olsen et al. |
| 2011/0077197 A1 | 3/2011 | Habermann et al. |
| 2011/0118178 A1 | 5/2011 | Silvestre et al. |
| 2011/0118180 A1 | 5/2011 | Silvestre et al. |
| 2011/0144008 A1 | 6/2011 | Larsen et al. |
| 2011/0152185 A1 | 6/2011 | Plum et al. |
| 2011/0173722 A1 | 7/2011 | Habermann et al. |
| 2011/0230402 A1 | 9/2011 | Johansen et al. |
| 2011/0236925 A1 | 9/2011 | Hazra et al. |
| 2011/0245165 A1 | 10/2011 | Larsen et al. |
| 2011/0281790 A1 | 11/2011 | Pohl et al. |
| 2011/0301081 A1 | 12/2011 | Becker et al. |
| 2012/0021978 A1 | 1/2012 | Werner et al. |
| 2012/0121611 A1 | 5/2012 | Lodie et al. |
| 2012/0122774 A1 | 5/2012 | Becker et al. |
| 2012/0183616 A1 | 7/2012 | Sprogoe et al. |
| 2012/0232002 A1 | 9/2012 | Schoettle et al. |
| 2012/0241356 A1 | 9/2012 | Pfenninger et al. |
| 2012/0252724 A1 | 10/2012 | Schoettle et al. |
| 2012/0277147 A1 | 11/2012 | Boka et al. |
| 2012/0283179 A1 | 11/2012 | Brunner-Schwarz et al. |
| 2012/0295846 A1 | 11/2012 | Hagendorg et al. |
| 2012/0316108 A1 | 12/2012 | Chen et al. |
| 2013/0005649 A1 | 1/2013 | Niemoeller et al. |
| 2013/0012433 A1 | 1/2013 | Rosskamp et al. |
| 2013/0023467 A1 | 1/2013 | Silvestre et al. |
| 2013/0040878 A1 | 2/2013 | Silvestre |
| 2013/0065828 A1 | 3/2013 | Ruus et al. |
| 2013/0079279 A1 | 3/2013 | Becker et al. |
| 2013/0085102 A1 | 4/2013 | Silvestre |
| 2013/0096059 A1 | 4/2013 | Stechl et al. |
| 2013/0096060 A1 | 4/2013 | Stechl et al. |
| 2013/0203666 A1 | 8/2013 | Niemoeller et al. |
| 2013/0284912 A1 | 10/2013 | Vogel et al. |
| 2013/0296236 A1 | 11/2013 | Silvestre |
| 2014/0148384 A1 | 5/2014 | Boka et al. |
| 2014/0206611 A1 | 7/2014 | Becker et al. |
| 2014/0248365 A1 | 9/2014 | Rademacher et al. |

FOREIGN PATENT DOCUMENTS

| | | |
|---|---|---|
| CA | 1 173 388 | 8/1984 |
| CA | 1 341 203 | 11/1986 |
| CA | 1 258 427 | 8/1989 |
| CA | 1 336 329 | 7/1995 |
| CN | 1276731 | 12/2000 |
| CN | 1413582 | 4/2003 |
| CN | 101366692 | 2/2009 |
| CN | 101444618 | 6/2009 |
| CN | 101454019 | 6/2009 |
| CN | 101670096 | 3/2010 |
| DE | 196 37 230 | 3/1998 |
| DE | 10 2008 003 566 | 7/2009 |
| DE | 10 2008 003 568 | 7/2009 |
| DE | 10 2008 053 048 | 4/2010 |
| EP | 0 018 609 | 4/1980 |
| EP | 0 046 979 | 8/1981 |
| EP | 0 132 769 | 2/1985 |
| EP | 0 140 084 | 5/1985 |
| EP | 0 166 529 | 1/1986 |
| EP | 0 194 864 | 3/1986 |
| EP | 0 200 383 | 11/1986 |
| EP | 0 211 299 | 2/1987 |
| EP | 0 214 826 | 3/1987 |
| EP | 0 224 885 | 6/1987 |
| EP | 0 227 938 | 7/1987 |
| EP | 0 229 956 | 7/1987 |
| EP | 0 229 998 | 7/1987 |
| EP | 0 254 516 | 1/1988 |
| EP | 0 305 760 | 3/1989 |
| EP | 0 368 187 | 5/1990 |
| EP | 0 375 437 | 6/1990 |
| EP | 0 383 472 | 8/1990 |
| EP | 0 419 504 | 1/1994 |
| EP | 0 600 372 | 6/1994 |
| EP | 0 668 282 | 8/1995 |
| EP | 0 668 292 | 8/1995 |
| EP | 0 678 522 | 10/1995 |
| EP | 0 837 072 | 4/1998 |
| EP | 0 845 265 | 6/1998 |
| EP | 0 885 961 | 12/1998 |
| EP | 1 076 066 | 2/2001 |
| EP | 1 117 114 | 1/2002 |
| EP | 1 222 207 | 7/2002 |
| EP | 1 523 993 | 4/2005 |
| EP | 2 112 161 | 10/2009 |
| EP | 2 324 853 | 5/2011 |
| EP | 2 329 848 | 6/2011 |
| EP | 2 389 945 | 11/2011 |
| EP | 0 921 812 | 12/2011 |
| EP | 2 387 989 | 7/2014 |
| FR | 2 456 522 | 12/1980 |
| GB | 0 835 638 | 5/1960 |
| GB | 0 840 870 | 7/1960 |
| GB | 1 527 605 | 10/1978 |
| GB | 1 554 157 | 10/1979 |
| JP | 61-212598 | 9/1986 |
| JP | 63-99096 | 9/1988 |
| JP | 2-218696 | 8/1990 |
| JP | 2-264798 | 10/1990 |
| JP | 3-504240 | 9/1991 |
| JP | 6-506444 | 7/1994 |
| JP | 2001-521004 | 11/2001 |
| JP | 2002-516880 | 6/2002 |
| JP | 2006-137678 | 1/2006 |
| JP | 2006-515267 | 5/2006 |
| JP | 2007-204498 | 8/2007 |
| JP | 2009-091363 | 4/2009 |
| JP | 2012-255040 | 12/2012 |
| RU | 2386631 | 9/2008 |
| TW | 157005 | 5/1991 |
| TW | 562806 | 11/2003 |
| WO | WO 83/00288 | 2/1983 |
| WO | WO 88/06599 | 9/1988 |
| WO | WO 89/10937 | 11/1989 |
| WO | WO 90/07522 | 7/1990 |
| WO | WO 90/11299 | 10/1990 |
| WO | WO 91/03550 | 3/1991 |
| WO | WO 91/16929 | 11/1991 |
| WO | WO 92/00321 | 1/1992 |
| WO | WO 92/12999 | 8/1992 |
| WO | WO 93/18786 | 9/1993 |
| WO | WO 94/14461 | 7/1994 |
| WO | WO 95/00550 | 1/1995 |
| WO | WO 95/24183 | 9/1995 |
| WO | WO 96/04307 | 2/1996 |
| WO | WO 96/07399 | 3/1996 |
| WO | WO 96/11705 | 4/1996 |
| WO | WO 96/32414 | 10/1996 |
| WO | WO 96/34882 | 11/1996 |
| WO | WO 96/41606 | 12/1996 |
| WO | WO 97/01331 | 1/1997 |
| WO | WO 97/48413 | 12/1997 |
| WO | WO 98/05351 | 2/1998 |
| WO | WO 98/08531 | 3/1998 |
| WO | WO 98/08871 | 3/1998 |
| WO | WO 98/08873 | 3/1998 |
| WO | WO 98/19698 | 5/1998 |
| WO | WO 98/30231 | 7/1998 |
| WO | WO 98/35033 | 8/1998 |
| WO | WO 98/39022 | 9/1998 |
| WO | WO 98/42749 | 10/1998 |
| WO | WO 98/56406 | 12/1998 |
| WO | WO 98/56418 | 12/1998 |

(56) References Cited

FOREIGN PATENT DOCUMENTS

| | | |
|---|---|---|
| WO | WO 99/07404 | 2/1999 |
| WO | WO 99/21573 | 5/1999 |
| WO | WO 99/21578 | 5/1999 |
| WO | WO 99/24071 | 5/1999 |
| WO | WO 99/25727 | 5/1999 |
| WO | WO 99/25728 | 5/1999 |
| WO | WO 99/40788 | 8/1999 |
| WO | WO 99/43708 | 9/1999 |
| WO | WO 99/46283 | 9/1999 |
| WO | WO 99/62558 | 12/1999 |
| WO | WO 00/23098 | 4/2000 |
| WO | WO 00/23099 | 4/2000 |
| WO | WO 00/29013 | 5/2000 |
| WO | WO 00/41546 | 7/2000 |
| WO | WO 00/66629 | 11/2000 |
| WO | WO 00/74736 | 12/2000 |
| WO | WO 01/00223 | 1/2001 |
| WO | WO 01/02039 | 1/2001 |
| WO | WO 01/04156 | 1/2001 |
| WO | WO 01/12155 | 2/2001 |
| WO | WO 01/21154 | 3/2001 |
| WO | WO 01/25278 | 4/2001 |
| WO | WO 01/28555 | 4/2001 |
| WO | WO 01/37808 | 5/2001 |
| WO | WO 01/43762 | 6/2001 |
| WO | WO 01/51071 | 7/2001 |
| WO | WO 01/52937 | 7/2001 |
| WO | WO 01/93837 | 12/2001 |
| WO | WO 02/00243 | 1/2002 |
| WO | WO 02/24214 | 3/2002 |
| WO | WO 02/064115 | 8/2002 |
| WO | WO 02/065985 | 8/2002 |
| WO | WO 02/066628 | 8/2002 |
| WO | WO 02/068660 | 9/2002 |
| WO | WO 02/070722 | 9/2002 |
| WO | WO 02/076495 | 10/2002 |
| WO | WO 02/079250 | 10/2002 |
| WO | WO 03/002021 | 1/2003 |
| WO | WO 03/020201 | 3/2003 |
| WO | WO 03/035028 | 5/2003 |
| WO | WO 03/035051 | 5/2003 |
| WO | WO 03/044210 | 5/2003 |
| WO | WO 03/053339 | 7/2003 |
| WO | WO 03/066084 | 8/2003 |
| WO | WO 03/094951 | 11/2003 |
| WO | WO 03/094956 | 11/2003 |
| WO | WO 03/101395 | 12/2003 |
| WO | WO 03/105888 | 12/2003 |
| WO | WO 2004/005342 | 1/2004 |
| WO | WO 2004/035623 | 4/2004 |
| WO | 2004/045592 | 6/2004 |
| WO | WO 2004/064862 | 8/2004 |
| WO | WO 2004/078196 | 9/2004 |
| WO | WO 2004/078197 | 9/2004 |
| WO | WO 2004/078198 | 9/2004 |
| WO | WO 2004/080480 | 9/2004 |
| WO | WO 2004/096854 | 11/2004 |
| WO | WO 2004/105781 | 12/2004 |
| WO | WO 2004/107979 | 12/2004 |
| WO | WO 2005/021022 | 3/2005 |
| WO | WO 2005/023291 | 3/2005 |
| WO | WO 2005/028516 | 3/2005 |
| WO | WO 2005/046716 | 5/2005 |
| WO | WO 2005/048950 | 6/2005 |
| WO | WO 2005/112949 | 12/2005 |
| WO | WO 2005/117948 | 12/2005 |
| WO | WO 2006/000567 | 1/2006 |
| WO | WO 2006/015879 | 2/2006 |
| WO | WO 2006/029634 | 3/2006 |
| WO | WO 2006/051103 | 5/2006 |
| WO | WO 2006/051110 | 5/2006 |
| WO | WO 2006/058620 | 6/2006 |
| WO | WO 2006/110551 | 10/2006 |
| WO | WO 2007/001150 | 1/2007 |
| WO | WO 2007/024700 | 3/2007 |
| WO | WO 2007/028394 | 3/2007 |
| WO | WO 2007/031187 | 3/2007 |
| WO | WO 2007/035665 | 3/2007 |
| WO | WO 2007/036299 | 4/2007 |
| WO | WO 2007/037607 | 4/2007 |
| WO | WO 2007/044867 | 4/2007 |
| WO | WO 2007/050656 | 5/2007 |
| WO | WO 2007/075534 | 7/2007 |
| WO | WO 2007/081824 | 7/2007 |
| WO | WO 2007/082381 | 7/2007 |
| WO | WO 2007/095288 | 8/2007 |
| WO | WO 2007/104786 | 9/2007 |
| WO | WO 2007/109221 | 9/2007 |
| WO | 2007120899 A2 | 10/2007 |
| WO | WO 2007/113205 | 10/2007 |
| WO | WO 2008/006496 | 1/2008 |
| WO | WO 2008/013938 | 1/2008 |
| WO | WO 2008/023050 | 2/2008 |
| WO | WO 2008/028914 | 3/2008 |
| WO | WO 2008/034881 | 3/2008 |
| WO | WO 2008/124522 | 10/2008 |
| WO | WO 2008/133908 | 11/2008 |
| WO | WO 2008/145323 | 12/2008 |
| WO | WO 2009/004627 | 1/2009 |
| WO | 2009/030498 | 3/2009 |
| WO | 2009/030499 | 3/2009 |
| WO | WO 2009/039963 | 4/2009 |
| WO | WO 2009/048959 | 4/2009 |
| WO | 2009/063072 A2 | 5/2009 |
| WO | WO 2009/056569 | 5/2009 |
| WO | WO 2009/087081 | 7/2009 |
| WO | WO 2009/087082 | 7/2009 |
| WO | WO 2009/089181 | 7/2009 |
| WO | WO 2009/098318 | 8/2009 |
| WO | WO 2009/102467 | 8/2009 |
| WO | WO 2009/134380 | 11/2009 |
| WO | WO 2010/030670 | 3/2010 |
| WO | WO 2010/043566 | 4/2010 |
| WO | WO 2010/044867 | 4/2010 |
| WO | WO 2010/092163 | 8/2010 |
| WO | WO 2011/017554 | 2/2011 |
| WO | WO 2011/012719 | 3/2011 |
| WO | WO 2011/029892 | 3/2011 |
| WO | 2011/058083 A1 | 5/2011 |
| WO | WO 2011/058082 | 5/2011 |
| WO | WO 2011/089203 | 7/2011 |
| WO | WO 2011/103575 | 8/2011 |
| WO | WO 2011/122921 | 10/2011 |
| WO | WO 2011/128374 | 10/2011 |
| WO | WO 2011/144673 | 11/2011 |
| WO | WO 2011/144674 | 11/2011 |
| WO | WO 2011/147980 | 12/2011 |
| WO | WO 2011/157402 | 12/2011 |
| WO | WO 2011/160066 | 12/2011 |
| WO | WO 2012/012352 | 1/2012 |
| WO | WO 2012/028172 | 3/2012 |
| WO | WO 2012/055967 | 5/2012 |
| WO | WO 2012/065996 | 5/2012 |
| WO | WO 2012/066086 | 5/2012 |
| WO | WO 2012/080320 | 6/2012 |
| WO | WO 2012/104342 | 8/2012 |
| WO | WO 2012/125569 | 9/2012 |
| WO | WO 2012/156296 | 11/2012 |
| WO | WO 2012/156299 | 11/2012 |
| WO | 2012/177929 A2 | 12/2012 |
| WO | WO 2013/060850 | 5/2013 |
| WO | WO 2014/017849 | 1/2014 |
| WO | WO 2014/118355 | 8/2014 |

OTHER PUBLICATIONS

Korczyn, A.D. and Nussbaum, M., "Emerging Therapies in the Pharmacological Treatment of Parkinson's Disease," Drugs 62:775-766 (2002).*

Martin, et al. "Neurodegeneration in excitotoxcity, global cerebral ischemia, and target deprivation: A perspective on the contributions of aptopsis and necrosis," Brain Res. Bull, 46:281-309 (1998).*

Kim et al, "Exendin-4 protects dopaminergic neurons by inhibition of microglial activation and matrix metalloproteinase-3 expression in

(56) References Cited

OTHER PUBLICATIONS an animal model of Parkinson's disease," J. Endocrin. 202:431-439 (2009).*
Hunter, Kerry et al "Drugs developed to treat diabetes, liraglutide and lixisenatide, cross the blood brain barrier and enhance neurogenesis", BMC Neuroscience, Biomed Central (2012) vol. 13, p. 6.
Christensen, Mikkel et al "Lixisenatide, a novel GLP-1 receptor agonist for the treatment of type 2 diabetes mellitus", IDrugs: The Investigational Drugs Journal, Current Drugs Ltd. (2009) vol. 12 No. 8, pp. 503-513.
Campas, C. et al "Ave-0010 GLP-1 Receptor Agonist Treatment of Diabetes", Drugs of the Future, Prous Science (2008) vol. 33 No. 10, pp. 838-840.
McClean, Paula et al "The Diabetes Drug Liraglutide Prevents Degenerative Processes in a Mouse Model of Alzheimer's Disease" The Journal of Neuroscience: The Official Journal of the Society for Neuroscience (2011) vol. 31 No. 17, pp. 6587-6594.
Perry, Tracyann et al "Evidence of GLP-1-mediated neuroprotection in an animal model of pyridoxine-induced peripheral sensory neuropathy", Experimental Neruology, Academic Press (2007) vol. 203 No. 2, pp. 293-301.
Kastin, AJ et al "Entry of exedin-4 into brain is rapid but may be limited at high doses" International Journal of Obesity and Related Metabolic Disorders: Journal of the International Association for the Study of Obesity (2003) vol. 27 No. 3, pp. 313-318.
Holscher, Christian "Incretin Analogues that have been Developed to Treat Type 2 Diabetes Hold Promise as a Novel Treatment Strategy for Alzheimer's Disease" Recent Patents on CNS Drug Discovery (2010) vol. 5 No. 2, pp. 109-117.
Hamilton, Alison et al "Receptors for the incretin glucagon-like peptide-1 are expressed on neurons in the central nervous system" Neuroreport (2009) vol. 20 No. 13, pp. 1161-1166.
Bronwen, Martin et al "Exendin-4 Improves Glycemic Control, Ameliorates Brain and Pancreatic Pathologies, and Extends Survival in a Mouse Model of Huntington's Disease" Diabetes(2009) vol. 58 No. 2, pp. 318-328.
International Search Report corresponding to PCT/EP2012/067144, dated Aug. 11, 2012.
Hölscher, C. et al., "New roles for insulin-like hormones in neuronal signaling and protection: New hopes for novel treatments of Alzheimer's disease" Neurobiology of Aging (2010) pp. 1495-1502, vol. 31.
Hölscher, C., "The role of GLP-1 in neuronal activity and neurodegeneration" Vitamins and hormones (2010b) pp. 331-354, vol. 84.
McClean, P.L. et al., "The diabetes drug Liraglutide prevents degenerative processes in a mouse model of Alzheimer's disease" Journal of Neuroscience (2011) pp. 6587-6594, vol. 31.
Li, H. et al., "Chronic treatment of exendin-4 affects cell proliferation and neuroblast differentiation in the adult mouse hippocampal dentate gyrus" Neuroscience Letters (2010) pp. 1205-1219, vol. 19.
Li, Y. et al., "GLP-1 Receptor Stimulation Reduces Amyloid-beta Peptide Accumulation and Cytotoxicity in Cellular and Animal Models of Alzheimer's Disease" J Alzheimers Dis (2010) pp. 1205-1219, vol. 19.
Perry, T. et al., "A novel neurotrophic property of glucagon-like peptide 1: a promoter of nerve cell growth factor mediated differentiation on PC12 cells" J Pharmacol exp (2002) pp. 958-966, vol. 300.
Perry, T.A. et al., "Protection and reversal of excitotoxic neuronal damage by glucagon-like peptide-1 and exendin-4" J Pharmacol Exp Ther (2002b) pp. 881-888, vol. 302.
Harkavyi, A. et al., "Glucagon-like peptide I receptor stimulation reverses key deficits in distinct rodent models of Parkinson's disease" J Neuroinflamm (2008) pp. 1-9, vol. 5, No. 19.
Li, A. et al., "GLP-1 receptor stimulation preserves primary cortical and dopaminergic neurons in cellular and rodent models of stroke and Parkinsons" PNAS (2009) pp. 1285-1290, vol. 106, No. 4.

Martin, B. et al., "Exendin-4 improves glycemic control, ameliorates brain and pancreatic pathologies and extends survival in a mouse model of Huntington's Disease" Diabetes (2009) pp. 318-328, vol. 58, No. 2.
Lee, C.H. et al., "Ischemia-induced changes in glucagon-like peptide-1 receptor and neuroprotective effect of its agonist exendin-4, in experimental transient cerebral ischemia" J Neurosc Res (2011) pp. 1103-1113, vol. 89.
Teramoto, S. et al., "Exendin-4, a glucagon-like peptide -1 receptor agonist, provides neuroprotection in mice transient focal cerebral ischemia" J Cerebr Blood Flow Metab (2011) pp. 1696-1705, vol. 31, No. 8.
Nakagawa, A. et al., "Receptor gene expression of glucagon-like peptide-1, but not of glucose-dependent insulinotropic polypeptide, in rat nodose ganglion cells" Auton Neurosci (2004) pp. 36-43, vol. 110.
Perry, T.A. et al., "Evidence of GLP-1-mediated neuroprotection in an animal model of pyridoxine-induced peripheral sensory neuropathy" Exp Neurol (2007) pp. 293-301, vol. 203, No. 2.
During, M.H. et al., "Glucagon-like peptide-1 receptor is involved in learning and neuroprotection" Nat Med (2003) pp. 1173-1179, vol. 9.
Isacson, R. et al., "The glucagon-like peptide 1 receptor agonist exendin-4 improves reference memory performance and decreases immobility in the forced swim test" Eur J Pharmacol (2009) pp. 249-255, vol. 10, No. 650.
Himeno, T. et al., "Beneficial effects of exendin-4 on experimental polyneuropathy in diabetic mice" Diabetes (2011) pp. 2397-2406, vol. 60.
Porter, D.W. et al., "Four weeks administration of Liraglutide improves memory and learning as well as glycemic control in mice with high fat dietary-induced obesity and insulin resistance" Diab Obes Metab (2010) pp. 891-899, vol. 12.
Doyle, M.E. et al., "Mechanisms of action of glucagon-like peptide 1 in the pancreas" Pharmacol Ther. (Mar. 2007) pp. 546-593, vol. 113, No. 3.
Holst, J.J., "Glucagon-like Peptide-1, A Gastrointestinal Hormone with a Pharmaceutical Potential" Curr. Med. Chem (1999) pp. 1005-1017, vol. 6.
Nauck, M.A. et al., "Glucagon-like Peptide 1 (GLP-1) as a new therapeutic approach for Type 2-diabetes" Exp Clin Endocrinol Diabetes (1997) pp. 187-195, vol. 105.
Lopez-Delgado, M.I. et al., "Effects of Glucagon-Like Peptide 1 on the Kinetics of Glycogen Synthase a in Hepatocytes from Normal and Diabetic Rats" Endocrinology (1998) pp. 2811-2817, vol. 139, No. 6.
McClean, P.L. et al., "Glucagon-like peptide-1 analogues enhance synaptic plasticity in the brain: A link between diabetes and Alzheimer's disease" European Journal of Pharmacology (2010) pp. 158-162, vol. 630.
Kastin, A.J. et al., "Interactions of Glucagon-like peptide (GLP-1) with blood brain barrier" Journal of Molecular Neuroscience (2001) pp. 7-14, vol. 18, No. 2.
Perry, T. et al., "The glucagon-like peptides: a double-edged therapeutic sword" Trends in Pharmacological Sciences (2003) pp. 377-383, vol. 24.
Hamilton, A. et al., "Novel GLP-1 mimetics developed to treat type 2 diabetes promote progenitor cell proliferation in the brain" J Neurosci Res (2011) pp. 481-489, vol. 89.
Gengler, S. et al., "Val(8)GLP-1 rescues synaptic plasticity and reduces dense core plaques in APP/PS1 mice" Neurobiol Aging (2012) pp. 265-276, vol. 33.
Kim, S. et al., "Exendin-4 protects dopaminergic neurons by inhibition of microglial activation and matrix metalloproteinase-3 expression in an animal model of Parkinson's disease" J. Endocrinology (2009) pp. 431-439, vol. 202.
Bertram L, Lill CM, and Tanzi RE, 2010. The Genetics of Alzheimer Disease: Back to the Future, Neuron, 68, 270-281.
Mancuso M, Orsucci D, LoGerfo A, Calsolaro V, Siciliano G, 2010, Clinical features and pathogenesis of Alzheimer's disease: involvement of mitochondria and mitochondrial DNA, Adv Exp Med Biol., 685, 34-44.

(56) References Cited

OTHER PUBLICATIONS

Varadarajan S, Yatin S, Aksenova M, and Butterfield DA, 2000, Review: Alzheimer's Amyloid b-Peptide-Associated Free Radical Oxidative Stress and Neurotoxicity, Journal of Structural Biology, 130, 184-208.
Aderinwale OG, Ernst HW, Mousa SA, 2010, Current therapies and new strategies for the management of Alzheimer's disease, Am J Alzheimers Dis Other Demen., 25(5), 414-24.
Holscher C, 2005, Development of Beta-Amyloid-induced neurodegeneration in Alzheimer's disease and novel neuroprotective strategies, Reviews in Neuroscience, 16, 181-212.
Gandhi S, Wood NW, 2005, Molecular pathogenesis of Parkinson's disease. Hum Mol Genet 14: 2749-2755.
Schapira AH, 2001, Causes of neuronal death in Parkinson's disease. Adv Neurol 86: 155-162.
Li H, Lee CH, Yoo KY, Choi JH, Park OK, Yan BC. Byun K, Lee B, Hwang JK.Won MH, 2010, Chronic treatment of exendin-4 affects cell proliferation and neuroblast differentiation in the adult mouse hippocampal dentate gyrus. Neurosci Lett 19: 1205-1219.
Sherer, T.B. Kim, J.-H, Betarbet, R. and Greenamyre, J.T., 2003, Subcutaneous Rotenone Exposure Causes Highly Selective Dopaminergic Degeneration and a-Synuclein Aggregation, Experimental Neurology, 179: 9-16.
Dubois B. et al., 2010, Revising the definition of Alzheimer's disease: a new lexicon. Lancet Neurol. 9: 1118-27.
Higginsa G C, Bead P M, Shin Y S, Chene M J, Cheunge N S and Nagley P, 2010, Oxidative Stress: Emerging Mitochondrial and Cellular Themes and Variations in Neuronal Injury, Journal of Alzheimer's Disease, 20, S453-S473.
Wollen K A, 2010, Alzheimer's disease: the pros and cons of pharmaceutical, nutritional, botanical, and stimulatory therapies, with a discussion of treatment strategies from the perspective of patients and practitioners, Altern Med. Rev., 15β, 223-44.
Kaduszkiewicz, H., Zimmermann T, Beck-Bornholdt H P, van den Bussche H, 2005, Cholinesterase inhibitors for patients with Alzheimer's disease: systematic review of randomised clinical trials. BMJ 331: 321.
De Rosa, Garcia R, Braschi A A, Capsoni C, Maffei S, Berardi L, Cattaneo N, 2005, Intranasal administration of nerve growth factor (NGF) rescues recognition memory deficits in A D11 anti-NGF transgenic mice. Proc Natl Acad. Sci., 102, 3811-3816.
Mattson M P, 2007, Calcium and neurodegeneration. Aging Cell 6: 337-350.
Lotharius, J., Barg, S., Wiekop, P., Lundberg, C., Raymon, H. K., and Brundin, P., Effect of Mutant α-Synuclein on Dopamine Homeostasis in a New Human Mesencephalic Cell Line, 2002, Journal of Biological Chemistry, 277: 38884-38894.
Lotharius, J., Falsig, J., van Beek, J., Payne, S., Dringen, R., Brundin, P., and Leist, M., Progressive Degeneration of Human Mesencephalic Neuron-Derived Cells Triggered by Dopamine-Dependent Oxidative Stress is Dependent on the Mixed-Lineage Kinase Pathway, 2005, Journal of Neuroscience, 25: 6329-6342.
Tanner, C. M., Kamel, F., Ross, G. W. Hoppin, J. A., Goldman, S. M., Korell, M., Marras, C., Bhudhikanok, G. S., Kasten, M., Chade, A. R. Comyns, K., Richards, M. B., Meng, C., Priestley, B., Fernandez, H. H., Cambi, F., Umbach, D. M., Blair, A., Sandier, D. R, and Langston, J. W., Rotenone, Paraquat, and Parkinson's Disease, 2011, Environmental Health Perspectives, 119: 866-872.
Office Action dated Jan. 20, 2015 issues in the corresponding Chinese application No. 2012800038987.5.
Drucker DJ et al. "The incretin system: glucagon-like peptide-1 receptor agonists and dipeptidyl peptidase-4 inhibitors in type 2 diabetes." Lancet; 368(9548):1696-705 (Nov. 11, 2006).
Gault VA et al. "GLP-1 agonists facilitate hippocampal LTP and reverse the impairment of LTP induced by beta-amyloid." Eur J Pharmacol; 587(1-3):112-7 (Jun. 10, 2008; published online Mar. 29, 2008).
Faivre E et al. "Effect of GIP Analogues in Neuronal Signalling, Cell Proliferation and Learning and Memory." Regulatory Peptides; 164(1): 40-41 (Sep. 9, 2010, published online Aug. 20, 2010).

Perry TA et al. "A new Alzheimer's disease interventive strategy: GLP-1." Current Drug Targets;5(6):565-71 (Aug. 2004).
Pradier L et al. "Animal Models of Alzheimer's disease." Démences (Dementias); eds. Duyckaerts C. and Pasquier F.; publisher Doin; 165-170 (Sep. 10, 2002; available Aug. 27, 2002).
Press Release, "Diabetes drugs show promise in Alzheimer's" published Jan. 17, 2011, pp. 1-2.
NCT01255163, ClinicalTrials.gov "A Clinical Trial of Exendin-4 for the Treatment of Alzheimer's Disease" accessed Aug. 8, 2011, pp. 1-7.
NCT01174810, ClinicalTrials.gov "Exendin-4 as a Treatment for Parkinson's Disease—Pilot Study" accessed Aug. 8, 2011, pp. 1-5.
The International Preliminary Report on Patentability for International Application No. PCT/EP2012/067144, dated Sep. 27, 2013, pp. 1-11.
Communication pursuant to Article 94(3) EPC for EP application No. 12 755 853.4, dated Dec. 18, 2014, pp. 1-4.
Agholme et al., "An in Vitro Model for Neuroscience: Differentiation of SH-SY5Y Cells into Cells with Morphological and Biochemical Characteristics of Mature Neurons" J Alzheimer's Disease, 20:1069-82 (2010).
Banks et al., "Brain Uptake of the Glucagon-Like Peptide-1 Antagonist Exendin(9-39) after Intranasal Administration" Journal of Pharmacology and Experimental Therapeutics, 309:469-75 (2004).
Blanchard et al., "Time sequence of maturation of dystrophic neurites associate with Aβ deposits in APP/PS1 transgenic mice" Experimental Neurology, 184:247-63 (2003).
Boutajangout et al., "Characterisation of cytoskeletal abnormalities in mice transgenic for wild-type human tau and familial Alzheimer's disease mutants of APP and presenilin-1" Neurobiology of Disease, 15:47-60 (2004).
Boutajangout et al., "Increased tau phosphorylation but absence of formation of neurofibrillary tangles in mice double transgenic for human tau and Alzheimer mutant (M146L) presenilin-1" 318(1):29-33 (2003).
Casas et al., "Massive CA1/2 Neuronal Loss with Intraneuronal and N-Terminal Truncated Aβ 42 Accumulation in a Novel Alzheimer Transgenic Model" American Journal of Pathology 165(4):1289-1300 (2004).
Cheung et al., "Effects of all-trans-retinoic acid on human SH-SY5Y neuroblastoma as in vitro model in neurotoxicity research" NeuroToxicology, 30:127-35 (2009).
Czech et al., "Proteolytical processing of mutated human amyloid precursor protein in transgenic mice" Molecular Brain Research 47:108-116 (1997).
de Arriba et al., "Carbonyl stress and NMDA receptor activation contribute to methylglyoxal neurotoxicity" Free Radical Biology & Medicine, 40:779-90 (2006).
Delatour et al., "Alzheimer pathology disorganizes cortico-cortical circuitry: direct evidence from a transgenic animal model" Neurobiology of Disease, 16:41-47 (2004).
Eckert et al., "Alzheimer's Disease-like Alterations in Peripheral Cells from Presenilin-1 Transgenic Mice" Neurobiology of Disease 8, 331-342 (2001).
Holscher "Possible Causes of Alzheimer's Disease: Amyloid Fragments, Free Radical, and Calcium Homeostasis" Neurobiology of Disease 5:129-41 (1998).
Jang et al., "Neuroprotective Effects of Triticum aestivum L. against β-Amyloid-induced Cell Death and Memory Impairments" Phytother. Res. 24:76-84 (2010).
Jimenez et al., "Inflammatory Response in the Hippocampus of PS1M146L/APP751SL Mouse Model of Alzheimer's Disease: Age-Dependent Switch in the Microglial Phenotype from Alternative to Classic" Neurobiology of Disease, 28 (45):11650-661 (2008).
Kaech & Banker, "Culturing hippocampal neurons" Nat Protoc. 1(5):2406-15 (2006).
Langston et al., "Chronic Parkinsonism in Humans Due to a Product of Meperedine-Analog Synthesis" Science 219 (4587):979-80 (1983).
Langui et al., "Subcellular Topography of Neuronal AβPeptide in APPxPS1 Transgenic Mice" American Journal of Pathology 165(5):1465-77 (2004).

(56) References Cited

OTHER PUBLICATIONS

Li & Holscher, "Common pathological processes in Alzheimer disease and type 2 diabetes: A review" Brain Research Reviews, 56:384-402 (2007).
Li et al., "Enhancing the GLP-1 receptor signaling pathway leads to proliferation and neuroprotection in human neuroblastoma cells" Journal of Neurochemistry, 113:1621-631 (2010).
Moreno-Gonzalez et al.,"Extracellular Amyloid-β and Cytotoxic Glial Activation Induce Significant Entorhinal Neuron Loss in Young PS1M146L/APP751SL Mice" Journal of Alzheimer's Disease 18:755-776 (2009).
Nicklas et al.., "Inhibition of NADH-Linked Oxidation in Brain Mitochondria by 1-Methyl-4-Phenyl-Pyridine, A Metabolite of the Neurotoxin, 1-Methyl-4-Phenyl-1,2,5,6-Tetrahydropyridine" Life Sciences 36:2503-508 (1985).
Ramos et al., "Early neuropathology of somatostatin/NPY GABAergic cells in the hippocampus of a PS1 x APP transgenic model of Alzheimer's disease" Neurobiology of Aging, 27:1658-1672 (2006).
Schindowski et al., "Impact of Aging: Sporadic, and Genetic Risk Factors on Vulnerability to Apoptosis in Alzheimer's Disease" NeuroMolecular Medicine, 4:161-177 (2003).
Schmitz et al., "Hippocampal Neuron Loss Exceeds Amyloid Plaque Load in a Transgenic Mouse Model of Alzheimer's Disease" American Journal of Pathology, 164(4):1495-1502 (2004).
Stolk et al., "Insulin and cognitive function in an elderly population. The Rotterdam Study." Diabetes Care, 20:792-95(1997).
Tetich et al., "Neuroprotective effects of (24R)-1,24-dihydroxycholecalciferol in human neuroblastoma SH-SY5Y cell line" J Steroid Biochemistry & Molecular Biology 89-90:365-70 (2004).
Toth et al., "Neurite sprouting and synapse deterioration in the aging Caenorhabditis elegans nervous system" J Neurosci. 32(26):8778-90 (2012).
Venezia et al., "Apoptotic cell death and amyloid precursor protein signaling in neuroblastoma SH-SY5Y cells," Ann NY Acad Sci., 1030:339-47 (2004).
Watson et al., "Insulin increases CSF Aβ42 levels in normal older adults" Neurology 60:1899-1903 (2003).
Wirths et al., "Intraneuronal APP/Aβ Trafficking and Plaque Formation in β-Amyloid Precursor Protein and Presenilin-1 Transgenic Mice" Brain Pathol. 12:275-286 (2002).
Wirths et al., "Reelin in plaques of beta-amyloid precursor protein and presenilin-1 double-transgenic mice." Neurosci Lett. 316(3):145-48 (2001).
Wirths et al., "Intraneuronal Abeta accumulation precedes plaque formation in beta-amyloid precursor protein and presenilin-1 double-transgenic mice." Neurosci Lett. 306(1-2):116-20 (2001).
NHSC—National Horizon Scanning Center, "AVE0010 (ZP10) for type 2 diabetes mellitus" University of Birmingham, England; pp. 1-6 (Dec. 2008).
Search Report of the Intellectual Property Office of Singapore for Patent Application No. 10201500871T, dated Nov. 2, 2015, pp. 1-3.
NCT01146678, ClinicalTrials.gov "Relative Bioavailability and Activity of Different Formulations of Insulin Glargine and Lixisenatide in Patients With Diabetes Mellitus Type 1" last updated Sep. 10, 2010, pp. 1-4.
EMA—Science Medicines Health "TOUJEO" EPAR Summary for the Public, first published Nov. 5, 2009, pp. 1-3.
U.S. Appl. No. 13/123,835, filed Sep. 30, 2011 to Werner et al.
U.S. Appl. No. 13/382,442, filed Mar. 21, 2012 to Schoettle.
U.S. Appl. No. 13/382,772, filed May 29, 2012 to Schoettle.
U.S. Appl. No. 13/509,507, filed Jul. 30, 2014 to Brunner-Schwarz et al.
U.S. Appl. No. 13/509,542, filed Aug. 2, 2012 to Hagendorf et al.
U.S. Appl. No. 14/172,151, filed Feb. 4, 2014 to Bley et al.
U.S. Appl. No. 12/617,805, filed Nov. 13, 2009 to Silvestre et al.
U.S. Appl. No. 12/617,811, filed Nov. 13, 2009 to Silvestre et al.
U.S. Appl. No. 14/220,562; filed Mar. 20, 2014 to Becker et al.
U.S. Appl. No. 13/700,631, filed Nov. 11, 2012 to Becker et al.
U.S. Appl. No. 13/819,114, filed Apr. 29, 2013 to Boka et al.
U.S. Appl. No. 13/363,956, filed Feb. 1, 2012 to Silvestre et al.
U.S. Appl. No. 13/432,811, filed Mar. 28, 2012 to Boka et al.
U.S. Appl. No. 13/469,633, filed May 11, 2012 to Ruus et al.
U.S. Appl. No. 13/467,707, filed May 9, 2012 to Niemoller et al.
U.S. Appl. No. 13/468,422, filed May 10, 2012 to Silvestre et al.
U.S. Appl. No. 13/467,757, filed May 9, 2012 to Silvestre et al.
U.S. Appl. No. 13/633,563, filed Oct. 2, 2012 to Stechl et al.
U.S. Appl. No. 13/595,590, filed Aug. 27, 2012 to Niemoeller et al.
U.S. Appl. No. 13/661,476, filed Oct. 26, 2012 to Silvestre et al.
U.S. Appl. No. 14/303,895, filed Jun. 13, 2014 to Souhami et al.
U.S. Appl. No. 13/633,496, filed Oct. 2, 2012 to Stechl et al.
Search Report of the Intellectual Property Corporation of Malaysia for Malaysian Patent Application No. PI 2011006204; dated Sep. 15, 2015, pp. 1-3.
Search Report of the Indecopi for Patent Application in Peru No. 000643-2012/DIN, dated Jul. 23, 2015, pp. 1-2.
Smolka et al., "Optimization of the isotope-coded affinity tag-labeling procedure for quantitative proteome analysis." Anal Biochem. 297(1):25-31 (Oct. 2001). Abstract only submitted.
Non-Final Office Action issued in U.S. Appl. No. 13/123,835; mailed May 28, 2015, pp. 1-11.
Non-Final Office Action issued in U.S. Appl. No. 13/123,835; mailed Dec. 22, 2014, pp. 1-13.
Final Office Action issued in U.S. Appl. No. 13/123,835; mailed Feb. 12, 2013, pp. 1-13.
Non-Final Office Action issued in U.S. Appl. No. 13/123,835; mailed Jul. 19, 2012, pp. 1-14.
Non-Final Rejection issued in U.S. Appl. No. 13/382,442; mailed Feb. 5, 2015, pp. 1-31.
Final Rejection issued in U.S. Appl. No. 13/382,442; mailed Jun. 13, 2014, pp. 1-29.
Non-Final Rejection issued in U.S. Appl. No. 13/382,442; mailed Dec. 19, 2013, pp. 1-29.
Final Rejection issued in U.S. Appl. No. 13/382,442; mailed Jul. 17, 2013, pp. 1-30.
Non-Final Rejection issued in U.S. Appl. No. 13/382,442; mailed Nov. 7, 2012, pp. 1-26.
Non-Final Rejection issued in U.S. Appl. No. 13/382,772; mailed Sep. 14, 2015, pp. 1-42.
Final Rejection issued in U.S. Appl. No. 13/382,772; mailed Feb. 10, 2015, pp. 1-36.
Non-Final Rejection issued in U.S. Appl. No. 13/382,772; mailed Sep. 29, 2014, pp. 1-33.
Final Rejection issued in U.S. Appl. No. 13/382,772; mailed Jun. 3, 2014, pp. 1-34.
Non-Final Rejection issued in U.S. Appl. No. 13/382,772; mailed Nov. 21, 2013, pp. 1-42.
Non-Final Rejection issued in U.S. Appl. No. 13/382,772; mailed Apr. 10, 2013, pp. 1-48.
Final Rejection issued in U.S. Appl. No. 12/617,811; mailed Jul. 31, 2015, pp. 1-15.
Non-Final Rejection issued in U.S. Appl. No. 12/617,811; mailed Jan. 14, 2015, pp. 1-15.
Final Rejection issued in U.S. Appl. No. 12/617,811; mailed Jan. 4, 2013, pp. 1-6.
Non-Final Rejection issued in U.S. Appl. No. 12/617,811; mailed Jun. 21, 2012, pp. 1-7.
Non-Final Rejection issued in U.S. Appl. No. 12/617,811; mailed Oct. 27, 2011, pp. 1-13.
Non-Final Rejection issued in U.S. Appl. No. 12/617,811; mailed Apr. 27, 2011, pp. 1-10.
Non-Final Office Action from U.S Appl. No. 12/617,805; mailed Sep. 15, 2015, pp. 1-12.
Final Office Action from U.S. Appl. No. 12/617,805; mailed Jan. 13, 2015, pp. 1-11.
Non-Final Office Action from U.S Appl. No. 12/617,805; mailed Jul. 24, 2014, pp. 1-12.
Final Office Action from U.S. Appl. No. 12/617,805; mailed Feb. 11, 2013, pp. 1-13.
Non-Final Office Action from U.S Appl. No. 12/617,805; mailed May 2, 2012, pp. 1-11.

(56) References Cited

OTHER PUBLICATIONS

Final Office Action from U.S. Appl. No. 12/617,805; mailed Jan. 12, 2012, pp. 1-14.
Non-Final Office Action from U.S Appl. No. 12/617,805; mailed May 10, 2011, pp. 1-12.
Non-Final Rejection issued in U.S. Appl. No. 13/509,507; mailed Dec. 8, 2015, pp. 1-14.
Final Rejection issued in U.S. Appl. No. 13/509,507; mailed Jul. 23, 2015, pp. 1-11.
Non-Final Rejection issued in U.S. Appl. No. 13/509,507; mailed Feb. 19, 2015, pp. 1-10.
Non-Final Rejection issued in U.S. Appl. No. 13/509,507; mailed Sep. 19, 2014, pp. 1-9.
Non-Final Rejection issued in U.S. Appl. No. 13/509,507; mailed Aug. 6, 2013, pp. 1-11.
Non-Final Rejection issued in U.S. Appl. No. 13/509,542; mailed Aug. 11, 2015, pp. 1-30.
Final Rejection issued in U.S. Appl. No. 13/509,542, mailed Jan. 28, 2015, pp. 1-26.
Non-Final Rejection issued in U.S. Appl. No. 13/509,542; mailed Apr. 2, 2014, pp. 1-20.
Final Rejection issued in U.S. Appl. No. 13/509,542; mailed Nov. 21, 2013, pp. 1-34.
Non-Final Rejection issued in U.S. Appl. No. 13/509,542; mailed May 23, 2013, pp. 1-21.
Final Rejection issued in U.S. Appl. 14/172,151; mailed Jul. 20, 2015, pp. 1-18.
Non-Final Rejection issued in U.S. Appl. 14/172,151; mailed Mar. 24, 2015, pp. 1-16.
Non-Final Rejection issued in U.S. Appl. No. 14/220,562; mailed Apr. 8, 2015, pp. 1-18.
Non-Final Rejection issued in U.S. Appl. No. 13/700,631; mailed Apr. 22, 2013, pp. 1-27.
Non-Final Rejection issued in U.S. Appl. No. 13/700,631; mailed Nov. 29, 2013, pp. 1-23.
Final Rejection issued in U.S. Appl. No. 13/700,631; mailed Jun. 18, 2014, pp. 1-25.
Non-Final Rejection issued in U.S. Appl. No. 13/700,631; mailed Nov. 18, 2014, pp. 1-22.
Final Rejection issued in U.S. Appl. No. 13/700,631; mailed Apr. 13, 2015, pp. 1-19.
Non-Final Rejection issued in U.S. Appl. No. 13/700,631; mailed Dec. 17, 2015, pp. 1-18.
Non-Final Rejection issued in U.S. Appl. No. 13/819,114; mailed Jul. 31, 2014, pp. 1-9.
Final Rejection issued in U.S. Appl. No. 13/819,114; mailed Mar. 2, 2015, pp. 1-10.
Non-Final Rejection issued in U.S. Appl. No. 13/819,114; mailed Dec. 2, 2015, pp. 1-14.
Non-Final Rejection issued in U.S. Appl. No. 13/363,956; mailed Apr. 10, 2013, pp. 1-15.
Non-Final Rejection issued in U.S. Appl. No. 13/363,956; mailed Nov. 20, 2013, pp. 1-10.
Final Rejection issued in U.S. Appl. No. 13/363,956; mailed May 20, 2014, pp. 1-16.
Non-Final Rejection issued in U.S. Appl. No. 13/363,956; mailed Feb. 11, 2015, pp. 1-18.
Non-Final Rejection issued in U.S. Appl. No. 13/363,956; mailed May 29, 2015, pp. 1-17.
Non-Final-Rejection issued in U.S. Appl. No. 13/432,811; mailed Apr. 8, 2013, pp. 1-7.
Non-Final-Rejection issued in U.S. Appl. No. 13/432,811; mailed Jul. 29, 2014, pp. 1-8.
Final-Rejection issued in U.S. Appl. No. 13/432,811; mailed Sep. 6, 2014, pp. 1-8.
Final-Rejection issued in U.S. Appl. No. 13/432,811; mailed Dec. 12, 2014, pp. 1-8.
Final-Rejection issued in U.S. Appl. No. 13/432,811; mailed Mar. 31, 2015, pp. 1-9.
Non-Final-Rejection issued in U.S. Appl. No. 13/432,811; mailed Sep. 9, 2015, pp. 1-11.
Non-Final Rejection issued in U.S. Appl. No. 13/469,633; mailed Mar. 27, 2013, pp. 1-39.
Non-Final Rejection issued in U.S. Appl. No. 13/469,633; mailed Aug. 19, 2013, pp. 1-25.
Final Rejection issued in U.S. Appl. No. 13/469,633; mailed Dec. 4, 2013, pp. 1-17.
Non-Final Rejection issued in U.S. Appl. No. 13/469,633; mailed Aug. 22, 2014, pp. 1-23.
Final Rejection issued in U.S. Appl. No. 13/469,633; mailed Jan. 23, 2015, pp. 1-12.
Non-Final Rejection issued in U.S. Appl. No. 13/467,707; mailed Jul. 15, 2013, pp. 1-20.
Final Rejection issued in U.S. Appl. No. 13/467,707; mailed Feb. 25, 2014, pp. 1-18.
Non-Final Rejection issued in U.S. Appl. No. 13/467,707; mailed Jul. 25, 2014, pp. 1-22.
Final Rejection issued in U.S. Appl. No. 13/467,707; mailed Jan. 7, 2015, pp. 1-8.
Non-Final Rejection issued in U.S. Appl. No. 13/467,707; mailed Sep. 16, 2015, pp. 1-13.
Final Rejection issued in U.S. Appl. No. 13/110,568; mailed Feb. 21, 2013, pp. 1-20.
Non-Final Rejection issued in U.S. Appl. No. 13/110,568; mailed Mar. 19, 2012, pp. 1-18.
Non-Final Rejection issued in U.S. Appl. No. 13/310,118, mailed Mar. 25, 2015, pp. 1-15.
Non-Final Rejection issued in U.S. Appl. No. 13/310,118, mailed Mar. 29, 2013, pp. 1-21.
Final Rejection issued in U.S. Appl. No. 13/310,118; mailed Aug. 2, 2012, pp. 1-20.
Non-Final Rejection issued in U.S. Appl. No. 13/310,118; mailed Mar. 19, 2012, pp. 1-19.
Non-Final Rejection issued in U.S. Appl. No. 13/467,757; mailed Apr. 17, 2013, pp. 1-9.
Non-Final Rejection issued in U.S. Appl. No. 13/595,590; mailed Jun. 5, 2015, pp. 1-9.
Final Rejection issued in U.S. Appl. No. 13/595,590; mailed Dec. 19, 2014, pp. 1-14.
Non-Final Rejection issued in U.S. Appl. No. 13/595,590; mailed Sep. 5, 2014, pp. 1-10.
Final Rejection issued in U.S. Appl. No. 13/595,590; mailed Apr. 2, 2014, pp. 1-7.
Non-Final Rejection issued in U.S. Appl. No. 13/595,590; mailed Oct. 16, 2013, pp. 1-7.
Non-Final Rejection in U.S. Appl. No. 13/633,563; mailed Jul. 1, 2013, pp. 1-56.
Final Rejection in U.S. Appl. No. 13/633,563; mailed Dec. 16, 2013, pp. 1-58.
Non-Final Rejection in U.S. Appl. No. 13/633,563; mailed Jun. 4, 2014, pp. 1-11.
Non-Final Rejection in U.S. Appl. No. 13/633,563; mailed Dec. 1, 2014, pp. 1-9.
Final Rejection in U.S. Appl. No. 13/633,563; mailed Apr. 22, 2015, pp. 1-12.
Non-Final Rejection in U.S. Appl. No. 13/633,563; mailed Oct. 6, 2015, pp. 1-12.
Non-Final Rejection in U.S. Appl. No. 13/633,496; mailed Apr. 29, 2013, pp. 1-53.
Final Rejection in U.S. Appl. No. 13/633,496; mailed Nov. 4, 2013, pp. 1-7.
Non-Final Rejection in U.S. Appl. No. 13/633,496; mailed May 22, 2014, pp. 1-11.
Final Rejection in U.S. Appl. No. 13/633,496; mailed Nov. 18, 2014, pp. 1-11.
Non-Final Rejection in U.S. Appl. No. 13/633,496; mailed Apr. 6, 2015, pp. 1-14.
Non-Final Rejection issued in U.S. Appl. No. 13/468,422; mailed Mar. 27, 2013, pp. 1-27.
Non-Final Rejection issued in U.S. Appl. No. 13/468,422; mailed Sep. 16, 2013, pp. 1-19.

(56) References Cited

OTHER PUBLICATIONS

Final Rejection issued in U.S. Appl. No. 13/468,422; mailed Jan. 6, 2014, pp. 1-21.
Non-Final Rejection issued in U.S. Appl. No. 13/468,422; mailed Jun. 4, 2014, pp. 1-24.
Final Rejection issued in U.S. Appl. No. 13/468,422; mailed Jan. 23, 2015, pp. 1-27.
Non-Final Rejection issued in U.S. Appl. No. 13/468,422; mailed Nov. 4, 2015; pp. 1-27.
Non-Final Rejection issued in U.S. Appl. No. 13/661,476; mailed Jun. 4, 2015, pp. 1-31.
Final Rejection issued in U.S. Appl. No. 13/661,476, mailed on Oct. 2, 2014, pp. 1-31.
Non-Final Rejection issued in U.S. Appl. No. 13/661,476, mailed on Mar. 6, 2014, pp. 1-28.
Non-Final Rejection issued in U.S. Appl. No. 13/661,476, mailed on Dec. 4, 2013, pp. 1-11.
Non-Final Rejection issued in U.S. Appl. No. 13/661,476, mailed on Sep. 16, 2013, pp. 1-19.
Non-Final Rejection issued in U.S. Appl. No. 13/692,640; mailed Oct. 31, 2013, pp. 1-10.
Non-Final Rejection issued in U.S. Appl. No. 13/692,640; mailed May 6, 2014, pp. 1-10.
Final Rejection issued in U.S. Appl. No. 13/692,640; mailed Jan. 6, 2015, pp. 1-11.
Final Rejection issued in U.S. Appl. No. 13/692,640; mailed Jun. 2, 2015, pp. 1-12.
Non-Final Rejection issued in U.S. Appl. No. 14/303,895; mailed Sep. 9, 2015, pp. 1-12.
Non-Final Rejection issued in U.S. Appl. No. 14/303,895; mailed May 21, 2015, pp. 1-11.
International Search Report by the ISA for International Application No. PCT/EP2007/005932; dated Oct. 9, 2007, pp. 1-6.
International Search Report by the ISA for International Application No. PCT/EP2009/000017; dated Jun. 22, 2009, pp. 1-7.
International Search Report by the ISA for International Application No. PCT/EP2009/063195; dated May 6, 2010.
International Search Report by the ISA for International Application No. PCT/EP2010/059436; dated Jun. 17, 2011, pp. 1-5.
International Search Report by the ISA for International Application No. PCT/EP2010/059438; dated Oct. 4, 2010, pp. 1-3.
International Search Report by the ISA for International Application No. PCT/EP2010/062638; dated Mar. 18, 2011, pp. 1-5.
International Search Report by the ISA for International Application No. PCT/EP2010/067250; dated Mar. 23, 2011, pp. 1-3.
International Search Report by the ISA for International Application No. PCT/EP2011/058079; dated Mar. 22, 2012, pp. 1-6.
International Search Report by the ISA for International Application No. PCT/EP2011/058764; dated Jun. 30, 2011, pp. 1-9.
International Search Report by the ISA for International Application No. PCT/EP2012/051670; dated Mar. 26, 2012, pp. 1-16.
International Search Report by the ISA for International Application No. PCT/EP2012/055660; dated May 10, 2012, pp. 1-6.
International Search Report by the ISA for International Application No. PCT/EP2012/058745; dated Jul. 12, 2012, pp. 1-6.
International Search Report by the ISA for International Application No. PCT/EP2012/058747; dated Jul. 8, 2012, pp. 1-6.
International Search Report by the ISA for International Application No. PCT/EP2012/058749; dated Jul. 31, 2012, pp. 1-6.
International Search Report by the ISA for International Application No. PCT/EP2012/058779; dated Aug. 28, 2012, pp. 1-5.
International Search Report by the ISA for International Application No. PCT/EP2012/066617; dated Nov. 22, 2012, pp. 1-5.
International Search Report by the ISA for International Application No. PCT/EP2012/069485; dated Dec. 11, 2012, pp. 1-5.
International Search Report by the ISA for International Application No. PCT/EP2012/069483; dated Nov. 29, 2011, pp. 1-4.
International Search Report by the ISA for International Application No. PCT/EP2012/071271; dated Jan. 30, 2013, pp. 1-5.
International Search Report by the ISA for International Application No. PCT/EP2012/074150; dated Nov. 20, 2012, pp. 1-4.
International Search Report by the ISA for International Application No. PCT/EP2014/062418; dated Sep. 22, 2014, pp. 1-4.
International Search Report by the ISA for International Application No. PCT/EP2014/051976; dated Mar. 4, 2014, pp. 1-3.
International Search Report by the ISA for International Application No. PCT/EP2014/056498; dated Jun. 25, 2014, pp. 1-10.
Written Opinion of the ISA for International Application No. PCT/EP2011/058079, mailed Mar. 22, 2012, pp. 1-8.
Extended European Search Report for Euorpean Application No. 98 11 0889.7; dated Oct. 14, 1998, pp. 1-4.
Extended European Search Report for European Application No. 09 17 5876.3; dated Mar. 24, 2010, pp. 1-4.
Extended European Search Report for European Application No. 09 17 5877.1; dated Apr. 29, 2010, pp. 1-5.
Extended European Search Report for European Application No. 10 16 4368.2; dated Oct. 14, 2010, pp. 1-6.
Extended European Search Report for European Application No. 10 30 5780; dated Nov. 16, 2010, pp. 1-3.
Extended European Search Report for European Application No. 11 15 3106; dated Jul. 6, 2011, pp. 1-12.
Extended European Search Report for European Application No. 11 16 0270.2; dated Sep. 19, 2011, pp. 1-8.
Extended European Search Report for European Application No. 11 16 6415; dated Mar. 12, 2012, pp. 1-12.
Extended European Search Report for European Application No. 11 17 9149.7; dated Feb. 9, 2012, pp. 1-8.
Extended European Search Report for European Application No. 13 305 126; dated Apr. 11, 2013, pp. 1-7.
Extended European Search Report for European Application No. 13 305 432.0; dated Sep. 13, 2013, pp. 1-5.
Extended European Search Report for European Application No. 14 16 6877.2; of Aug. 18, 2014, pp. 1-6.
Extended European Search Report for European Application No. 14 19 7154.9: dated Apr. 8, 2015, pp. 1-7.
English translation of Search Report for Chinese Patent Application No. 20140220537.9; dated Feb. 13, 2015, pp. 1-2.
English translation of Search Report for Chinese Patent Application No. 201280053404.6; dated Feb. 10, 2015, pp. 1-3.
http://diabetes.emedtv.com/lantus/generic-lantus.html; one page, last accessed Dec. 23, 2015.
18th World Health Congress (Helsinki). WMA Declaration of Helsinki—Ethical Principles for Medical Research Involving Human Subjects; WMA; Jun. 1964, pp. 1-8.
Action to Control Cardiovascular Risk in Diabetes Study Group, "Effects of intensive glucose lowering in type 2 diabetes." N Engl J. Med. 358(24):2545-59 (2008).
American Diabetes Association (ADA) Committee Report—The Expert Committee On The Diagnosis And Classification Of Diabetes Mellitus—Report of the Expert Committee on the Diagnosis and Classification of Diabetes Mellitus, Diabetes Care, 21(Supplement 1): S5-S19 (Jan. 1998).
Akbar, "Sub-Optimal postprandial blood glucose level in diabetics attending the outpatient clinic of a University Hospital" Saudi Med Journal, 24(10):1109-1112 (Oct. 2003).
Ahren et al., Abstract "Efficacy and Safety of Lixisenatide QD Morning and Evening Injections vs Placebo in T2DM Inadequately Controlled on Metformin (GetGoal-M)" Oral presentation O-0591 presented at the World Diabetes congress in Dubai, Dec. 5-8, 2011, one page.
Aoki et al., Hydrolysis of Nonionic Surfactants, Ann. Rept. Takeda Res. Lab. 27, 172-176 (1968).
Arnolds et al., "Further improvement in postprandial glucose control with addition of exenatide or sitagliptin to combination therapy with insulin glargine and metformin—a proof-of-concept study" Diabetes Care 33(7):1509-15 (2010).
Arnolds et al., "Insulin Glargine (GLAR) plus Metformin (MET): An Efficacious and Safe Regimen that can be combined with Exenatide (EXE) or Sitagliptin (SITA)" Diabetes, 58(Suppl. 1): A141, Jun. 2009.
Arnolds & Rave, "Basal insulin glargine vs prandial insulin lispro in type 2 diabetes," Lancet 378(9636):370-71 (2008).

(56) References Cited

OTHER PUBLICATIONS

Auerbach et al., "Angiogenesis assays: Problems and Pitfalls," Cancer and Metastasis Reviews, 19:167-72 (2000).
Bakaysa et al., "Physicochemical basis for the rapid time-action of Lys.sup.B28 and Pro.sup.B29-insulin: Dissociation of a protein-ligand complex," Protein Science 5:2521-31 (1996).
Barnett & Owens, "Insulin Analogues," Lancet 349(9044):47-51 (1997).
Barnett et al., "Tolerability and efficacy of exenatide and titrated insulin glargine in adult patients with type 2 diabetes previously uncontrolled with metformin or a sulfonylurea: a multinational, randomized, open-label, two-period, crossover noninferiority trial." Clinical Therapeutics 29(11)2333-48 (Nov. 2007).
Barnett "Lixisenatide: evidence for its potential use in the treatment of type 2 diabetes." Core Evidence 6:67-79 (published online Sep. 8, 2011).
Barnett, "Insulin glargine in the treatment of type 1 and type 2 diabetes" Vascular Health and Risk Management 2:59-67 (published Jan. 25, 2006).
Barnett, "Dosing of Insulin Glargine in the Treatmetnt of Type 2 Diabetes," Clinical Ther. 29(6):987-99 (Jun. 2007).
Behar et al. "Functional gallbladder and sphincter of oddi disorders." Gastroenterology 130(5):1498-1509 (2006).
Beintema & Campagne, "Molecular Evolution of Rodent Insulins," Mol. Biol. Evol. 4(1): 10-18, 1987.
Berger "Towards more physiological insulin therapy in the 1990s—A comment," Diabetes Research and Clinical Practice, 6(4): S25-31 (May 1989).
Berlie et al., "Glucagon-like peptide-1 receptor agonists as add-on therapy to basal insulin in patients with type 2 diabetes: a systematic review." Diabetes, Metabolic Syndrome and Obesity: Targets and Therapy 5:165-74 (2012).
Bethel & Feinglos, "Basal insulin therapy in type 2 diabetes." J Am Board Fam Pract. 18(3):199-204 (May-Jun. 2005).
Bhatt et al., "Chemical pathways of peptide degradation. I. Deamidation of adrenocorticotropic hormone," Pharm Res. 7(6):593-9 (1990).
Bland and Altman, "Measurement error" BMJ 312:1654 (Jun. 29, 1996).
Best, Mathmatics and Statistics pp. 1-39, 1988.
Bolen et al., "Systematic Review: Comparative Effectiveness and Safety of Oral Medications for Type 2 Diabetes Mellitus," Ann. Intern. Med. 147:386-399 (Epub Jul. 16, 2007).
Bolli et al., "Efficacy and safety of lixisenatide once-daily versus placebo in patients with type 2 diabetes mellitus insufficiently controlled on metformin (GetGoal-F1)." Presentation Abstract No. 784, EASD Meeting Sep. 12-16, 2014.
Bolli et al., "Efficacy and safety of lixisenatide once daily vs. placebo in people with Type 2 diabetes insufficiently controlled on metformin (GetGoal-F1)." Diabetic Medicine 31:176-184 (published online Oct. 24, 2013).
Bolli "The pharmacokinetic basis of insulin therapy in diabetes mellitus," Diabetes Research and Clinical Practice, 6(4):S3-15 (May 1989).
Brange, "Design of Insulin Analogues for Meal-Related Therapy", J. Diabetes Complications 7(2):106-112 (Apr.-Jun. 1993). Abstract only.
Brange et al., "Toward Understanding Insulin Fibrillation," Journal of Pharmaceutical Sciences , 86(5):517-25 (1997).
Brange & Langkjaer, "Chemical stability of insulin 3. Influence of excipients, formulation, and pH," Acta Pharma. Nord. 4(3):149-58 (1992).
Brange et al., "Monomeric insulins and their experimental and clinical implications," Diabetes Care 13(9):923-45 (Sep. 1990).
Brange et al., "Neutral insulin solutions physically stabilized by addition of Zn2+," Diabetic Medicine 3:532-6 (Nov.-Dec. 1986).
Brange "Galenics of Insulin" 1987, p. 35-36.
Brange & Langkjaer, "Insulin Structure and Stability" Chapter 11; Pharm Biotechnol 5:315-50 (1993).
Brod et al., "Adherence patterns in patients with type 2 diabetes on basal insulin analogues: missed, mistimed and reduced doses." Curr Med Res Opin. 28(12):1933-46 (2012).
Brod et al., "Examining correlates of treatment satisfaction for injectable insulin in type 2 diabetes: lessons learned from a clinical trial comparing biphasic and basal analogues." Health Quality of Life Outcomes. 5:8 (2007), pp. 1-10.
Brown & Nichols, "Slow response to loss of glycemic control in type 2 diabetes mellitus." Am J Manag Care. 9 (3):213-17 (2003).
"Buffer" Oxford Dictionary of Biochemistry and Molecular Biology, Oxford University Press, 2001, p. 83.
Burgermeister et al. "The Isolation of Insuin from the Pancreas," Insulin, Part 2, 1975, p. 715-727.
Burke et al., "Nature of the B10 amino acid residue," Int. J. Peptide Protein Res., 23(4):394-401 (Apr. 1984).
Buse et al., "Use of twice-daily exenatide in Basal insulin-treated patients with type 2 diabetes: a randomized, controlled trial." Annals of Internal Medicine 154(2):103-12 (Jan. 2011).
Byetta—Summary of Product Characteristics, updated Jan. 27, 2015, last accessed Apr. 18, 2015, pp. 1-12.
Byrne et al., "Inhibitory Effects of Hyperglycaemia on Fed Jejunal Motility: Potential Role of Hyperinsulinaemia," Euro. J. Clin. Invest. 28(1):72-78 (1998).
Cadario, "Sitagliptin" Drug Information Perspectives, 30(4):1-6 (2010).
Campbell et al., "Insulin Glargine," Clin. Therapeutics 23(12):1938-57 (2001).
Chancel, "Natixis Conference on Diabetes." Sanofi, Paris, pp. 1-23 (Nov. 8, 2011).
Chatterjee et al., "Insulin glargine and its place in the treatment of Types 1 and 2 diabetes mellitus." Expert Opin Pharmacother 7(10):1357-71 (2006).
Charles et al., "Prevention of Type 2 Diabetes Role of Metformin" Review Article, Drugs 1999; 58 Suppl. 1:71-73 (Sep. 1999).
Chen et al., "Tissue-specific Expression of Unique mRNAs That Encode Proglucagon-derived Peptides or Exendin 4 in the Lizard," J. Biol. Chem. 272(7):4108-15 (1997).
Childs et al., "Defining and Reporting Hypoglycemia in Diabetes," Diabetes Care 28(5):1245-9 (May 2005).
Cholangiocarcinoma, Johns Hopkins Medicine Webstite, https://gi.jhsps.org/GDL Disease.aspx?CurrentUDV=31&GDLCat_ID=AF793A59-B736-42CB-9E1FE79D2B9FC358&GDL_Disease_ID=A6D1OE80-887D-49A7-B3BB-0517D38CE757, accessed on May 14, 2014, pp. 1-12.
Christensen et al., "Lixisenatide for type 2 diabetes mellitus," Expert Opin. 20(4):549-57 (Epub Mar. 11, 2011).
Cochran et al., "The Use of U-500 in Patients with Extreme Insulin Resistance" Diabetes Care, 28(5):1240-44 (2005).
Lyxumia, Chemical Subgroup A10BX, Community Register of Medicinal Products for Human Use, Eurpean Commission Public Health, p. 1-2 (May 2, 2013).
Colclough et al., Abstract "Levels of FPG and HbA1c Control and the Relationship to BMI in T2D Patients Treated with Basal Insulin and OAD Therapy." Abstract 2416-PO; Presented at the 72nd Scientific Session at the American Diabetes Association Meeting, 2012, A609, one page.
Colino et al., "Therapy with insulin glargine (Lantus) in toddlers, children and adolescents with type 1 diabetes," Diabetes Research and Clinical Practice (2005), vol. 70, pp. 1-7.
Correa, "Pautas para el examen de patentes farmaceuticas. Una perspectiva desde la Salud Publica. Documento le Trabajo" Universidad de Buenos Aires, Mar. 2008, see pp. 19-20, pp. 1-66.
Craig et al., "ISPAD Clinical Practice Consensus Guidelines 2014 Compendium—Definition, epidemiology, and classification of diabetes in children and adolescents." Pediatric Diabetes, 15(Suppl. 20):4-17 (2014).
Crapo et al., "Postprandial plasma-glucose and -insulin responses to different complex carbohydrates," Diabetes 26 (12):1178-83 (Dec. 1977).
Croom et al., "Liraglutide A Review of its Use in Type 2 Diabetes Mellitus," Drugs, 69(14):1985-2004 (2009).
Cryer "Hypoglycemia is the limiting factor in the management of diabetes," Diabetes Metab. Res. Rev. 15(1):42-46 (Jan.-Feb. 1999).

(56) References Cited

OTHER PUBLICATIONS

Cvetkovic et al., "Exenatide A Review of Its Use in Patients with Type 2 Diabetes Mellitus (as an Adjunct to Metformin and/or a Sulfonylurea)," Drugs, 67(6):935-54 (2007).
D'Alessio et al., "Glucagon-like Peptide 1 Enhances Glucose Tolerance Both by Stimulation of Insulin Release and by Increasing Insulin-independent Glucose Disposal," J. Clin. Invest. 93(5):2263-66 (1994).
D'Alessio et al., "GLP-1 Receptor Agonists: Strategies for PPG Control," Medical Nursing Edu., 3:1-26 (Jan. 2011).
Database, ADISCTI, "A randomized, 4-sequence, cross-over, double bind, dose response study of 0.4, 0.6 and 0.09 U/kg insluin glarine U300 compared to 0.4 U/kg Lantus U100 in patients with diabetes mellitus type I using euglycemic clamp technique" last updated Dec. 16, 2010, pp. 1-4.
Davis How to Convert mg to mmol/L, available online at http://www.ehow.com/how_8498850_convert mg-mmoll.html (accessed on Nov. 11, 2015).
Deacon et al., "Dipeptidyl Peptidase IV Inhibition Potentiates the Insulinotropic Effect of Glucagon-Like Peptide 1 in the Anesthetized Pig," Diabetes 47(5):764-69 (1998).
Deacon et al., "Dipeptidyl Peptidase IV Resistant Analogues of Glucagon-Like Peptide-1 Which Have Extended Metabolic Stability and Improved Biological Activity," Diabetologia 41(3):271-78 (1998).
Definition of palliative, http://medicaldictionary.thefreedictionary.com/, accessed on Nov. 6, 2014, pp. 1-2.
Definition of sphincter of pancreatic duct in the Medical Dictionary, http://medicaldictionary.thefreedictionary.com/, accessed on May 22, 2014, pp. 1-2.
Definition of indication, Merriam-Webster online, accessed Oct. 22, 2015, 2 pages.
DeFronzo "Effects of Exenatide (Exendin-4) on Glycemic Control and Weight Over 30 Weeks in Metformin-Treated Patients with Type 2 Diabetes", Diabetes Care 28(5):1092-1100 (May 2005).
DeFronzo "Pathogenesis of Type 2 Diabetes Implications for Metformin" Short Communication, Drugs 1999; 58(Suppl 1):29-30 (Sep. 1999).
DeFronzo "Pharmacologic Therapy for Type 2 Diabetes Mellitus." Ann Int Med. 131:281-303 (1999).
De Le Pena, "Pharmacokinetics and Pharmadynamics of High-Dose Human Regular U-500 Insulin Versus Human Regular U-100 Insulin in Healthy Obese Subjects" Diabetes Care, 34(12):2496-501 (2011).
DeWitt, "Case Study: Treating New On-Set Catabolic Type 2 Diabetes with Glargine and Lispro", Clinical Diabetes vol. 24, No. 4, pp. 180-181,(Oct. 2006).
deVries et al., "Sequential intensification of metformin treatment in type 2 diabetes with liraglutide followed by randomized addition of basal insulin prompted by A1C targets." Diabetes Care 35:1446-54 (2012).
Diabetes Prevention Program Research Group. "Reduction in the incidence of type 2 diabetes with lifestyle intervention or metformin." N Engl J. Med. 346(6):393-403 (2002).
Distiller et al., Poster: "Pharmacokinetics and Pharmacodynamics of a New GLP-1 Agonist AVE0010 in Type 2 Diabetes Patients" Meeting: 68th Scientific Sessions (Jun. 2008) Poster No. 520-P.
Dixon et al., "Regeneration of Insulin Activity From the Separated and Inactive A and B Chains," Nature, vol. 188, No. 4752 (1960), pp. 721-724.
Donelli, "Plastic Biliary Stent Occlusion: Factors Involved and Possible Preventive Approaches," Clinical Medicine & Research 5(1):53-60 (Mar. 2007).7.
Dormandy et al., "Secondary prevention of macrovascular events in patients with type 2 diabetes in the PROactive Study (PROspective pioglitAzone Clinical Trial in macrovascular Events): a randomised controlled trial," Lancet. 366 (9493):1279-89 (Oct. 8, 2005).
Drury et al., "Diabetic nephropathy," British Medical Bulletin, vol. 45, No. 1, 1989, pp. 127-147.
Drucker, "The Biology of Incretin Hormones," Cell Metab. 3(3):153-65 (2006).
Drucker, "Glucagon-Like Peptides," Diabetes 47(2):159-69 (1998).
Drucker, "Mini review: The Glucagon-Like Peptides," Endocrinology 142(2):521-27 (2001).
DrugBank, "Insulin glargine," available online at http://www.drugbank.ca/drugs/DB00047, 16 pages (accessed online Sep. 25, 2014).
Dunn et al., "Insulin Glargine: An Updated Review of its Use in the Management of Diabetes Mellitus" Drugs 63 (16):1743-1778 (2003).
Eng et al., "Isolation and characterization of exendin-4, an exendin-3 analogue, from Heloderma suspectum venom. Further evidence for an exendin receptor on dispersed acini from guinea pig pancreas," J Biol Chem 267(11):7402-5 (1992).
EMA Press Release, "European Medicines Agency recommends suspension of Avandia, Avandamet and Avaglim" pp. 1-2 (Sep. 23, 2010).
European Medicines Agency—Science Medicines Health, "Guideline on clinical investigation of medicinal products in the treatment of diabetes mellitus" Committee for Medicinal Products for Human Use, Jan. 20, 2010, pp. 1-19.
Executive Summary, "Standards of Medical Care in Diabetes—2009" Diabetes Care,32(Suppl. 1):S6-S12 (Jan. 2009).
Ex Parte Herrmann, Appeal No. 2009-001777 U.S. Appl. No. 10/616,457 (B. PAI. Nov. 13, 2009).
Fabunmi et al., "Patient characteristics, drug adherence patterns, and hypoglycemia costs for patients with type 2 diabetes mellitus newly initiated on exenatide or insulin glargine." Curr Med Res Opin. 25(3):777-86 (2009).
FDA Guidance for Industry, US Department of Health and Human Services, Food and Drug Administration, Center for Drug Evaluation and Research (COER), pp. 1-11, Feb. 2014.
FDA Frequently Asked Questions about Combination Products; accessed from www.fda.gov/CombinationProducts/AboutCombinationProducts/usm101496.1/htm, 2009 downloaded Jul. 13, 2012, pp. 1-18.
FDA label of Apidra®, May 2014, pp. 1-35.
FDA label of Humalog®, Mar. 2013, pp. 1-27.
FDA label of Lantus®, Oct. 2013, pp. 1-44.
Feinglos et al., "Effects of liraglutide (NN2211), a long-acting GLP-1 analogue, on glycaemic control and bodyweight in subjects with type 2 diabetes." Diabetic Medicine, 22(8):1016-23 (Jul. 2005).
Actrapid® summary of product characteristics, Apr. 2011, pp. 1-11.
Actrapid® prescribing information, Apr. 2011, pp. 1-4.
Apidra® prescribing information, Apr. 2012, pp. 1-6.
Berlinsuline® H summary of product characteristics, Apr. 2012, pp. 1-11.
Berlinsuline® H prescribing information, Apr. 2012, pp. 1-4.
Humalog® prescribing information, Apr. 2012, pp. 1-6.
Insuman® Comb25 prescribing information, Feb. 2011, pp. 1-4.
Insuman® Infusat prescribing information, Feb. 2011, pp. 1-4.
Lantus® prescribing information, May 2012, pp. 1-6.
Levemir® prescribing information, Dec. 2011, pp. 1-6.
Novolog® product information, Oct. 2009, pp. 1-4.
NovoMix® prescribing information, Feb. 2011, pp. 1-5.
NovoRapid® prescribing infonnation, Jul. 2012, pp. 1-5.
Fieller, Symposium on Interval Estimation; "Some Problems with Interval Estimation" Journal of the Royal Statistical Society 16(2):175-85 (1954).
Fonseca et al., "Efficacy and Safety of the Once-Daily GLP-1 Receptor Agonist Lixisenatide in Monotherapy" Diabetes Care, 35:1225-31 (Jun. 2012).
Fox et al., Protein Science 10: 622-30 (2001).
Fransson et al., "Oxidation of Human Insulin-Like Growth Factor I in Formulation Studies: Kinetics of Methionine Oxidation in Aqueous Solution and in Solid State" Pharmaceutical Research 13(8):1252-57 (Aug. 1996).
Galloway & Root, "New forms of insulin," Diabetes 21 (2 Suppl):637-48 (1972).
Gallwitz, "Liraglutide. GLP-1 Receptor Agonist Treatment of Type 2 Diabetes Treatment of Obesity," Drugs of the Future, 33(1):13-20 (Jan. 2008).

(56) References Cited

OTHER PUBLICATIONS

Garber et al., "Liraglutide versus glimepiride monotherapy for type 2 diabetes (LEAD-3 Mono): a randomised, 52-week, phase III, double blind, parallel-treatment trial", The Lancet, 373(9662):473-81 (Feb. 7, 2009).
Garg, R., et al., "U-500 insulin: why, when and how to use in clinical practice", Diabetes/Metabolism Research and Reviews, 23:265-268 (2007).
Garriques et al., "The Effect of Mutations on the Structure of Insulin Fibrils Studied by Fourier Transform Infrared (FTIR) Spectroscopy and Electron Microscopy," Journal of Pharmaceutical Sciences, 91(12):2473-80 (2002).
Gavin—Committee Report, "Report of the Expert Committee on the Diagnosis and Classification of Diabetes Mellitus," Diabetes Care, 20(7):1183-97 (Jul. 1997).
Geiger, Chem. Zeitung, 100(3), p. 54-56. (Jan. 1976).
Gerich et al., "Monotherapy with GLP-1 receptor agonist, Lixisenatide, significantly improves glycaemic control in type 2 diabetic patients," Presentation abstract 830, 46th Annual Meeting of EASD, Stockholm, Sweden, pp. 1-3 (Sep. 2010).
Giugliano et al., "Treatment regimens with insulin analogues and haemoglobin A1c target of <7% in type 2 diabetes: A systematic review." Diabetes Research and Clinical Practice 92(1):1-10 (2010).
Goke et al., "Distribution of GLP-1 Binding Sites in the Rat Brain: Evidence that Exendin-4 is a Ligand of Brain GLP-1 Binding Sites," Eur. J. Neurosci. 7(11):2294-2300 (1995).
Goke et al., "Exendin-4 is a High Potency Agonist and Truncated Exendin-(9-39)-amide an Antagonist at the Glucagon-like Peptide 1-(7-36)-amide Receptor of Insulin-secreting beta-Cells," J. Biol. Chem. 268:19650-55 (1993).
Goldstein et al. Tests of Glycemia in Diabetes. Diabetes Care 18(6):896-909 (Jun. 1995).
Gough, K. et al.; Assessment of Dose Proportionality: Report from the Statisticians in the Pharmaceutical Industry/Pharmacokinetics UK Joint Working Party; Drug Information Journal, vol. 29, 1995, pp. 1039-1048.
Goykhman et al., "Insulin Glargine: a review 8 years after its introduction." Expert Opin. Pharmacother. 10(4):705-18 (2009).
Greig et al., "Once Daily Injection of Exendin-4 to Diabetic Mice Achieves Long-Term Beneficial Effects on Blood Glucose Concentrations." Diabetologia 42(1):45-50 (1999).
Gura, "Systems for Identifying New Drugs are Often Faulty," Science, 278(5340):1041-042 (1997).
Gutniak et al., "Antidiabetogenic Effect of Glucagon-Like Peptide-1 (7-36) Amide in Normal Subjects and Patients with Diabetes Mellitus," N. Engl. J. Med. 326:1316-1322 (1992).
Hanas et al., "2010 Consensus Statement on the Worldwide Standardization of the Hemoglobin A1C Measurement." Diabetes Care 33(8):1903-04 (Aug. 2010).
Hanefeld & Temelkova-Kurktschiev, "The postprandial state and the risk of atherosclerosis." Diabet Med. 14 Suppl 3:S6-11 (1997).
Hanefeld M. Normnahe postprandiale Hyperglykamie-eine essenzielle Komponente guter Diabeteskontrolle und Pravention kardiovaskularer Erkrankungen (Near-normal postprandial hyperglycemia—an essential component of good diabetes control and prevention of cardiovascular diseases). Paul Langerhans lecture 2007. Diabetologie und Stoffwechsel 2007; 2:362-369. In German with English abstract.
Hanna et al., Canadian Diabetes Association Clinical Practice Guidelines Expert Committee "Pharmacologic Management of Type 2 Diabetes" Canadian Journal of Diabetes, 27(Supp 2):S37-S42 (Dec. 2003).
Harris "Clinical inertia in patients with T2DM requiring insulin in family practice." Can Fam Physician.56(12):e418-e424 (2010).
Hartmann et al., "Biological Activity of des-(B26-B30)-Insulinamide and Related Analogues in Rat Hepatocyte Cultures," Diabetologia 32(7):416-20 (1989).
Heinrich et al., "Pre-proglucagon messenger ribonucleic acid: nucleotide and encoded amino acid sequences of the rat pancreatic complementary deoxyribonucleic acid," Endocrinol. 115(6):2176-81 (1984).
Hellstrom et al., "T1388 GTP-010 As a Therapetuic Tool in IBS Pain Relief: Prospective, Randomized, Palebo-Controlled Study of a GLP-1 Analog", Gastroenterology, 134(4):A-544; Absract T1388 (Apr. 2008).
Hinds et al., "Synthesis and characterization of poly(ethylene glycol)-insulin conjugates." Bioconjugate Chem. 11(2):195-201 (Mar.-Apr. 2000).
HOE 901/2004 Study Investigators Group, "Safety and efficacy of insulin glargine (HOE 901) versus NPH insulin in combination with oral treatment in Type 2 diabetic patients," Diabetic Medicine (2003), vol. 20, pp. 545-551, XP002671079.
Holst & Vilsboll. "Combining GLP-1 receptor agonists with insulin: therapeutic rationales and clinical findings." Diabetes, Obesity and Metabolism 15(1):3-14 (2013).
Home et al., "Insulin treatment: a decade of change," British Medical Bulletin, 1989, vol. 45, No. 1, pp. 92-110.
Holman et al., "10-Year Follow-up of Intensive Glucose Control in Type 2 Diabetes." N. Engl J. Med. 359(15):1577-89 (2008).
Inpharma, Product News. "AVE0010 set to deliver in type 2 diabetes mellitus," Database Adisnews, retrieved from STN, Jun. 2008, pp. 1-3.
Insulinpraparat Wikipedia, http://de.wikipedia.org/wiki/Insulinpr%C3%A4parat, pp. 1-15 (Feb. 5, 2013).
"Insulin Aspart Injection." Formulated Preparations: Specific Monographs. British Pharmacopoeia 3. pp. 1-3 (2012).
Inzucchi et al. "Management of Hyperglycemia in Type 2 Diabetes: A Patient-Centered Approach" Diabetes Care, 35:1364-79 (Jun. 2012).
ISPAD, International Diabetes Federation; "Global/IDF/ISPAD Guideline for Diabetes in Childhood and Adolescence," pp. 1-132 (2011).
Jackson et al., "Neutral regular insulin," Diabetes 21(4):235-45 (1972).
Jain, "Barriers to Drug Delivery in Solid Tumors," Scientific American, 271(1):58-65 (Jul. 1994).
Jekel et al., "Use of endoproteinase Lys-C from Lysobacter enzymogenes in protein sequence analysis," Anal Biochem. 134(2):347-54 (1983).
Jendle et al., "Insulin and GLP-1 analog combinations in type 2 diabetes mellitus: a critical review." Expert Opin. Investig. Drugs 21(10):1463-74 (2012).
Johnson et al., "When is a unit of insulin not a unit of insulin? Detemir dosing in type 2 diabetes" Poster, one page, 2008. http://professional.diabetes.org/ContenUPosters/2008/p8-LB.pdf.
Jorgensen et al., "Five fold increase of insulin concentration delays the absorption of subcutaneously injected human insulin suspension in pigs", Diabetes Research and Clinical Practice, 50:161-167 (2000).
Kaarsholm et al., "Engineering stability of the insulin monomer fold with application to structure-activity relationships," Biochemistry 32(40):10773-8 (1993).
Kadima "Role of Metal Ions in the T- to R-Allosteric Transition in the Insulin Hexamer," Biochem. 38(41):13443-53 (Oct. 1999).
Kahn et al., "Glycemic durability of rosiglitazone, metformin, or glyburide monotherapy." N Engl J. Med. 355 (23):2427-43 (2006).
Kakhki et al., "Normal values of gallbladder ejection fraction using 99 mTc-sestamibi scintigraphy after a fatty meal formula." J Gastrointestin Liver Dis. 16(2):157-61 (Jun. 2007).
Kamisawa. et al., "Pancreatographic investigation of pancreatic duct system and pancreaticobiliary malformation" J. Anal. 212(2):125-34 (2008).
Kanazawa et al., "Criteria and Classification of Obesity in Japan and Asia-Oceania", Asia Pacific J. Clin Nutr. 11 (Suppl. 7):S732-S737 (Dec. 2002).
Kang et al., "Subcutaneous Insulin Absorption Explained by Insulin's Physicochemical Properties-Evidence from Absorption Studies of Soluble Human Insulin and Insulin Analogues in Humans," Diabetes Care, 14(11):942-48 (Nov. 1991).

(56) References Cited

OTHER PUBLICATIONS

Kao et al., "The evaluation of gallbladder function by quantitative radionuclide cholescintigraphy in patients with noninsulin-dependent diabetes mellitus." Nucl. Med Commun.14(10):868-72 (1993).
Kapitza et al., Abstract "Pharmacodynamic Characteristics of Lixisenatide QD vs Liraglutide QD in Patients with T2DM Inadequately Controlled with Metformin" Abtract D-0740, presented at the World Diabetes Congress in Dubai, Dec. 5-8, 2011, one page.
Kemmler et al., "Studies on the Conversion of Proinsulin to Insulin," The Journal of Biological Chemistry, 246 (22):6786-91 (1971).
Kendall et al., "Effets of Exenatide (Exendin-4) on Glycemic Control Over 30 Weeks in Patients With Type 2 Diabetes Treated With Mefformin and a Sulfonylurea" Diabetes Care 28:1083-91 (May 2005).
Kielgast et al., "Treatment of type 1 diabetic patients with glucagon-like peptide-1 (GLP-1) and GLP-1R agonists." Curr Diabetes Rev. 5(4):266-75 (Nov. 2009).
Kohner "Diabetic retinopathy," British Medical Bulletin, vol. 45, No. 1, 1989, pp. 148-173.
Knee et al., "A Novel Use of U-500 Insulin for Continuous Subcutaneous Insulin Infusion in Patients with Insulin Resistance: A Case Series", Endocrine Practice, 9(3):181-86 (May/Jun. 2003).
Knudsen et al., "Potent Derivatives of Glucagon-Like Peptide-1 With Pharmacokinetic Properties Suitable for Once Daily Administration", J. Med. Chem. 43(9):1664-69 (2000).
Kohn et al., "pi-shifted insulin analogs with extended in vivo time action and favorable receptor selectivity," Peptide 28:935-48 (2007).
Kolterman et al., "Synthetic Exendin-4 (Exenatide) Significantly Reduces Postprandial and Fasting Plasma Glucose in Subjects with Type 2 Diabetes," J. Clin. Endocrine. Metab. 88(7):3082-89 (2003).
Krishnamurthy et al., Constancy and variability of gallbladder ejection fraction: impact on diagnosis and therapy. J Nucl Med. 45(11):1872-77 (Nov. 2004).
Lando, "The New 'Designer' Insulins", Clinical Diabetes, 18(4): Fall 2000 (http://journal.diabetes.org/clinicaldiabelesN18N42000/pg154.hlm; accessed Oct. 22, 2013, pp. 1-13).
Lantus® Annex I—Summary of product characteristics. Date of first authorisation: Jun. 9, 2000, pp. 1-164.
Lantus® Product Information—European Medicines Agency, first published Aug. 5, 2009, pp. 1-2.
Larsen et al., "Sequence-Assisted Peptide Synthesis (SAPS)," J. Pept. Res. 52(6):470-76 (1998).
Larsen et al., "Combination of the insulin sensitizer, pioglitazone, and the long-acting GLP-1 human analog, liraglutide, exerts potent synergistic glucose-lowering efficacy in severely diabetic ZDF rats," Diabetes, Obesity and Metabolism, 10:301-311 (2008).
Leib et al., "Direct quantitation of peptide mixtures without standards using clusters formed by electrospray ionization mass spectrometry." Anal Chem. 81(10):3965-72 (May 2009).
Lens, "The terminal carboxyl groups of insulin," Biochimica et Biophysica Acta 3:367-70 (1949).
Levene & Simms, "Calculation of isoelectric point," J Bioi Chern. 55:801-13 (1923).
Levin et al., "Combination therapy with insulin glargine and exenatide: real-world outcomes in patients with type 2 diabetes." Current Medical Research & Opinion 28(2):1-8 (2012).
Leyer et al., "The role of the C-terminus of the insulin B-chain in modulating structural and functional properties of the hormone," Int J Pep Protein Res. 46(5):397-407 (1995).
Levine et al., "Oxidation of Methionine in Proteins: Roles in Antioxidant Defense and Cellular Regulation" IUBMB Life, 50:301-07 (Oct. 2000).
Lill, "Production of fast-acting insulins and delayed-release insulins—how can this problem be solved by technology? Insulin formulations," Pharmazie in unserer Zeit 30(1):56-61 (2001). (English Translation Included).
"Lixisenatide, Chemical Structure CID 16139342, Pubchem, accessed Feb. 5, 2015 at URLpubchem.ncbi.nlm.nih.gov/summary/summary.cgi?sid=135267128&viewopt=Deposited, pp. 1-3."
Liu & Ruus, Abstract "Pharmacokinetics and Safety of the GLP-1 Agonist AVE0010 in Patients with Renal Impairment," Diabetes 58 (Suppl. 1): Abstract 557-P for the 69th Scientific Session of the American Diabetes Association Jun. 5-9, 2009, New Orleans, Louisiana, pp. 1-2.
Lougheed et al., "Physical Stability of Insulin Formulations," Diabetes, 32(5):424-32 (May 1983).
Lyxumia® Annex I—Summary of product characteristics. Date of first authorisation: Feb. 1, 2013, pp. 1-92.
Lyxumia® Product Information—European Medicines Agency, first published Mar. 14, 2013, pp. 1-2.
Lyxumia 10 micrograms solution for injection, Summary of Product Characteristics, updated Oct. 31, 2014, pp. 1-12.
Marbury, et al., "A Pilot Study to Examine the Feasability of Insulin Glargine in Subjects with Impaired Fasting Glucose, Impaired Glucose Tolerance or New-Onset Type 2 Diabetes", Experimental and Clinical Endocrinology & Diabetes: Official Journal, German Society of Endocrinology and German Diabetes Associate, 116(5)282-88 (May 2008).
Markussen et al., "Soluble, prolonged-acting insulin derivatives. II. Degree of protraction and crystallizability of insulins substituted in the termini of the B-chain," Prot. Eng. 1(3), 1987, pp. 205-213.
Markussen et al., "Soluble, prolonged-acting insulin derivatives. II. Degree of protraction and crystallizability of insulins substituted in positions A17, B8, B13, B27 and B30," Prot. Eng. 1(3), 1987, pp. 215-223.
Markussen et al., "Soluble, prolonged-acting insulin derivatives. III. Degree of protraction, crystallizability and chemical stability of insulins substituted in positions A21, B13, B23, B27 and B30," Prot. Eng. 2(2), 1988, pp. 157-166.
Mecklenburg & Guinn, "Complications of insulin pump therapy: the effect of insulin preparation," Diabetes Care 8 (4):367-70 (1985).
Medline Plus, "Obesity" available at http://www.nlm.nih.gov/medlineplus/obesity.html, Retrieved Aug. 22, 2013, one page.
Meier, "GLP-1 receptor agonists for individualized treatment of type 2 diabetes mellitus." Nat. Rev. Endocrinol. 8:728-42 (2012).
Merrifield, "Solid Phase Synthesis." Science 232(4748):341-47 (1986).
Mikhail, "Is liraglutide a useful addition to diabetes therapy?" Endocr Practice 16(6):1028-37 (Nov.-Dec. 2010).
Monnier et al., The loss of postprandial glycemic control precedes stepwise deterioration of fasting with worsening diabetes. Diabetes Care. 30(2):263-69 (2007).
Moretto et al., "Efficacy and Tolerability of Exenatide Monotherapy Over 24 Weeks in Antidiabetic Drug-Naive Patients with Type 2 Diabetes: A Randomized, Double-Blind, Placebo-Controlled, Parallel-Group Study", Clinical Therapeutics, 30(8):1448-60 (Aug. 2008).
Muller et al., "Insulin Signaling in the Yeast Saccharomyces cerevisiae. 1. Stimulation of Glucose Metabolism and Snf 1 Kinase by Human Insulin," Biochemistry, 37(24):8683-95 (Jun. 1998).
Muzaffar et al., "The Mechanism of Enhanced Insulin Amyloid Fibril Formation by NaCIIs Better Explained by a Conformational Change Model," PLoS One, Nov. 21, 2011, pp. 1-11, 6(11):e27906.
Nathan et al., "Insulinotropic Action of Glucagon like Peptide-1-(7-37) in Diabetic and Nondiabetic Subjects," Diabetes Care 15(2):270-76 (1992).
Nathan et al., "Management of hyperglycaemia in type 2 diabetes mellitus: a consensus algorithm for the initiation and adjustment of therapy. Update regarding the thiazolidinediones." Diabetologia. 51(1):8-11 (2008).
Nauck et al., "Effects of Subcutaneous Glucagon-Like Peptide 1 (GLP-1 [7-36 Amide]) in Patients with NIDDM," Diabetologia 39(12):1546-53 (1996).
Nauck et al., "Glucagon-Like Peptide 1 and its Potential in the Treatment of Non-Insulin-Dependent Diaetes Mellitus," Horm. Metab. Res. 29(9):411-16 (1997).
Nauck et al., "Comparative evaluation of incretin-based antidiabetic medications and alternative therapies to be added to melformin in the case of monotherapy failure," Journal of Diabetes Investigation 1(1-2):24-36 (Feb.-Apr. 2010).
NCT00715624 Clinical Trials.gov "GLP-1 Receptor Agonist Lixisenatide in Patients With Type 2 Diabetes for Glycemic Control and Safety Evaluation, on Top of Basal Insulin (GETGOAL-L)" (2008-2014), p. 1-6 (Feb. 2011).

(56) References Cited

OTHER PUBLICATIONS

NCT00976937, ClinicalTrials.gov, "24-week Study Comparing Lixisenatide (AVE0010) to Sitagliptin as add-on to Metformin in Obese Type 2 Diabetic Patients Younger than 50," May 6, 2011, Retrieved Nov. 7, 2011, pp. 1-4.
NCT00299871, ClinicalTrials.gov, "Dose Ranging Study of the GLP-1 Agonist AVE0010 in Metformin-Treated Subjects With Type 2 Diabetes Mellitus," Jun. 22, 2010, Retrieved Nov. 7, 2011, pp. 1-5.
NCT00712673, Clinical Trials.gov, "GLP-A Agonist AVE0010 (Morning or Evening) in Patients with Type 2 Diabetes for Glycemic Control and Safety Evaluation, on Top of Metformin", Mar. 22, 2011, pp. 1-4.
NCT00975286, Clinical Trials.gov, "24-week Treatment with Lixisenalide in Type 2 Diabetes Insufficiently Controlled With Melformin and Insulin Glargine", Aug. 8, 2011, pp. 1-4.
NCT00688701 Clinical Trials.gov "GLP-1 Receptor Agonist Lixisenatide in Patients with Type 2 Diabetes for Glycemic Control and Safety Evaluation in Monotherapy (GETGOAL-MONO)" accessed Jul. 27, 2014; pp. 1-5.
NCT02058147 ClinicalTrials.gov "Efficacy and Safety of Insulin Glargine/Lixisenatide Fixed Ratio Combination Compared to Insulin Glargine Alone and Lixisenatide Alone on Top Metformin in Patients With T2DM (LixLan-O)" first received by ClinicalTrials.gov on Feb. 6, 2014, pp. 1-3.
NCT02058160 ClinicalTrials.gov "Efficacy and Safety of the Insulin Glargine/Lixisenatide Fixed Ratio Combination Versus Insulin Glargine in Patients With Type 2 Diabetes (LixiLan-L)" first received by ClinicalTrials.gov on Feb. 6, 2014, pp. 1-3.
NCT01195454, NIH Clinical Trials, "Euglycemic clamp dose-response study comparing insulin glargine U300 with Lantus U100" last updated Dec. 13, 2010, pp. 1-4.
NCT00763815, ClinicalTrials.gov, U.S. National Institutes of Health: "GLP-1 Agonist AVE0010 in Patients With Type 2 Diabetes for Glycemic Control and Safety Evaluation on Top of Pioglitazone (GETGOAL-P)" pp. 1-8 (Jun. 27, 2011).
EFC10780 (Sanofi study), "A randomized, double-blind, double-dummy, 2-arm parallel-group, multicenter 24-week study comparing the efficacy and safety of AVE0010 to sitagliptin as add-on to metformin in obese type 2 diabetic patients younger than 50 and not adequately controlled with metformin (EFC10780)" p. 1-4 (Jan. 29, 2014).
EFC10781 Clinical Trials, "24-week Treatment With Lixisenatide in Type 2 Diabetes Insufficiently Controlled With Metformin and Insulin Glargine" ClinicalTrials.gov; EFC10781 pp. 1-5 (Sep. 2009).
EFC6018; Clinical trial EudraCT 2007-005887-29, "GETGOAL-MONO" accessed Jul. 27, 2014; pp. 1-16.
EFC6017; Clinical Trial Eudra CT No. 2007-005884-92, accessed Apr. 24, 2015, one page.
Needleman et al., "A General Method Applicable to the Search for Similarities in the Amino Acid Sequence of Two Proteins," J. Mol. Biol. 48:443-453 (1970).
Neidle, "18.2 Failure Modes in the Discovery Process" Cancer Drug Design and Discovery, Elsevier/Academic Press, pp. 427-431 (2008).
Nettleton et al. "Characterization of the Oligomeric States of Insulin in Self-Assembly and Amyloid Fibril Formation by Mass Spectrometry," Biophysical J., v79, 2000, p. 1053-1065.
Nielsen et al., "Pharmacology of Exenatide (Synthetic Exendin-4): A Potential Therapeutic for Improved Glycemic Control of Type 2 Diabetes," Regul. Pept. 117(2):77-88 (2004).
Noble, et al., "Insulin Lispro: A Fast-Acting Insulin Analog," Am Fam Physician, 57(2):279-86 (1998).
Organization for Economic Co-Ooperation and Development; OECD Principles of Good Laboratory Practice and Compliance Monitoring (as revised in 1997); ENV/MC/CHEM (98)17:1-41 (Jan. 21, 1998).
Orskov, "Glucagon-like Peptide-1, a New Hormone of the Entero-insular Axis," Diabetologia 35(8):701-711 (1992).

Ott et al., "Diabetes in Germany" (DIG) study. "A prospective 4-year-follow-up study on the quality of treatment for type 2 diabetes in daily practice." Dtsch Med Wochenschr. 134(7):291-7 (2009). English Absract submitted.
Park et al., "PPARα agonis fenofibrate improves diabetic nephropathy in db/db mice," Kidney International, 69:1511-17 (published online Mar. 1, 2006).
Parkin "Guideline for Management of Postmeal Glucose" International Diabetes Federation, pp. 1-32 (Oct. 2007).
Patel & Advance Collaborative Group, "Effects of a fixed combination of perindopril and indapamide on macrovascular and microvascular outcomes in patients with type 2 diabetes mellitus (the Advance trial): a randomised controlled trial." Lancet 370(9590):829-40 (2007).
Patel & Borchardt, "Chemical pathways of peptide degradation. II. Kinetics of deamidation of an asparaginyl residue in a model hexapeptide," Pharmaceutical Research 7(7):703-11 (1990).
Pederson et al., "Improved Glucose Tolerance in Zucker Fatty Rats by Oral Administration of the Dipeptidyl Peptidase IV Inhibitor Isoleucine Thiazolidide." Diabetes 47(8):1253-58 (1998).
Perfetti "Combining basal insulin analogs with glucagon-like peptide-1 mimetics." Diabetes Technology & Therapeutics 13(9):873-81 (2011).
Pillion et al., "Dodecylmaltoside-mediated Nasal and Ocular Absorption of Lyspro-Insulin: Independence of Surfactant from Multimer Dissociation," Pharmaceutical Research, 15(10): 1637-39 (Oct. 1998).
Pinget et al., "Efficacy and Safety of Lixisenatide Once Daily Versus Placebo in Patients With Type 2 Diabetes Insufficiently Controlled on Pioglitazone (GetGoal-P)" Diabetes, 61(Supp 1):A258, Poster 1010-P (Jun. 2012).
Pi-Sunyer et aL, "The effects of pharmacologic agents for type 2 diabetes mellitus on body weight". Postgrad Med. 120(2):5-17 (Jul. 2008).
Pohl & Wank, "Molecular Cloning of the Heloderman and Exendin-4 cDNAs in the Lizard," J. Biol. Chem. 273 (16):9778-84 (1998).
Prandini "Methods of measuring gallbladder motor functions-the need for standardization: scintigraphy." Dig Liver Dis. 35 Suppl 3:S62-6 (2003).
"Preferable." Merriam-Webster.com. Merriam-Webster, n.d. Web. Sep. 7, 2015. http://www.merriamwebster.com/dictionary/preferable).
Pugeat et al., "Insulin Resistance, Polycystic Ovary Syndrome and Metformin" Review Article, Drugs 1999; 58(Suppl 1):41-46 (Sep. 1999).
Quianzon & Shomali, "Lixisentide-Once Daily Glucagon-like Peptide-1 receptor Agonist in the Management of Type 2 Diabetes", US Endocrinology, 7(2):104-9 (Winter 2011).
Raccah et al., "When Basal Insulin Therapy in Type 2 Diabetes Mellitus is Not Enough—What Next?" Diabetes Metabolism Research and Reviews 23:257-64 (published online Feb. 21, 2007).
Rao et al., "Is the combination of sulfonylureas and metformin associated with an increased risk of cardiovascular disease or all-cause mortality? A meta-analysis of observational studies." Diabetes Care. 31(8):1672-8 (2008).
Raju et al., "Optimum Palliation of Inoperable Hilar Cholangiocarcinoma: Comparative Assessment of the Efficacy of Plastic and Self-Expanding Metal Stents," Dig Dis Sci. 56:1557-64 (published online, Jan. 11, 2011).
Ratner et al. Abstract 131 "Post-meal pharmacodynamics profile of AVE0010, a once-daily GLP-1 receptor agonist, in patiens with type 2 diabetes inadequately controlled on metformin" Diabetologia 52(Suppl. 1): S60, #131 (Sep. 2009).
Ratner et al. "Dose-dependent effects of the once-daily GLP-1 receptor agonist lixisenatide in patients with Type 2 diabetes inadequately controlled with metformin: a randomized double-blind, placebo-controlled trial," Diabetic Med. 27 (9):1024-1032 (Sep. 2010).
Ratner et al., Poster "A dose-finding study of the new GLP-1 agonist AVE0010 in Type 2 Diabetes insufficiently controlled with metformin.", Diabetes, 57:Suppl.1, A129, Abstract No. 433-P, 68th Annual Meeting of the American Diabetes Association, San Francisco, Jun. 6-10, 2008.

(56) References Cited

OTHER PUBLICATIONS

Raufman "Bioactive peptides from lizard venoms," Regul Pept 61(1):1-18 (1996).
Request for "Type C" Meeting letter sent by Michael Lutz addressed to Mary Parks, dated Apr. 21, 2006, pp. 1-10.
Richter, von Margret, "Oldtimer as Newcomer" Pharmazie, pp. 1-9; http://www.pharmazeutische-zeitung.de/pza/2002-12/pharm1.htm (Feb. 2002).
Riddle et al., Contributions of Basal and Postprandial Hyperglycemia Over a Wide Range of A 1 C Levels Before and After Treatment Intensification in Type 2 Diabetes, Diabetes Care 34:2508-2514 (published online Oct. 25, 2011).
Riddle et al., Adding once-daily Lixisenatide for Type 2 Diabetes inadequately controlled by established basal insulin: a 24-week, randomized, placebo-controlled comparison (GetGoal-L). Diabetes Care 36(9):2489-96 (Sep. 2013).
Riddle et al., "Adding Once-Daily Lixisenatide for Type 2 Diabetes Inadequately Controlled with Newly Initiated and Continuously Titrated Basal Insulin Glargine" Diabetes Care, pp. 2497-2503 (Sep. 2013).
Ritzel et al., "A Synthetic Glucagon-Like Peptide-1 Analog with Improved Plasma Stability," J. Endocrine. 159 (1):93-102 (1998).
Rohrmann, "Differential Diagnosis of Pancreatic and Biliary Duct Diseases," Diseases of the Abdomen and Pelvis Syllabus, pp. 170-174 (1999).
Rosenstock et al., Poster "Efficacy and safety of lixisenatide once daily vs exenatiide twice daily in type 2 DM inadequately controlled on metformin (GetGoal-X)." 71st Scientific Sessions (Nov. 2011).
Rosenstock et al., OP 25 GLP-1 Based therapies, Abstract 145 "Dose range effects of the new once daily GLP-1 receptor agonist AVE0010 added to metformin in type 2 diabetes," Diabetologia 51 (Supplement 1):S66 (Sep. 2008).
Rosenstock et al., Abstract, 564P "Post-meal effects of AVE0010, a once-daily GLP-1 receptor agonist, in type 2 diabetes inadequately controlled on metformin," Diabetes 58(Suppl.1):A151-A152 (Jun. 1, 2009).
Rubino et al., "Delayed initiation of subcutaneous insulin therapy after failure of oral glucose-lowering agents in patients with type 2 diabetes: a population-based analysis in the UK." Diabet Med. 24(12):1412-18 (2007).
Sampson et al., "Second symposium on the definition and management of anaphylaxis: summary report—Second National Institute of Allergy and Infectious Disease/Food Allergy and Anaphylaxis Network symposium." Journal of Allergy and Clinical Immunology, 117(2):391-397 (2006).
Sanger et al., The amide groups of insulin, Biochem J. 59(3):509-18 (1955).
Sanofi's Lantus Draft Prescribing Information/Package Insert: "NDA 21-081 DRAFT package insert" (Sponsor revision #5) Date of submission: Apr. 20, 2000; see http://www.drugbank.ca/system/fds_labels/DB00047.pdf 1265922812; pp. 1-14.
Sanofi Press Release; "Lyxumia (lixisenatide) in Combination with Basal insulin plus Oral Anti-Diabetics Significantly Reduced HbA1c and Post-Prandial Glucose"; Paris, France (Jun. 9, 2012) pp. 1-6.
Sanofi-aventis Press Release, "Once Daily Lixisenatide (AVE 0010) Given as Monotherapy Successfully Meets Phase III Study Endpoints in Diabetes" Paris, France (Apr. 15, 2010) pp. 1-2.
Sanofi Press Release (Peron and Schaeffer), "Sanofi GetGoal Program on Lyxumia®, as an Add-on to Basal Insulin, Shows Significant Positive Phase III Results," Paris, France (May 31, 2011) pp. 1-2.
Sanofi Press release (Peron and Schaeffer); "Sanofi Reports Positive Results for Once-daily Lyxumia® (lixisenatide) in Combination with Lantus® (insulin glargine) in Type 2 Diabetes" Paris, France (Dec. 6, 2011) pp. 1-3.
Sanofi-aventis Press Release (Gabriel), "New Diabetes Compound AVE0010 Showed Clear Dose Response Results With Once-A-Day Injection in Phase IIb Study" Paris, France (Jun. 7, 2008) pp. 1-2.
Sanofi-aventis Press Release (Peron and Schaeffer), "Sanofi-aventis Announces Positive Top-line Lixisentatide Phase III Results" Paris, France (Feb. 2, 2011) pp. 1-2.
Sanofi Press Release (Peron and Schaeffer), "Lyxumia® (lixisenatide) One-Step Regimen as Effective as Two-Step Regimen in Improving Glycemic Control in Type 2 Diabetes" Paris, France (Sep. 12, 2011) pp. 1-3.
Sanofi Press Release (Sigurd), "Lixisenatide Significantly Reduces HbA1c Without Increasing Hypoglycemia in Patients Uncontrolled on Sulfonylureas", Pressmeddelande (Apr. 12, 2011) pp. 1-2.
Sanofi and Zealand Pharma Press Release (Evaluate), "Additional Positive Results from Global Phase III Program With Lixisenatide for Type 2 Diabetes", (Apr. 12, 2011) pp. 1-3.
Sanofi Press Release "Positive Results for Investigational Compound Lyxumia (Lixisenatide) Presented at American Diabetes Association's 71st Annual Scientific Sessions," (Jun. 24, 2011), pp. 1-5.
Sanofi Press Release entitled "FDA Accepts Sanofi's New Drug Application for Basal Insulin Toujeo®," dated Jul. 8, 2014, pp. 1-2.
Sanofi Press Release entitled "Sanofi Receives FDA Approval of Once-Daily Basal Insulin Toujeo®," dated Feb. 26, 2015, pp. 1-4.
Zealand Pharma Press Release entitled "Sanofi-Aventis finalize phase lia clinical study with GLP-1 agonist for type 2 diabetes licensed from Zealand Pharma" dated Mar. 3, 2005, one page.
Schellenberger et al., "Attempts for Quantifying The S' Subsite Specificity of Serine Proteases," Selected Papers Presented At the 2nd International Meeting on The Molecular And Cellular Regulation of Enzyme Activity, Advances in The Biosciences, Peptides and Proteases: Recent Advances 65:159-66 (1987).
Schellenberger et al., "Protease-Catalyzed Kinetically Controlled Peptide Synthesis," Angewante Chemie, International Edition 30(11):1437-49 (1991).
Schwartz et al., "A superactive insulin: [B10-Aspartic acid]insulin(human)," Proc. Natl. Acad. Sci. USA, 84 (18):6408-11 (Sep. 1987).
Schubert-Zsilavecz et al., "Better blood sugar control in diabetics. Insulin glargin—a long acting insulin analogue," Pharmazie in Unserer Zeit 30(2):125-30 (2001). With English translation.
Secnik Boye et al., "Patient-reported outcomes in a trial of exenatide and insulin glargine for the treatment of type 2 diabetes," Health and Quality of Life Outcomes, vol. 4, No. 80, pp. 1-8 (Oct. 2006).
Seino et al., "Randomized, double-blind, placebo-controlled trial of the once-daily GLP-1 receptor agonist lixisenatide in Asian patients with type 2 diabetes insufficiently controlled on basal insulin with or without a sulfonylurea (GetGoal-L-Asia)." Diabetes, Obesity and Metabolism 14(10):910-17 (2012).
Sharplin et al., "Improved glycaemic control by switching from insulin NPH to insulin glargine: a retrospective observational study," Cardiovascular Diabetology, 8(3):1-8 (published Jan. 19, 2009).
Sluzky et al., "Kinetics Of Insulin Aggregation In Aqueous Solutions Upon Agitation In The Presence Of Hydrophobic Surfaces," Proc. Natl. Acad. Sci. USA. 88(21):9377-81 (Nov. 1991).
Sporn & Suh, "Chemoprevention of cancer" Carcinogenesis, 21(3):535-530 (2000).
St. John Providence Health Center, "Preventing Obesity"http://www.stjohnprovidence.org/HealthInfolib/swarticle.aspx? type=85&id=P07863, Retrieved Aug. 22, 2013, pp. 1-2.
Starkova, ed., "Clinical Endocrinology", Guide for physicians, Moscow, "Medicine", 1991, p. 192-262.
Summary of Product Characteristics Lyxumia 10 micrograms solution for injection, pp. 1-93, published Mar. 14, 2013.
Sundby "Separation and Characterization of Acid-Induced Insulin Transformation Products by Paper Electrophoresis in 7 M Urea," J. Biol. Chem. 237(11)3406-11 (Nov. 1962).
"Suspension" Taber's Cyclopedic Medical Dictionary, 19th Edition, p. 2097 (F.A. Davis Co., Philadelphia 2001).
"Suspension" Stedman's Medical Dictionary, 20th Edition, p. 1450 (Williams & Wilkins Co., Baltimore 1961).
Tempero, "How I treat Pancreatic Ductal Adenocarcinoma," Current Clinical Issues, Journal of Oncology Practice, vol. 4, Issue 1, pp. 46-47 (2008).
Tessari et al., "Insulin in Methionine and Homocysteine Kinetics in Healthy Humans: Plasma Vs. Intracellular Models", Am J. Physiol Endocrine Metab 288(6):E1270-E1276 (2005).
Tews et al., Abstract of Oral Presentation "Enhanced Protection Against Cytokine- and Fatty Acid-induced Apoptosis in Ins-1 Beta-

(56) References Cited

OTHER PUBLICATIONS

Cells by Combined Treatment with Insulin Glargine and the Novel GLP-1 Receptor Agonist AVE0010" Diabetes, 56(Suppl. 1):A72-A73 (2007).
Tews et al., "Enhanced protection against cytokine- and fatty acid-induced apoptosis in pancreatic beta cells by combined treatment with glucagon-like peptide-1 receptor agonists and insulin analogues." Horm Metab Res. 40 (3):172-80 (Mar. 2008).
The Diabetes Control and Complications Trial Research Group, "The Effect of Intensive Treatment of Diabetes on the Development and Progression of Long-Term Complications in Insulin-Dependent Diabetes Mellitus", The New England Journal of Medicine, 329:977-86 (Sep. 1993).
Thong et al., "Safety, efficacy and tolerability of exenatide in combination with insulin in the Association of British Clinical Diabetologists nationwide exenatide audit." Diabetes, Obesity and Metabolism 13:703-10 (2011).
Turner et al., UK Prospective Diabetes Study (UKPDS) Group "Glycemic control with diet, sulfonylurea, metformin, pr insulin in patients with type 2 diabetes mellitus: Progressive requirement for multiple therapies (UKPDS 49)." JAMA 281(21):2005-12 (1999).
Thurow & Geisen, "Stabilisation of dissolved proteins against denaturation at hydrophobic interfaces," Diabetologia, 27(2):212-18 (Aug. 1984).
Tyler-Cross Schirch, "Effects of amino acid sequence, buffers, and ionic strength on the rate and mechanism of deamidation of asparagine residues in small peptides," J Biol Chem. 266(33):22549-56 (1991).
UK Prospective Diabetes Study (UKPDS) Group "Intensive blood-glucose control with sulphonylureas or insulin compared with conventional treatment and risk of complications in patients with type 2 diabetes (UKPDS 33)" The Lancet vol. 352 p. 837-853 (Sep. 12, 1998).
UK Prospective Diabetes Study (UKPDS) Group, "Effect of intensive blood-glucose control with metformin on complications in overweight patients with type 2 diabetes (UKPDS 34)" Lancet 352(9131):854-65 (Sep. 1998).
Uttenthel et al., "Molecular forms of flucagon-like peptide-1 in human pancreas and glucagonomas," J. Clin. Endocrinol. Metabol. 61(3):472-79 (1985).
Valle et al., "Cisplatin plus Gemcitabine versus Gemcitabine for Biliary Tract Cancer," N Engl J Med. 362 (14)1273-81 (Apr. 2010).
Van Delden, "Pancreas-Carcinoma, CT Assessment of Resectability," Radiology Department of the Academical Medical Centre, pp. 1-12 (Apr. 2006).
Victoza® Product information—European Medicines Agency, first published Aug. 7, 2009, pp. 1-2.
Victoza® Annex I—Summary of product characteristics. First published 2009, pp. 1-32.
Volund et al., "In Vitro and In Vivo Potency of Insulin Analogues Designed for Clinical Use," Diab. Med. 8(9):839-47 (Nov. 1991).
Vora et al., "Incretin-based therapy in combination with basal insulin: A promising tactic for the treatment of type 2 diabetes." Diabetes & Metab. 39(1):6-15 (2013).
Wafa et al., "Use of U-500 Regular Insulin in Type 2 Diabetes", Diabetes Care, 29(9):2175-2176 (2006).
Najchenberg, Chapter 23 "Clinical Approaches to preserve beta-cell function in Diabetes", Adv Exp Med Biol. 654:515-35 (2010).
Wan et al., "Enhancing the Activity of Insulin at the Receptor Interface: Crystal Structure and Photo-Cross-Linking of A8 Analogues," Biochemistry 43:16119-33 (2004).
Wang et al., "Real-world outcomes of US employees with type 2 diabetes mellitus treated with insulin glargine or neutral protamine Hagedorn insulin: a comparative retrospective database study." BMJ Open. 3:e002348 (2013), pp. 1-9.
Ward "Diabetic neuropathy," British Medical Bulletin, 45(1):111-26 (Jan. 1989).
Weiss et al., "Activities of Monomeric Insulin Analogs at Position A8 Are Uncorrelated With Their Thermodynamic Stabilities", The Journal of Biological Chemistry 276(43):40018-24 (2001).
Werner et al., "Pharmacological profile of lixisenatide: A new GLP-1 receptor agonist for the treatment of type 2 diabetes." Regulatory Peptides 164(2-3):58-64 (Epub Jun. 2, 2010).
Werner et al., "Insulin Glargine U-100 Has a Favourable Time-Action Profile Compared to U-40 or NPH Insulin in Healthy, Normoglycaemic Dogs", Poster-Abstract 37th Annual Meeting of Endocrine Society of India, Tirupati, A.P., India ESICON (2007) (2 pages including Abstract and Poster).
Weyer et al., "Long-term changes in insulin action and insulin secretion associated with gain, loss, regain and maintenance of body weight", Diabetologia, (43)1:36-46 (Jan. 2000).
White et al., "Randomized clinical trials with added rescue medication: some approaches to their analysis and interpretation." Statistics in Medicine 20:2995-3008 (2001).
Whittingham et al., "Insulin at PH2: Structural Analysis of the Conditions Promoting Insulin Fibre Formation" J. Mol. Biol., (2002), vol. 318, pp. 479-490.
WHO BMI classification, accessed at URL apps.who.int/bmi/index.jsp?introPage=itrol_3.html, Sep. 9, 2013, one page.
WHO Drug Information vol. 22(2), list 99, p. 142 (lixisenatide) (Jul. 2008).
WHO Rational Use of Medicines,http://www.who.int/medicines/areas/rational_use/en/downloaded Dec. 18, 2014 10:02:48 AM (2012).
Widjaja et al., "UKPDS 20: plasma leptin, obesity, and plasma insulin in type 2 diabetic subjects." J Clin Endocrinol Metab. 82(2):654-7 (1997).
Wiernsperger, et al. "The Antihyperglycaemic Effect of Metformin Therapeutic and Cellular Mechanisms" Review Article, Drugs 1999:58(Suppl 1):31-39 (Sep. 1999).
Yki-Jarvinen et al., "Insulin glargine or NPH combined with metformin in type 2 diabetes: the LANMET study." Diabetologia 49(3):442-51 (Mar. 2006).
Yki-Jarvin et al., "Thiazolidinediones," N Engl J Med. 351(11):1106-18 (Sep. 2004).
Yoon et al., "Exenatide added to insulin therapy: a retrospective review of clinical practice over two years in an academic endocrinology outpatient setting." Clinical Therapeutics 31(7):1511-23 (2009).
Yu et al., "Effect of Zinc Sulphate and Zinc Methionine on Growth, Plasma Growth Hormone Concentration, Growth Hormone Receptor and Insulin-Like Growth Factor-1 Gene Expression in Mice", Clin Exp Pharmacal Physiol 32(4):273-78 (2005). Abstract only.
Ziemer et al., "Clinical inertia contributes to poor diabetes control in a primary care setting" The Diabetes Educ 31 (4):564-71 (2005).
Ziessman et al., "Sincalide-stimulated cholescintigraphy: a multicenter investigation to determine optimal infusion methodology and gallbladder ejection fraction normal values." J Nucl Med. 51(2):277-81 (Feb. 2010).
Zimmet, et al. "Clinical Efficacy of Metformin against Insulin Resistance Parameters, Sinking the Iceberg" Review Article, Drugs 1999: 58(Suppl 1):21-28 (Sep. 1999).
Zinman "The Physiologic Replacement of Insulin," New England J. Med. 321(6):363-70 (Aug. 1989).
Zinman et al., "Efficacy and safety of the human glucagon-like peptide-1 analog liraglutide in combination with metformin and thiazolidinedione in patients with type 2 diabetes (LEAD-4 Met+ TZD)." Diabetes Care, 32 (7)1224-30 (Jul. 2009).
Translation of pp. 1109, 1116 and 1117 of "Clinical Effectiveness of Long-Term Administration of BAY g5421 (Acarbose) on Insulin-Treated Diabetes," Jpn. Pharmacal. Ther; 1996 vol. 24 No. 5: 1109-1129, pp. 1-4.
Translation of pp. 2346 and 2348 of Rinsho to Kenkyu, "Effectiveness of Combination Therapy Using Voglibose and Insulin in Patients with NIDDM," 1997, vol. 74, No. 9: 2346-2352, pp. 1-3.
Translation of pp. 121 and 124 of Igaku to Yakugaku, "Utility of Voglibose Long-term Combined Therapy in Non-Insulin Dependent Diabtetic Patients with Little Effective of Sulfonylureas," 1999, vol. 42, No. 1: 121-129, pp. 1-3.

(56) References Cited

OTHER PUBLICATIONS

Translation of pp. 750, 753 and 754 of Igaku no Ayumi, "Incretin Receptors," 2010, May, vol. 233; No. 9: 750-754, pp. 1-4.

Xie et al., "Characterization of protein impurities and site-specific modifications using peptide mapping with liquid chromatography and data independent acquisition mass spectrometry." Anal Chem. 81(14):5699-708 (Jul. 2009).

Laursen et al., "Enhanced monitoring of biopharmaceutical product purity using liquid chromatography-mass spectrometry." 1218(28):4340-48 (Jul. 2011; Epub May 2011).

Gygi et al., "Quantitative analysis of complex protein mixtures using isotope-coded affinity tags." Nat Biotechnol. 17(10):994-99 (Oct. 1999).

Seino et al., and The Committee of Japan Diabetes Society on the diagnostic criteria of diabetes mellitus. "Report of the committee on the classification and diagnostic criteria of diabetes mellitus." Journal of the Japan Diabetes Society. 53:450-467 (2010). In Japanese, English translation of selected passages provided.

Final Rejection issued in U.S. Appl. No. 13/509,542, mailed Feb. 10, 2016, pp. 1-40.

Final Rejection issued in U.S. Appl. No. 13/467,707; mailed Feb. 12, 2016, pp. 1-12.

Final-Rejection issued in U.S. Appl. No. 13/432,811; mailed Feb. 10, 2016, pp. 1-9.

Non-Final Rejection issued in U.S. Appl. No. 13/382,442; mailed Mar. 31, 2016, pp. 1-29.

International Search Report by the ISA for International Application No. PCT/EP2015/079285; dated Mar. 9, 2016, pp. 1-7.

English translation of the TIPO Search Report for ROC Patent Application No. 104116749, dated Feb. 22, 2016, one page.

English translation of the TIPO Search Report for ROC Patent Application No. 101131466 dated Mar. 2, 2016, one page.

\* cited by examiner

PHARMACEUTICAL COMPOSITION FOR USE IN THE TREATMENT OF A NEURODEGENERATIVE DISEASE

CROSS-REFERENCE TO RELATED APPLICATIONS

This application claims the benefit of U.S. Provisional Application No. 61/530,146 filed on Sep. 1, 2011.

Subject of the present invention is a pharmaceutical composition for use in the prevention or/and treatment of a neurodegenerative disease, the composition comprising desPro$^{36}$Exendin-4(1-39)-Lys$_6$-NH$_2$ or/and a pharmaceutically acceptable salt thereof, and optionally a pharmaceutically acceptable carrier, adjuvant, or/and auxiliary substance.

Alzheimer's Disease

Alzheimer's disease (AD) is a neurodegenerative disorder that results in the loss of cortical neurons, especially in the associative neocortex and hippocampus which in turn leads to slow and progressive loss of cognitive functions, ultimately leading to dementia and death. Major hallmarks of the disease are aggregation and deposition of misfolded proteins (Bertram et al 2010; Mancuso et al 2010): (1) aggregated beta-amyloid (Aβ) peptide as extracellular senile or neuritic 'plaques', and (2) hyperphosphorlylated tau protein as intracellular neurofibrillary 'tangles' (NFTs).

Genetically, AD is divided into two forms: (1) early-onset familial AD (<60 years), and (2) late-onset sporadic AD (>60 years). Rare, disease causing mutations in Amyloid precursor protein (APP), Presenilin 1 (PSEN1), and Presenilin 2 (PSEN2) genes are known to result in early-onset familial AD while, APOE (allele 4) is the single most important risk factor for late-onset AD (Bertram et al 2010).

Mitochondrial dysfunction and oxidative stress, demonstrated by protein oxidation and lipid peroxidation are characteristics of AD brain. An imbalance between production of reactive oxygen species (ROS) and breakdown of the chemically reactive species by antioxidants leads to oxidative stress. Aβ has direct oxidative effects but it can also disrupt mitochondrial redox activity resulting in an increase of free radicals. Neurons are less capable to defend against an increase in ROS as they have low levels of antioxidants relative to other mammalian cell types and thus are considered highly susceptible to oxidative stress. Addition of Aβ to primary neuronal cultures results in inhibition of ATPases, changes in cell potential, and Ca$^{2+}$ influx (Varadarajan et al 2000; Higginsa et al 2010).

There is no cure for this devastating disease at present and the few treatments approved by the US Food and Drug Administration (FDA) do not stop the progression of AD rather are only partially effective in improving the symptoms (Wollen 2010, Aderinwale et al 2010). Currently, licensed pharmaceutical therapies against AD are the acetylcholinesterase inhibitors such as Tacrine, Donepizil, Rivastigmine, Galantamine and the NMDA receptor antagonist memantine. The effect of these drugs is very limited, and the main action again is to reduce symptoms rather than prevent the development of the disease. Other drugs may be given 'off label', such as statins (cholesterol level reducing agents), antihypertensive drugs, anti-inflammatory drugs, or others. None of these drugs have been proven to reduce progression of AD (Kaduszkiewicz et al 2005; Hölscher, 2005). Other strategies for treating AD are under investigation. It has been found that Neuronal Growth Factor α (NGF) can decrease senile plaques and improve cognitive function (De Rosa et al 2005). Since insulin resistance is now known as one of the main problems in AD (Hölscher and Li, 2010), instead of insulin itself other growth factors such as the incretin hormone Glucagon-like peptide-1 (GLP-1) are showing good effects in pre-clinical studies. The GLP-1 incretin analogue liraglutide reduced the number of amyloid plaques, reduced beta-amyloid levels, prevented cognitive impairment and synaptic dysfunction, reduced the inflammation response and enhanced synapse growth and neurogenesis in the brains of a transgenic mouse model of AD (McClean et al 2011). The amyloid plaques and the associated inflammation response in the brain are key hallmarks of AD. Similar protective effects were found with another GLP-1 analogue receptor agonist in a transgenic mouse model of AD (Li et al 2010).

Parkinson's Disease

Parkinson's disease (PD) is a chronic neurodegenerative disorder of muscle movement commonly characterized by selective degeneration of nigrostriatal neurons, greatly reduced synthetic capacity for dopamine and a consequent failure to engage striatal dopamine receptors. (Gandhi et al 2005). Before the disease presents clinically, death of nigrostriatal neurons occurs in the substantia nigra pars compacta (SNc) silently, probably as a result of the occurrence of concurrent apoptotic, excitotoxic, free-radical mediated neuroinflammatory events. A therapeutic strategy offering cure for, or a means of arresting the pathology of PD remains elusive. Established drug therapies are essentially palliative and not effective in all patients. Since apoptotic cell death is one of the central components in selective nigrostriatal neuronal death (Schapira 2001) future therapeutic strategies could involve the targeted use of bio-molecules with anti-apoptotic properties. Alternatively, a positive therapeutic effect could be produced by molecules with neurotrophic properties or the ability to stimulate neurogenesis of cells with a dopaminergic phenotype. It has recently be observed that the glucagon-like peptide-1 receptor (GLP-1) agonist exendin-4 shows neurotrophic (Perry et al 2002) and neuroprotective (Perry et al 2002) properties in cultures of PC12 cells subjected to excitotoxic stress. Recently, it was shown (Harkavyi et al 2008) that exendin-4 arrests progression of, or even reverse nigral lesions, once established in two PD mouse models. In addition, it has been shown that exendin-4 treatment protected dopaminergic neurons against degeneration, preserved dopamine levels, and improved motor function in the 1-methyl-4-phenyl-1,2,3,6-tetrahydropyridine (MPTP) mouse model of PD (Li et al 2009).

Huntington's Disease

Huntington's disease (HD) is an inherited neurodegenetative disorder typified by involuntary body movement, as well as psychiatric and cognitive abnormalities. The genetic defect underlying HD involves expansion of CAG trinucleotide repeats in exon 1 of the HD gene, resulting in polyglutamine expansion in the huntingtin (htt) protein. This leads to abnormal processing and deleterious intracellular aggregation. Recently it has been shown that exendin-4 treatment suppresses the development of mutant htt inclusions in the pancreas and brain ameliorates metabolic effects and motor dysfunction and extends survival of HD mice (Martin et al 2009).

Stroke

The pathophysiology of stroke includes death of cortical and striatal neurons via apoptosis (Mattson, 2007).

Recently it has been shown that administration of exendin-4 reduced brain damage and improved functional outcome in a transient middle cerebral artery occlusion stroke mouse model (Li et al 2009). In a cerebral ischemia model in the gerbil, it was further shown that GLP-1 receptor stimulation with exendin-4 attenuated the ischemia-related neuronal death by interfering with microglial activation against transient cerebral ischemic damage. (Lee et al 2011). Teramoto et al (2011) showed that exendin-4 is effective in a cerebral ischemia-reperfusion injury mouse model. Exendin-4 treatment significantly reduced infarct volume and improved functional deficit.

Peripheral Sensory Neuropathy

About 60-70% of individuals with diabetes have some degree of neurological damage, specifically neuropathies that cause impaired sensation in the hands and/or feet, slowed gastric motility or carpal tunnel syndrome. There is currently no therapy proven to reverse the neurological damage caused by prolonged hyperglycaemia and the associated metabolic disturbances. GLP-1 expression has been identified in neurons in the nodose ganglion, suggesting a role of GLP-1 in peripheral neurotransmission (Nakagawa 2004). In a rodent model of pyridoxine-induced peripheral neuropathy in non-diabetic rodents, GLP-1 and s.c. exendin-4 were shown to partially protect against several pyridoxine-induced functional and morphological defects and to facilitate normalization of axonal size (Perry et al 2007).

Cognitive Function, Mood and Memory:

GLP-1 receptor agonists are able to enhance cognitive function in rodents, as measured in the Morris water maze; the GLP-1 receptor knock-out mouse has a phenotype characterized by a learning deficiency that is restored after hippocampal GLP-1 receptor gene transfer (During of al 2003). Recently, Isacson et al (2010) showed an effect of chronic exendin-4 treatment on hippocampus-associated cognitive and mood-related behaviour in adult rodents. In another study, the polyneuropathy found in the dorsal root ganglion of a mouse model of diabetes was reversed by exendin-4 (Himeno et al 2011). Another GLP-1 analogue, liraglutide has been shown to exert beneficial effects on cognitive function and hippocampal synaptic plasticity in mice with high fat dietary-induced obesity and insulin resistance (Porter et al 2010).

Glucagon-Like Peptide 1

Glucagon-like peptide 1, GLP-1 or GLP-1 (7-36) is a 30-amino acid peptide hormone that is encoded in the proglucagon gene. It is mainly produced in enteroendocrine L cells of the gut and is secreted into the blood stream when food containing fat, protein hydrolysate, and/or glucose enters the duodenum. The most widely studied cell activated by GLP-1 is the insulin-secreting beta cell in the pancreas where its defining action is augmentation of glucose-induced insulin secretion. Upon GLP-1 receptor (GLP-1R) activation in the beta cells, adenylyl cyclase (AC) is activated and cAMP is generated, leading, in turn, to cAMP-dependent activation of second messenger pathways, such as the protein kinase A (PKA) and Epac pathways. As well as short-term effects of enhancing glucose-induced insulin secretion, continuous GLP-1R activation also increases insulin synthesis, beta cell proliferation and neogenesis (Doyle et al 2007). Furthermore, GLP-1 generally regulates the concentrations of glucagons, slows down gastric emptying, stimulates the biosynthesis of (Pro-)insulin, increases the sensitivity toward insulin, and stimulates the insulin-independent biosynthesis of glycogen (Hoist (1999); Curr. Med. Chem. 6: 1005; Nauck et al (1997) Exp Clin Endocrinol Diabetes 105:187; Lopez-Delgado et al (1998) Endocrinology 139:2811).

The particular effects of GLP-1 on insulin and glucagon secretion have generated a research activity over the past 20 years culminating in a naturally occurring GLP-1 receptor (GLP-1R) agonist, exendin 4, now being used to treat type 2 diabetes mellitus (T2DM) (Doyle et al 2007).

In tissues other than the pancreas (brain, kidney, lung, heart, and major blood vessels) GLP-1 can activate a specific guanine nucleotide-binding protein (G-protein) coupled receptor.

GLP-1 has shown growth factor-like as well as neuroprotective properties (McClean et al 2010). GLP-1 also reduces the induction of apoptosis of hippocampal neurons and improves spatial and associative learning (During et al 2003). Perry of al (2002) reported that GLP-1 could completely protect cultured rat hippocampal neurons against glutamate-induced apoptosis. The GLP-1 analogues (Val8)GLP-1 and N-acetyl-GLP-1 have shown prominent effects on long term potentiation of synaptic transmission (LTP) in the hippocampus (McClean et al 2010). The GLP-1 analogue liraglutide reduced the number of amyloid plaques, reduced beta-amyloid levels, prevented cognitive impairment and LTP depression, reduced the inflammation response and enhanced synapse growth and neurogenesis in the hippocampus of a transgenic mouse model of AD (McClean et al 2011).

GLP-1, liraglutide and exendin-4 have been shown to cross the blood brain barrier (BBB) (Kastin et al 2001; McClean et al 2011). Perry et al (2003) found that GLP-1 and exendin-4 reduced the levels of beta amyloid in the brain and amyloid precursor protein in neurons. Chronic treatment with exendin-4 or liraglutide affects cell proliferation and neuroblast differentiation in the adult mouse hippocampal dentate gyrus (Li at al 2010; Hamilton at al 2011).

Liraglutide is a GLP-1 analogue having the formula $Arg^{34}$, $Lys^{26}(N^{\epsilon}(\gamma\text{-glutamyl}(N^{\alpha}\text{-hexadecanoyl})))GLP\text{-}1(7\text{-}37)$. Liraglutide is usually administered parenterally.

The compound $desPro^{36}Exendin\text{-}4(1\text{-}39)\text{-}Lys_6\text{-}NH_2$ (AVE0010, lixisenatide) is an analogue of exendin-4. Lixisenatide is disclosed as SEQ ID NO:93 in WO 01/04156:

SEQ ID NO: 1: Lixisenatide (44 AS)
H-G-E-G-T-F-T-S-D-L-S-K-Q-M-E-E-E-A-V-R-L-F-I-E-

W-L-K-N-G-G-P-S-S-G-A-P-P-S-K-K-K-K-K-K-$NH_2$

SEQ ID NO: 2: Exendin-4 (39 AS)
H-G-E-G-T-F-T-S-D-L-S-K-Q-M-E-E-E-A-V-R-L-F-I-E-

W-L-K-N-G-G-P-S-S-G-A-P-P-P-S-$NH_2$

SEQ ID NO: 3: GLP-1(7-36) (30 AS)
H-A-E-G-T-F-T-S-D-V-S-S-Y-L-E-G-Q-A-A-K-E-F-I-A-

W-L-V-K-G-R

Exendins are a group of peptides which can lower blood glucose concentration. Exendins have an amino acid sequence identity of only about 50% with GLP-1 (7-36). Therefore, exendins are generally not regarded as GLP-1 analogs.

Lixisenatide is characterised by C-terminal truncation of the native exendin-4 sequence. Lixisenatide comprises six C-terminal lysine residues not present in exendin-4. Up to now, lixisenatide has not been considered as a drug suitable for the treatment of CNS disorders, in particular neurodegenerative diseases, as the C-terminal lysine residues may prevent the drug to pass the blood-brain-barrier. At present, there is no indication that lixisenatide could be transported across the blood-brain-barrier by a specific or/and regulated mechanism.

In example 1 of the present invention, is has been demonstrated that lixisenatide has superior properties compared to the GLP-1 analogue liraglutide and to exendin-4, both of which are currently used as treatments for type 2 diabetes:

(a) Surprisingly, lixisenatide can cross the blood brain barrier. The data of the present invention indicate that the transport is regulated, as the transport rate at high concentrations is limited to a maximum level. Furthermore, lixisenatide is taken up into the brain at a lower parenteral dose as compared with liraglutide.

(b) Lixisenatide activates GLP-1 receptors in the brain and induces cAMP production. Surprisingly, lixisenatide produces higher levels of cAMP than liraglutide, demonstrating higher effectiveness at activating the GLP-1 receptor at the same dose.

(c) Lixisenatide can induce proliferation of progenitor cells in the dentate gyrus. Compared with exendin-4 or with liraglutide, lixisenatide provides enhanced effects when administered at the same dose. In neurodegenerative diseases, these effects can constitute a disease-modifying effect.

(d) Lixisenatide showed superior neuroprotective effects (against cellular stress) in the dentate gyrus when compared with liraglutide.

(e) surprisingly, a pre-treatment with a dose of 10 nM lixisenatide was sufficient in protecting SH-SY5Y neuroblastoma cells from 1200 μM Methyl Glyoxal stress. A dose of 200 nM liraglutide was necessary in protecting cells from 1200 μM Methyl Glyoxal stress, indicating that a lower dose of lixisenatide is sufficient to induce protection (see also data of Example 2 obtained by pre-treatment with GLP-1 agonists).

Example 2 demonstrates that a post-treatment with lixisenatide was sufficient in protecting SH-SY5Y neuroblastoma cells from 2 mM Methyl Glyoxal stress or 1 mM $H_2O_2$ stress. In contrast, Liraglutide did not protect cells from the stress by MG or $H_2O_2$.

In Example 3, Lixisenatide exhibited significant neuroprotective effects in rotenone treated LUHMES cells against neurodegeneration. Lixisenatide provides advantages compared with other GLP-1 receptor (GLP-1R) agonists. In rotenone treated LUHMES cells, Lixisenatide is significantly active at 3-fold lower concentrations than Liraglutide, a result comforting the unexpected superior activity effect seen in the Methyl Glyoxal model of Example 1. Exenatide did not elicit a significant effect at concentrations of 0.3 and 1 μM. In contrast, Lixisenatide provides a dose-dependent improvement of viability at these concentrations.

In Example 4, it is demonstrated that lixisenatide treatment in vivo leads to a decrease of amyloid plaque load in the brain of transgenic mice, models of Alzheimer's disease. Therefore, in addition to its neuroprotective properties, lixisenatide can decrease cerebral pathological lesions such as amyloid plaques and represents therefore an attractive prevention or/and treatment for Alzheimer's Disease. Activity is observed at lower dose (10 nmol/kg) than previously described for liraglutide (25 nmolm/kg) by McLean et al (2011).

Therefore, lixisenatide is suitable for the treatment or/and prevention of a neurodegenerative disease, as described herein, for example Alzheimer's disease, Parkinson's disease or/and stroke.

A first aspect of the present invention is a pharmaceutical composition for use in the prevention or/and treatment of a neurodegenerative disease, the composition comprising desPro$^{36}$Exendin-4(1-39)-Lys$_6$-NH$_2$ or/and a pharmaceutically acceptable salt thereof, and optionally a pharmaceutically acceptable carrier, adjuvant, or/and auxiliary substance.

Another aspect of the present invention is a pharmaceutical composition for use in the treatment of a neurodegenerative disease, the composition comprising desPro$^{36}$Exendin-4(1-39)-Lys$_6$-NH$_2$ or/and a pharmaceutically acceptable salt thereof, and optionally a pharmaceutically acceptable carrier, adjuvant, or/and auxiliary substance.

The neurodegenerative disease may be any neurodegenerative disease, in particular a neurodegenerative disease which is associated with oxidative stress, loss of neurite integrity, apoptosis, neuronal loss or/and inflammation response.

In the present invention, loss of neurite integrity includes dendritic spine loss, loss of synaptic plasticity, or/and loss of new compensatory neurite sprouting.

The neurodegenerative disease may be associated with cognitive impairment.

In particular, the neurodegenerative disease is selected from the group consisting of Alzheimer's disease, Parkinson's disease, progressive supranuclear palsy (PSP), multiple system atrophy (MSA), Lewy body dementia, Parkinson's disease dementia, epilepsy, stroke, Huntington's Chorea, cerebral hypoxia, multiple sclerosis, and peripheral neuropathy. The peripheral neuropathy may be associated with diabetes mellitus.

It is preferred that the neurodegenerative disease is selected from the group consisting of Alzheimer's disease, Parkinson's disease, and stroke.

It is also preferred that the neurodegenerative disease is selected from the group consisting of progressive supranuclear palsy, multiple system atrophy, Lewy body dementia, Parkinson's disease, and Parkinson's disease dementia. Any one of these diseases may be associated with Parkinsonism.

Progressive supranuclear palsy and multiple system atrophy are collectively known as Parkinson-plus syndromes.

In the present invention, Parkinsonism is a neurological syndrome which is characterised by a combination of specific symptoms such as tremor, hypokinesia, rigidity, or/and postural instability.

In one embodiment, the neurodegenerative disease is Alzheimer's disease. Alzheimer's disease can be associated with oxidative stress and neuronal loss.

In another embodiment, the neurodegenerative disease is Parkinson's disease. Parkinson's disease may be associated with oxidative stress, inflammatory response, apoptosis, neuronal loss, in particular loss of dopaminergic neurons, for example neuronal loss in the substantia nigra resulting in a lack of dopamine.

Neuronal loss may be caused by apoptosis.

In another embodiment, the neurodegenerative disease is progressive supranuclear palsy. Progressive supranuclear palsy may be associated with neuronal loss, in particular loss of dopaminergic neurons.

In another embodiment, the neurodegenerative disease is multiple system atrophy. Multiple system atrophy may be associated neuronal loss, in particular loss of dopaminergic neurons.

In another embodiment, the neurodegenerative disease is Lewy body dementia. Lewy body dementia may be associated with neuronal loss, in particular loss of dopaminergic neurons. Lewy body dementia may be associated with Parkinson's disease.

In another embodiment, the neurodegenerative disease is Parkinson's disease dementia. Parkinson's disease dementia may be associated neuronal loss, in particular loss of dopaminergic neurons. In particular, Parkinson's disease dementia is associated with Parkinson's disease.

In yet another embodiment, the neurodegenerative disease is stroke. Stroke may be associated with neuronal loss caused by ischemia, wherein ischemia may be caused by blockage (such as thrombosis or arterial embolism) or haemorrhage.

In yet another embodiment, the neurodegenerative disease is multiple sclerosis, which may be associated with inflammatory processes in the CNS.

The data of the present invention demonstrate that (a) lixisenatide provides neuroprotective or/and neurogenerative effects, and (b) lixisenatide is superior compared with other GLP-1 agonists, such as exendin-4 or liraglutide. Thus lixisenatide can provide a disease-modifying effect in neurodegenerative diseases, such as Alzheimer's disease, Parkinson's disease, and stroke. In particular, administration of lixisenatide is suitable for the treatment in an early stage of a neurodegenerative disease, as neuroprotection and neurogeneration could slow down the progression of the disease and thereby improve quality of life.

Therefore, in one aspect of the present invention, the neurodegenerative disease is in an early stage. For example, the Alzheimer's disease may be an early-stage Alzheimer's disease. Early-stage Alzheimer's disease (AD) is also termed prodromal Alzheimer's disease or predementia Alzheimer's disease. (Dubois et al. 2010). Early stage Alzheimer's disease can be defined as: patients presenting objective memory complaint associated with supportive biomarker data or Alzheimer's disease pathology: in cerebrospinal fluid (CSF) low levels of β-amyloid 42 (Ab42) peptide over Tau protein ratio are found, or amyloid plaque in the brain are detected by amyoid PET (positron emission tomography) agent such as AmyVid™ from E. Lilly (Avid).

In another example, the Parkinson's disease may be an early-stage Parkinson's disease. In yet another example, the progressive supranuclear palsy may be an early-stage progressive supranuclear palsy. In yet another example, the multiple system atrophy may be an early-stage multiple system atrophy. In another example, the Lewy body dementia may be an early-stage Lewy body dementia. In a further example, the Parkinson's disease dementia may be an early-stage Parkinson's disease dementia.

Furthermore, lixisenatide is suitable in the prevention of a neurodegenerative disease, in particular in those patients suspected of suffering from a neurodegenerative disease without having a clear diagnosis. In another aspect of the present invention, the pharmaceutical composition, as described herein, is for use in the prevention of a neurodegenerative disease.

In the context of the present invention, desPro$^{36}$Exendin-4(1-39)-Lys$_6$-NH$_2$ (lixisenatide) includes pharmaceutically acceptable salts thereof. The person skilled in the art knows pharmaceutically acceptable salts of lixisenatide. A preferred pharmaceutically acceptable salt of lixisenatide employed in the present invention is acetate.

In the present invention, desPro$^{36}$Exendin-4(1-39)-Lys$_6$-NH$_2$ or/and the pharmaceutically acceptable salt thereof may be administered to a patient in need thereof, in an amount sufficient to induce a therapeutic effect.

In the present invention, desPro$^{36}$Exendin-4(1-39)-Lys$_6$-NH$_2$ or/and the pharmaceutically acceptable salt thereof may be formulated with suitable pharmaceutically acceptable carriers, adjuvants, or/and auxiliary substances.

The pharmaceutical composition of the present invention provides a disease-modifying effect by its neuroprotective and neuroregenerative effects, as described herein, in a neurodegenerative disease, as described herein. In particular, a disease-modifying response can be obtained in the treatment of a neurodegenerative disease as described herein, for example in Alzheimer's disease, Parkinson's disease, progressive supranuclear palsy, multiple system atrophy, Lewy body dementia, Parkinson's disease dementia, epilepsy, stroke, Huntington's Chorea, cerebral hypoxia, multiple sclerosis, and peripheral neuropathy as described herein.

The pharmaceutical composition of the present invention may be administered parenterally, e.g. by injection (such as by intramuscular or by subcutaneous injection). Suitable injection devices, for instance the so-called "pens" comprising a cartridge comprising the active ingredient, and an injection needle, are known. The compound desPro$^{36}$Exendin-4(1-39)-Lys$_6$-NH$_2$ or/and a pharmaceutically acceptable salt thereof may be administered in a suitable amount, for instance in an amount in the range of 1 to 50 μg per dose, 5 to 40 μg per dose, 10 to 30 μg per dose, 10 to 15 μg per dose or 15 to 20 μg per dose.

In the present invention, the compound desPro$^{36}$Exendin-4(1-39)-Lys$_6$-NH$_2$ or/and a pharmaceutically acceptable salt thereof may be administered in a daily dose in the range of 1 to 50 μg, in the range of 5 to 40 μg, in the range of 10 to 30 μg, in the range of 10 to 20 μg, in the range of 10 to 15 μg, or in the range of 15 to 20 μg. The composition of the present invention may be administered by one injection per day.

In the present invention, the composition of the present invention may be provided as a liquid composition. The skilled person knows liquid compositions of lixisenatide suitable for parenteral administration. A liquid composition of the present invention may have an acidic or a physiologic pH. An acidic pH preferably is in the range of pH 1-6.8, pH 3.5-6.8, or pH 3.5-5. A physiologic pH preferably is in the range of pH 2.5-8.5, pH 4.0-8.5, or pH 6.0-8.5. The pH may be adjusted by a pharmaceutically acceptable diluted acid (typically HCl) or pharmaceutically acceptable diluted base (typically NaOH).

The liquid composition of the present invention may comprise a suitable preservative. A suitable preservative may be selected from phenol, m-cresol, benzyl alcohol and p-hydroxybenzoic acid ester. A preferred preservative is m-cresol.

The liquid composition of the present invention may comprise a tonicity agent. A suitable tonicity agent may be selected from glycerol, lactose, sorbitol, mannitol, glucose, NaCl, calcium or magnesium containing compounds such as CaCl$_2$. The concentration of glycerol, lactose, sorbitol, mannitol and glucose may be in the range of 100-250 mM. The concentration of NaCl may be up to 150 mM. A preferred tonicity agent is glycerol.

The liquid composition of the present invention may comprise methionine from 0.5 μg/mL to 20 μg/mL, preferably from 1 μg/ml to 5 μg/ml. Preferably, the liquid composition comprises L-methionine.

Yet another aspect of the present invention refers to a method for the prevention or/and treatment of a medical indication, as described herein. For example, the method may comprise the administration of the pharmaceutical composition as described herein. The method may be a method for the prevention or/and treatment of a neurodegenerative disease, as described herein.

In particular, the method, as described herein, elicits a disease-modifying response, for example by neuroprotection or/and neurogeneration.

In the method of the present invention, a disease-modifying therapy by its neuroprotective and neuroregenerative effects is provided by administration of the pharmaceutical composition, as described herein, in a neurodegenerative disease, as described herein. In particular, a disease-modifying response can be obtained in the treatment of a neurodegenerative disease as described herein, for example in Alzheimer's disease, Parkinson's disease, progressive supranuclear palsy, multiple system atrophy, Lewy body dementia, Parkinson's disease dementia, epilepsy, stroke, Huntington's Chorea, cerebral hypoxia, multiple sclerosis, and peripheral neuropathy, as described herein.

In the method of the present invention, a therapeutically effective amount of the pharmaceutical composition, as described herein, is administered.

Yet another aspect of the present invention refers to the use of the composition as described herein for the manufacture of a medicament for the treatment of a medical indication, as described herein. For example, the composition of the present invention can be used for the manufacture of a medicament for the prevention or/and treatment of a neurodegenerative disease, as described herein.

The invention is further illustrated by the following examples and figures.

FIGURE LEGENDS

FIG. 1. (A) Total lixisenatide concentration (pmol/L) measured in the brains of wild type female mice (n=5, average age 24 weeks) at 30 min following i.p. saline vehicle (0.9% w,v NaCl) or i.p. lixisenatide (2.5, 25 or 250 nmol/kg body weight) injection. Values are the mean±S.E.M. $*p<0.05$, $**p<0.01$. (B) Total lixisenatide concentration (pmol/L) measured in the brains of wild type female mice (n=5, average age 24 weeks) at 3 h following i.p. saline vehicle (0.9% w,v NaCl) or i.p. lixisenatide (2.5, 25 or 250 nmol/kg body weight) injection, Values are the mean±S.E.M. $*p<0.05$.

Figure 2A:
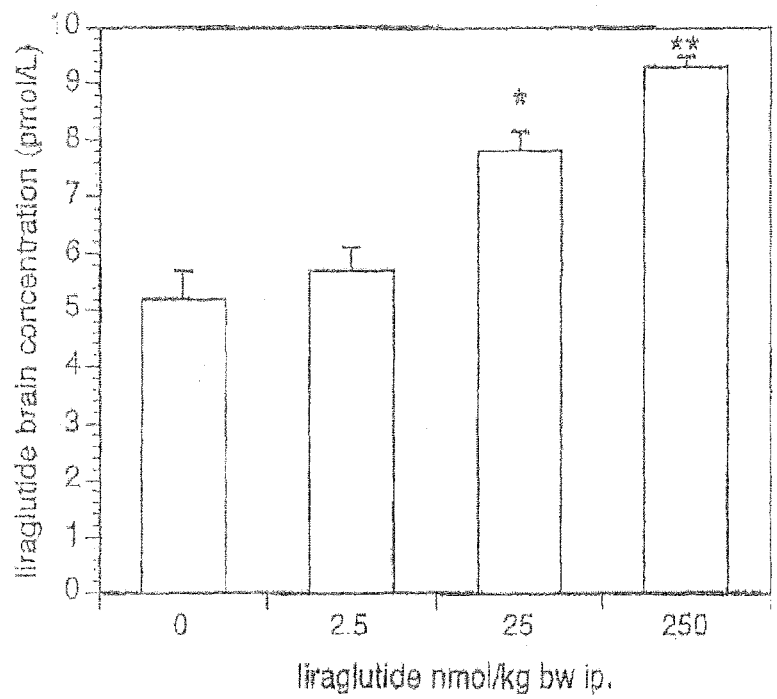
Figure 2B:
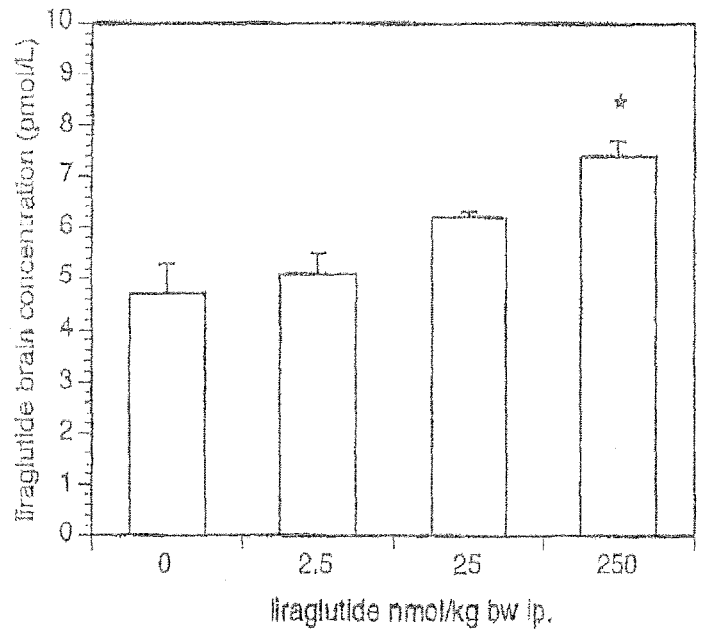

FIG. 2. (A) Total liraglutide concentration (pmol/L) measured in the brains of wild type female mice (n=5) at 30 min following i.p. saline vehicle (0.9% w,v NaCl) or i.p. liraglutide (2.5, 25 or 250 nmol/kg body weight) injection. Values are the mean±S.E.M. $*p<0.05$, $**p<0.01$. (B) Total liraglutide concentration (pmol/L) measured in the brains of wild type female mice at 3 h following i.p. saline vehicle (0.9% w,v NaCl) or i.p. liraglutide (2.5, 25 or 250 nmol/kg body weight) injection. Values are the mean±S.E.M. $*p<0.05$.

Figure 3A:
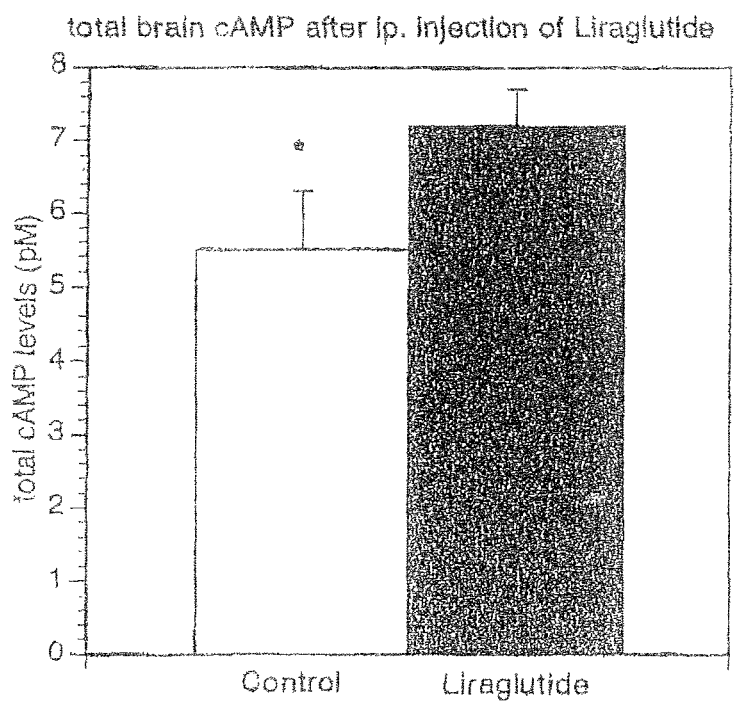

FIG. 3. (A) Injection of 25 nmol/kg bw liraglutide ip. 30 min before analysis showed a significant increase of cAMP in the brain compared to controls ($p<0.05$; t-test). (B) Injection of 25 nmol/kg bw lixisenatide ip, 30 min before analysis showed a significant increase of cAMP in the brain compared to controls ($p<0.01$; t-test). (C) When directly comparing the effects of liraglutide with lixisenatide, a significant difference between drugs is found ($p<0.05$; t-test).

Figure 4:
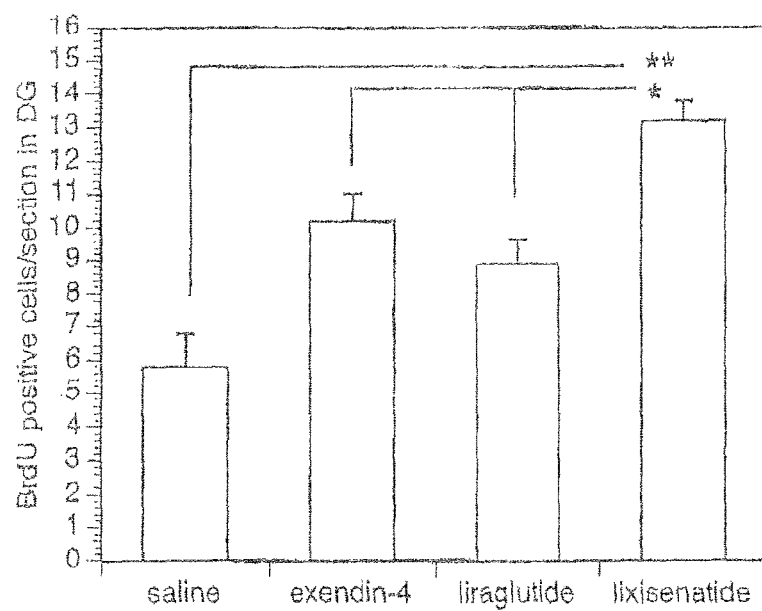

FIG. 4. Effect of once-daily injection of either exendin-4, liraglutide or lixisenatide 25 nmol/kg bw. for 3 weeks on cell proliferation in the dentate gyrus (BrdU staining). Values are the mean±S.E.M. $*p<0.05$, $**p<0.01$. Lixisenatide shows an increased cell proliferative activity compared to exendin-4 and liraglutide ($p<0.05$) and controls ($p<0.01$).

Figure 5:
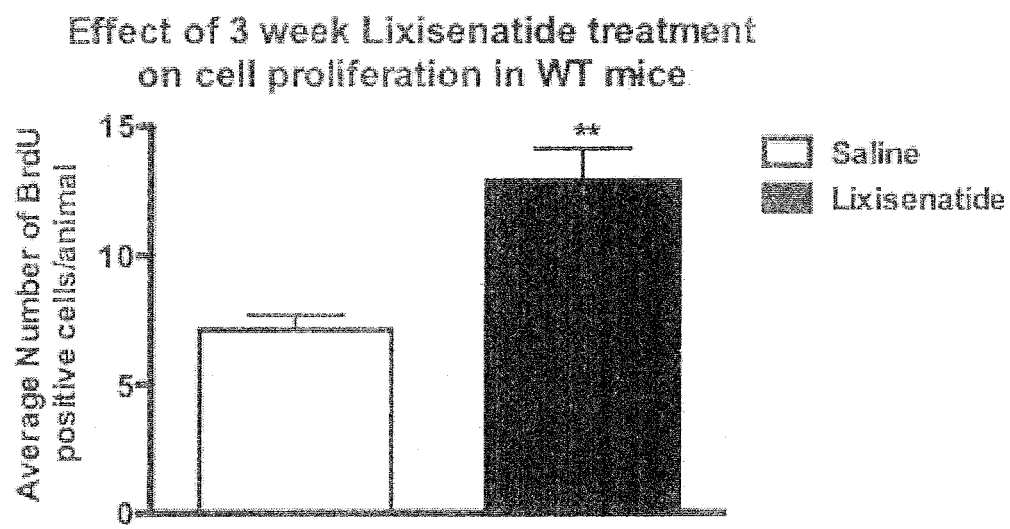

FIG. 5. Histological analysis of chronic injection of lixisenatide ip. once-daily for 3 weeks (25 nmol/kg bw ip.). In a BrdU immuno-histological analysis, more new cells were found in the dentate gyrus brain area. Also, more young neurons were found (double cortin stain). Values are the mean±S.E.M. $*=p<0.05$, $**=p<0.01$.

FIG. 6. (A) LDH Assay. Pre-treatment of SH-SY5Y cells with lixisenatide followed by Methyl Glyoxal Stress. ($***<0.0001$). A dose of 10 nM lixisenatide was sufficient in protecting cells from 1200 μM Methyl Glyoxal stress. (B) LDH Assay. Pre-treatment of SH-SY5Y cells with liraglutide followed by Methyl Glyoxal Stress. $*p<0.05$. $p<0.001$, $*p<0.0001$). A dose of 200 nM liraglutide was sufficient in protecting cells from 1200 μM Methyl Glyoxal stress. The lower doses of 10 nM or 100 nM showed no effect.

FIG. 7. Post-Stress treatment with Lixisenatide or Liraglutide after Methyl Glyoxal (MG) and Hydrogen Peroxide ($H_2O_2$) treatment. The X-axis refers to various assay conditions and the Y-axis represents the absorbance. $*=p<0.05$, $**=p<0.01$. (A) Lixisenatide post-treatment, (B) Liraglutide post-treatment.

FIG. 8. Pre-treatment with Lixisenatide or Liraglutide followed by Methyl Glyoxal (MG) stress. The X-axis refers to various assay conditions and the Y-axis represents the absorbance. $*=p<0.05$, $***=p<0.001$. Pre-treatment effect of (A) Lixisenatide, (B) Liraglutide and (C) Exendin-4.

Figure 9:
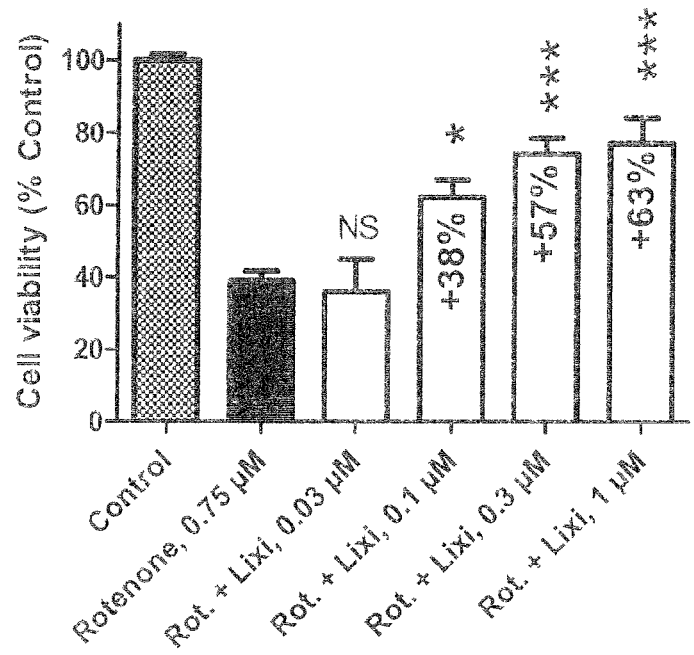

FIG. 9. Neuroprotection of LUHMES cells (expressed as percentage reversal of the normalized cell viability decrease induced by rotenone exposure) in the presence of various concentrations of Lixisenatide. Rot.=rotenone. NS=not significant; $*=p<0.05$; $***=p<0.001$.

Figure 10:
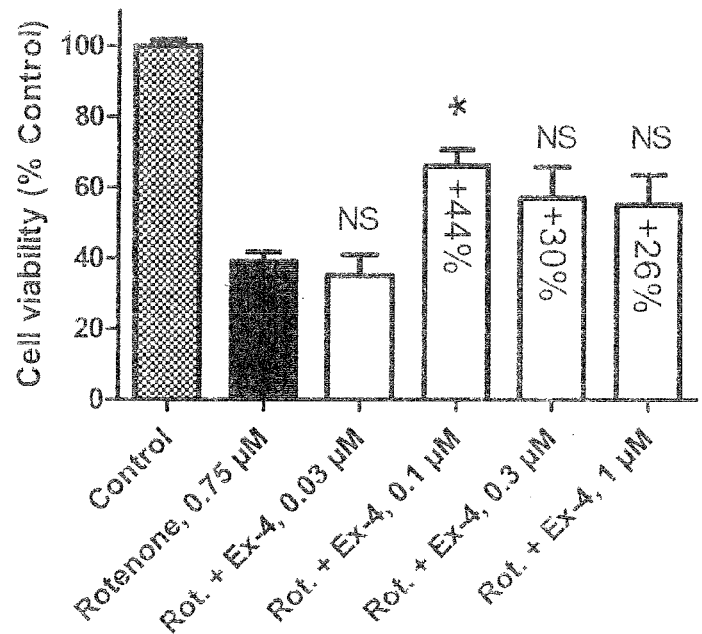

FIG. 10. Neuroprotection of LUHMES cells (expressed as percentage reversal of the normalized cell viability decrease induced by rotenone exposure) in the presence of various concentrations of Exendin-4/Exenatide. Rot.=rotenone. NS=not significant. $*=p<0.05$.

Figure 11:
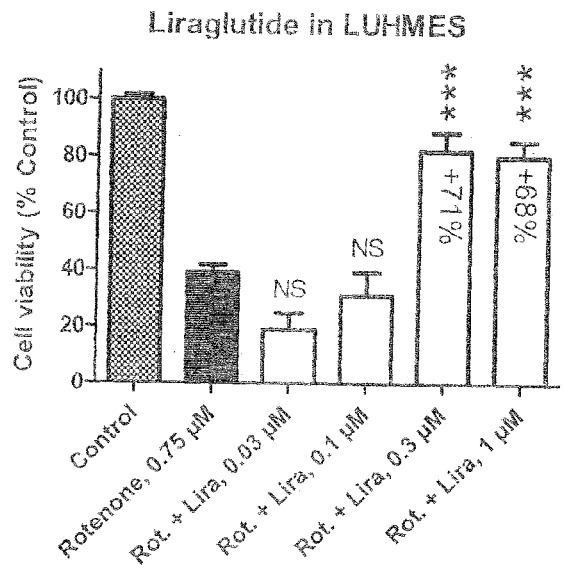

FIG. 11. Neuroprotection of LUHMES cells (expressed as percentage reversal of the normalized cell viability decrease induced by rotenone exposure) in the presence of various concentrations of Liraglutide. Rot.=rotenone. NS=not significant; $***=p<0.001$.

Figure 12:
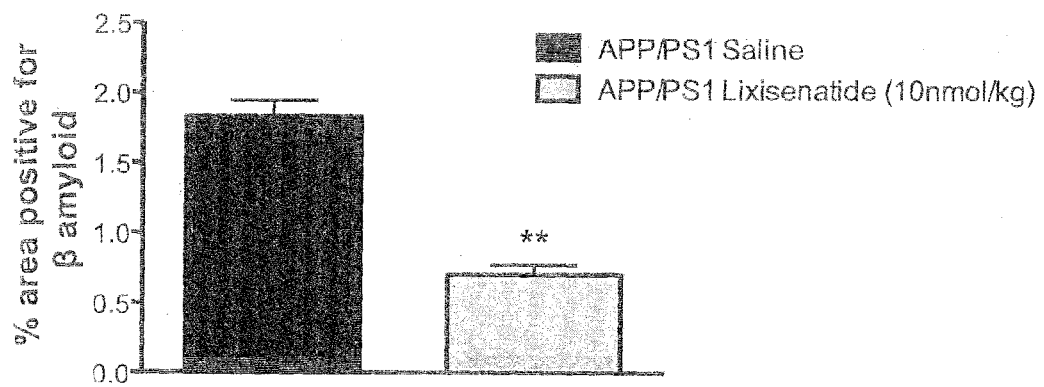

FIG. 12. Lixisenatide treatment reduces amyloid plaque load in the brain of Alzheimer's Disease transgenic mice, Lixisenatide treatment in 7-month old APP/PS1 transgenic mice for 70 days (10 nmol/kg, i.p., daily) reduces beta amyloid plaque load in the brain as quantified by beta amyloid immunohistochemistry and determination of the % area positive for β amyloid in cross sections of the brain cortex. Values are mean+/−SEM ($**=p<0.01$).

Figure 13:
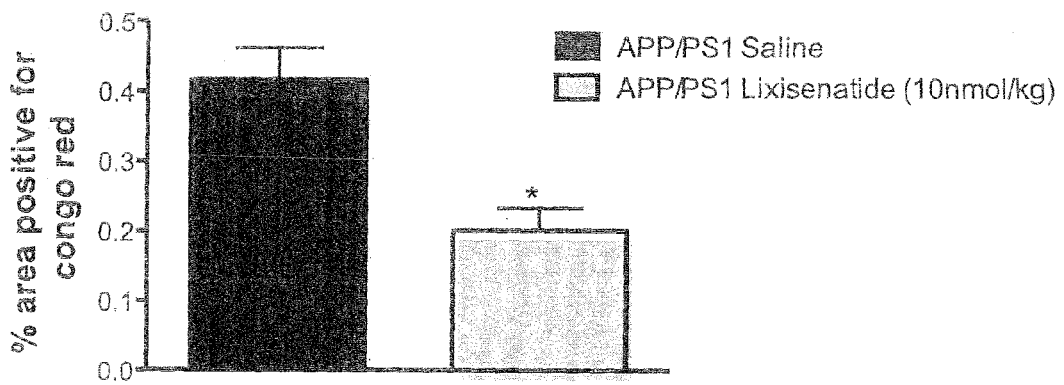

FIG. 13. Lixisenatide treatment reduces amyloid plaque load in the brain of Alzheimer's Disease transgenic mice. Lixisenatide treatment in 7-month old APP/PS1 transgenic mice (Alzheimer's disease model) for 70 days 10 nmol/kg, i.p., daily) reduces mature amyloid plaque load in the brain as quantified by histological staining with Congo red and determination of the % area positive for Congo red in cross sections of the brain cortex. Values are mean+/−SEM ($*=p<0.05$).

EXAMPLE 1

Lixisenatide is a peptide drug which typically is administered parenterally. To elicit an activity against neurodegenerative diseases, such as Alzheimer's disease, Parkinson's disease, progressive supranuclear palsy, multiple system atrophy, Lewy body dementia, Parkinson's disease dementia or stroke, lixisenatide must cross the blood-brain-barrier. Lixisenatide, in particular when administered parenterally, is suitable for the treatment or/and prevention of neurodegenerative diseases if lixisenatide provides one or more of the following features:

(a) lixisenatide can cross the blood brain barrier,
(b) lixisenatide activates GLP-1 receptors in the brain and induces physiological effects by receptor activation,
(c) lixisenatide provides disease-modifying effects in suitable models,
(d) lixisenatide is neuroprotective in suitable models, and
(e) lixisenatide provides advantages over other GLP-1 receptor agonists, such as liraglutide or exenatide.

Lixisenatide Uptake by the Brain

In the present Example, it is described whether the GLP-1 receptor agonist lixisenatide crossed the blood-brain-barrier (BBB). 3 doses (2.5 nmol/kg bw, 25 nmol/kg bw and 250 nmol/kg bw, ip.) were tested, and the levels found in mouse brain tissue 30 min and 3 h post injection were examined. Lixisenatide levels were enhanced 30 min after delivery with all doses and were also detected with both the low (2.5 nmol/kg bw) and medium level (25 nmol/kg bw), but not the high dose of 250 nmol/kg bw of lixisenatide. This difference suggests that transport of lixisenatide into the brain is regulated, limiting the influx of high concentrations of lixisenatide tested here (FIG. 1).

Comparison of Lixisenatide Uptake with Liraglutide Uptake in the Brain

The above results for lixisenatide were compared to those for the GLP-1 agonist, liraglutide (Victoza by Novo Nordisk). As discussed above and shown in FIGS. 1 and 2, lixisenatide levels showed significant increase in the brain at the lowest dose of 2.5 nmol/kg bw ip., whereas liraglutide did not show an increase at this dose (FIG. 2), suggesting that lixisenatide is taken up into the brain at lower concentrations than liraglutide.

From this finding it is concluded that lixisenatide requires a lower dose of lixisenatide to pass the blood-brain-barrier, compared with liraglutide, so that it can exert a therapeutic effect upon neurodegenerative diseases, as described herein, at a lower dose, compared with liraglutide.

GLP-1 Receptor Activation in the Brain/Production of cAMP

Preliminary studies have shown that lixisenatide activates the pancreas GLP-1 receptor that is linked to the enhancement of the cAMP levels (for review, see, for example, Doyle et al., 2007)

Figure 3B:
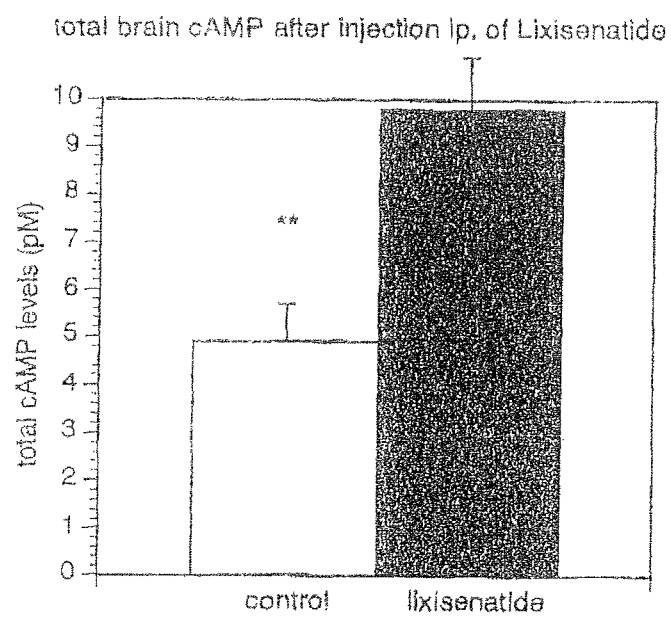
Figure 3C:
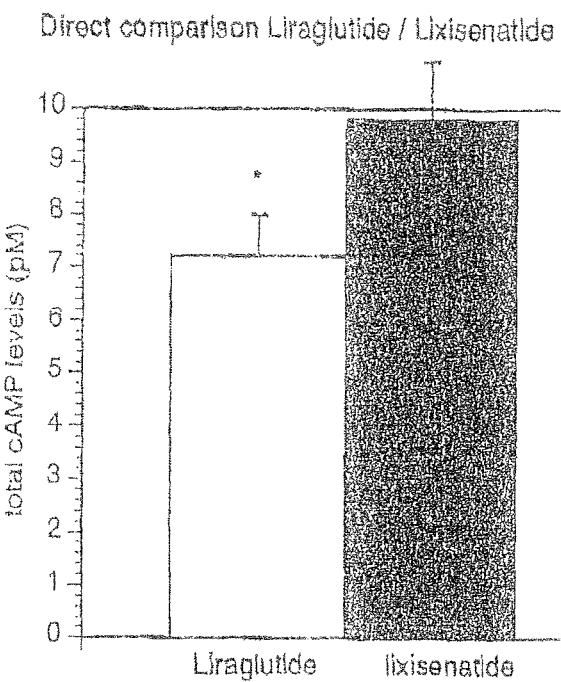

In the present example, it has been shown for the first time that injecting lixisenatide i.p. increased the amount of cAMP in the brain, indicating that the lixisenatide activates GLP-1 receptors in the brain (FIG. 3b). A direct comparison of the effects of lixisenatide (25 nmol/kg bw i.p.) and liraglutide (25 nmol/kg bw i.p., for results, see FIG. 3a) on GLP-1 receptor is shown in FIG. 3c. Lixisenatide produces significantly higher levels of cAMP than liraglutide (*=$p<0.05$) at the same dose, demonstrating a higher effectiveness of lixisenatide.

Neurogenerative Effects/Disease-Modifying Effects of Lixisenatide in the Brain

The effects of chronic injection of lixisenatide i.p., exendin-4 i.p. and liraglutide i.p. for 3 weeks upon neuronal progenitor stem cell proliferation was investigated. An enhanced stem cell proliferation in the dentate gyrus was found (BrdU stain, FIGS. 4 and 5). Surprisingly, lixisenatide had significantly enhanced cell proliferation (*=$p<0.05$) when compared with exendin-4 or liraglutide, indicating that lixisenatide is more effective in the brain than exendin-4 and liraglutide when injected at the same dose.

In addition, the number of young neurons in the dentate gyrus was increased after lixisenatide injection when compared to liraglutide (double cortin stain, data not shown), indicating that the progenitor cells differentiate into neurons. This demonstrates that lixisenatide induces lasting improvements.

These effects of lixisenatide on stem cells (proliferation and differentiation) are an important aspect for brain repair, so these effects can provide a disease-modifying effect in neurodegenerative diseases, such as Alzheimer's disease, Parkinson's disease, and stroke.

Neuroprotective Effects of Lixisenatide in the Brain

In neuronal cell culture studies, lixisenatide has been tested to investigate if it has neuroprotective effects in cellular stress conditions. The toxic drug Methyl Glyoxal was used to reduce cell viability. Addition of lixisenatide showed neuroprotective effects in a dose-dependent manner (FIG. 6a), affording 100% protection at all doses with the lowest concentration of Methyl Glyoxal and maintaining protection even with the highest concentration of Methyl Glyoxal tested. A dose of 10 nM lixisenatide was sufficient in protecting cells from 1200 µM Methyl Glyoxal stress.

Figure 6A:
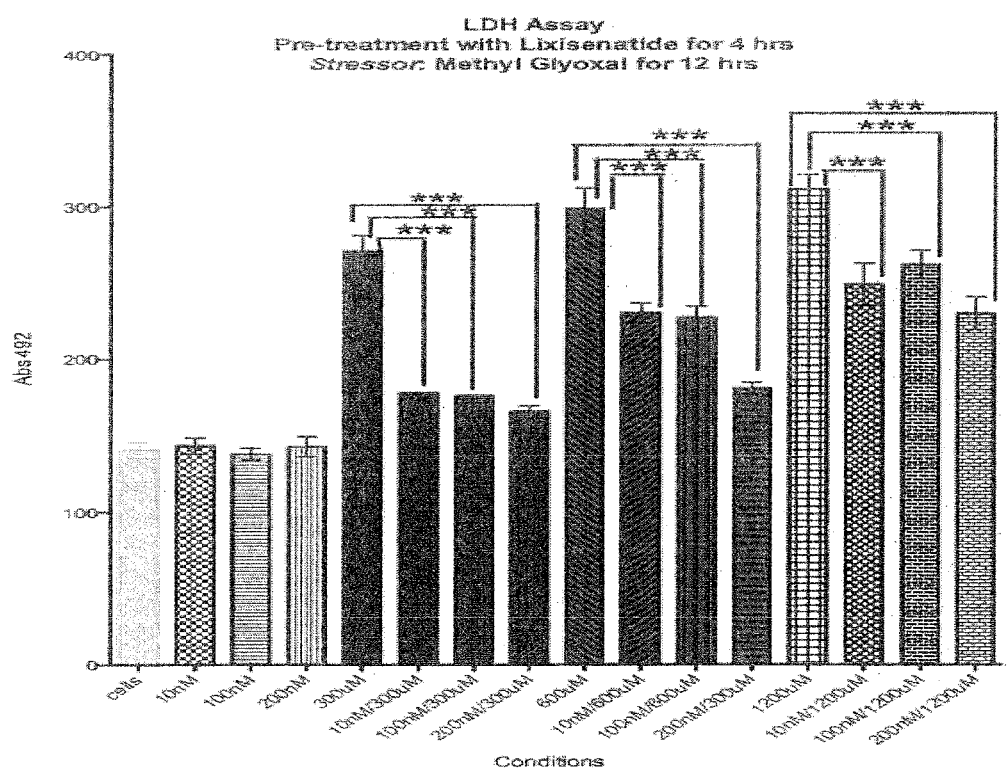
Figure 6B:
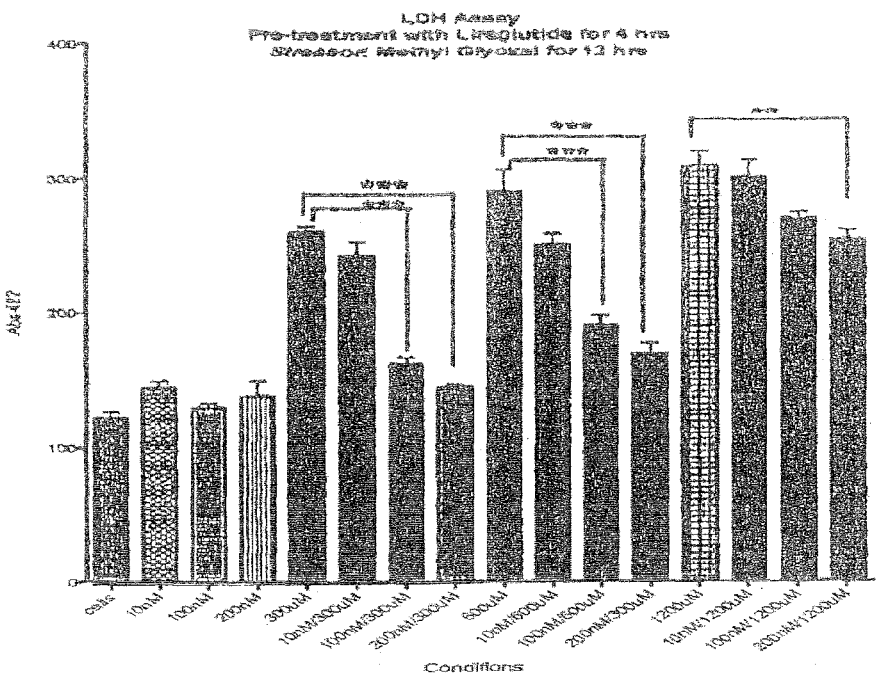

In addition, lixisenatide showed superior protection compared with liraglutide. In FIG. 6b, it is shown that liraglutide was not able to protect cells at a does of 10 nM. A dose of 200 nM liraglutide was required in order to protect the cells from 1200 µM Methyl Glyoxal stress, the lower doses of 10 or 100 nM showed no effect.

Materials and Methods

Measurement of cAMP in the Brain

Animals

Female wild type (C57BL/6 background) mice were used, 5 per group. For cAMP measurement, mice were injected i.p. with 25 nmol/kg body weight (bw) liraglutide, lixisenatide or saline (0.9% w.v.) as control in two separate experiments. 30 min post injection mice brains were immediately removed and snap frozen.

Tissue Extraction of cAMP

Each brain was extracted using 0.1 M HCl. 10 ml of 0.1 M HCl per g of tissue was added. Samples were sonicated then centrifuged at 10,000 rpm for 15 min at 4° C. The supernatant was poured off and used directly for measurement by direct cAMP ELISA kit (Enzo Life Sciences). Dilutions were made using the 0.1 M HCl provided in the kit.

Immunohistochemistry

Animals were administered BrdU (180 mg/kg bw; i.p.) 18 h prior to being anaesthetized with pentobarbitone (0.3 ml; Euthanal, Bayer AG, Leverkusen, Germany) and perfused transcardially with PBS followed by 4% paraformaldehyde. The brains were removed and put into 30% sucrose in PBS overnight. Immunohistochemistry for BrdU or doublecortin (DCX) was performed on 45 µm free floating sections. Endogenous peroxidase activity was quenched by incubation of sections in 3% hydrogen peroxide. Denaturation of DNA involved incubation in 2N HCl, followed by 0.1 M borax for 10 min. Sections were incubated in a primary antibody for BrdU (1:200, mouse rnonoclonal anti-BrdU, Sigma) or for DCX gout polyclonal anti-doublecortin (1:200, Santa Cruz, USA, sc-710) overnight at 4° C. Then secondary antibody (1:200, horse anti-mouse, Vector elite ABC kit, mouse, Vector laboratories) was applied. Sections were incubated in an avidin biotin enzyme reagent and incubated in Vector SG substrate chromogen (see Gengler et al. 2010) for details.

Microscopy

The sections were analysed using an Olympus CX 40 microscope, using stereological techniques. This involves starting the sectioning randomly and collecting every 5$^{th}$ section throughout the granule cell layer (GCL) of the dentate gyrus (DG). Analysis was performed using a ×40 objective and representative images were taken using a 5.1 MPix digital camera. For each drug group, 4-6 mice brains were analysed. Between 8 and 12 sections were taken for each brain. The brain regions analysed ranged from −1.3 to −2.5 mm bregma. All positive cells in the DG were counted using ImageJ software (freeware of the NIH). In the GCL, cells positive for BrdU or DCX were counted.

SH-SY5Y Cell Line

SH-SY5Y is a thrice-cloned human neuroblastoma cell line that was established in 1970 from a bone marrow biopsy of a metastatic neuroblastoma site in a four year-old female. These cells are dopamine beta hydroxylase active, acetylcholinergic, glutamatergic and adenosinergic. SH-SY5Y cells grow as a mixture of floating and adherent cells as well as form clusters of neuroblastic cells with multiple, short, fine cell processes. Retinoic acid and cholesterol treatment can force the cells to grow dendrites and differentiate.

Pre-Treatment of SH-SY5Y Cells with Lixisenatide or Liraglutide Followed by Methyl Glyoxal Stress SH-SY5Y cells were cultured in Dulbecco's minimum essential medium with F12 (1:1) and Glutamax supplemented with 10% heat inactivated (heated at 56° C. for 20 min) fetal bovine serum and penicillin and streptomycin, and incubated in a humidified, 5% $CO_2$, 37° C. incubator. Cells were trypsinized at 80% confluency and after counting cells by trypan blue exclusion method (Countess, Invitrogen), $2 \times 10^4$ cells were plated in Laminin coated 96-well plate (Nunc, Inc) at 95% cell viability. After 12 hours of cell attachment, cells were pre-treated with lixisenatide or liraglutide at different doses as at 10 nM, 100 nM and 200 nM, followed by the addition of stressor Methyl Glyoxal in the serum free media at concentrations 300 µM, 600 µM (and 1200 µM (FIGS. 6A and 6B). Data was analyzed by PRISM 5.0C (GraphPad Software, Inc.) and significance was defined as p values of <0.05 or smaller.

Effect of Lixisenatide or Liraglutide Pre-Treatment on Hydrogen Peroxide Stressed SH-SY5Y Cells Cells were pre-treated with 10 nM and 100 nM liraglutide or lixisenatide, followed by the addition of stressor hydrogen peroxide in the serum free media at concentrations 200 µM, 400 µM and 800 µM.

LDH Assay

Cell culture media were analysed using a sensitive lactate-dehydrogenase (LDH) assay (by Sigma). The LDH assay provides a measure of the number of dead cells via total cytoplasmic LDH or by membrane integrity as a function of the amount of cytoplasmic LDH released into the medium. The measurement of released LDH is based on the reduction of NAD by the action of LDH. The resulting reduced NAD (NADH) is used in the stoichiometric conversion of a tetrazolium dye. The final colored compound is measured by colorimetry.

Summary

The data of the present example demonstrates that lixisenatide is suitable for the treatment or/and prevention of neurodegenerative diseases, such as Alzheimer's disease, Parkinson's disease, progressive supranuclear palsy, multiple system atrophy, Lewy body dementia, Parkinson's disease dementia or stroke. Furthermore, lixisenatide has superior properties compared to the GLP-1 analog liraglutide and to exendin-4, both of which are currently used as treatments for type 2 diabetes.

In particular, the data of the present example demonstrates that (a) surprisingly, lixisenatide can cross the blood brain barrier. The data of the present invention indicate that the transport is regulated, as the transport rate at high concentrations is limited to a maximum level. Furthermore, lixisenatide is taken up into the brain at a lower parenteral dose as compared with liraglutide.

(b) lixisenatide activates GLP-1 receptors in the brain and induces cAMP production. Surprisingly, lixisenatide produces higher levels of cAMP than liraglutide, demonstrating higher effectiveness at activating the GLP-1 receptor at the same dose.

(c) lixisenatide can induce proliferation of progenitor cells in the dentate gyrus. Compared with exendin-4 or with liraglutide, lixisenatide surprisingly provides enhanced effects when administered at the same dose. In neurodegenerative diseases, these effects can constitute a disease-modifying effect.

(d) surprisingly, lixisenatide showed superior neuroprotective effects (against cellular stress) in the dentate gyrus when compared with liraglutide.

(e) surprisingly, a pre-treatment with a dose of 10 nM lixisenatide was sufficient in protecting SH-SY5Y neuroblastoma cells from 1200 µM Methyl Glyoxal stress. A dose of 200 nM liraglutide was necessary in protecting cells from 1200 µM Methyl Glyoxal stress, indicating that a lower dose of lixisenatide is sufficient to induce protection.

EXAMPLE 2

Post-Stress Treatment with Lixisenatide or Liraglutide after Methyl Glyoxal (MG) and Hydrogen Peroxide ($H_2O_2$) Treatment SHSY-5Y cells were seeded in 96 well plates and after 12 hours of serum starvation, were stressed with 600 µM and 1 mM of $H_2O_2$ and 1 mM and 2 mM of MG for 3 hrs. The cells were treated with 0, 1, 10, 50 and 100 nM of Lixisenatide and 0, 10, 50, 100 and 200 nM of Liraglutide. After 24 hrs 50 µL of XTT reagent was added and incubated for 8 hrs. The assay volume was 100 µL.

Figure 7A:
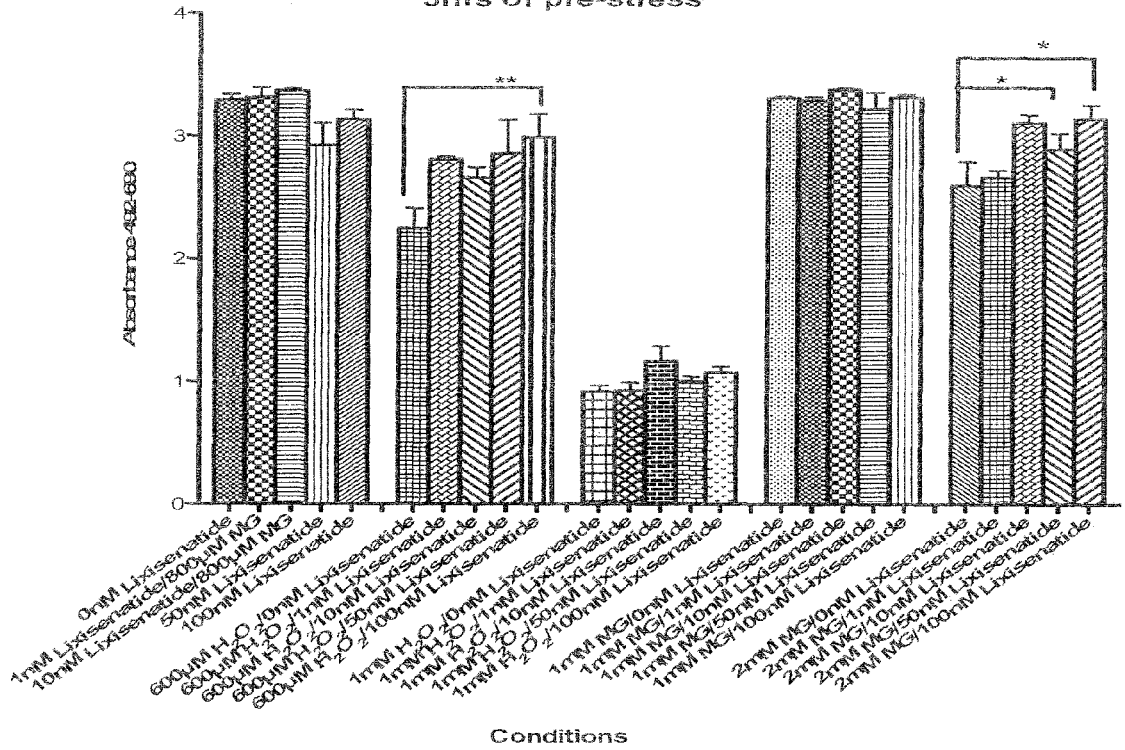
Figure 7B:
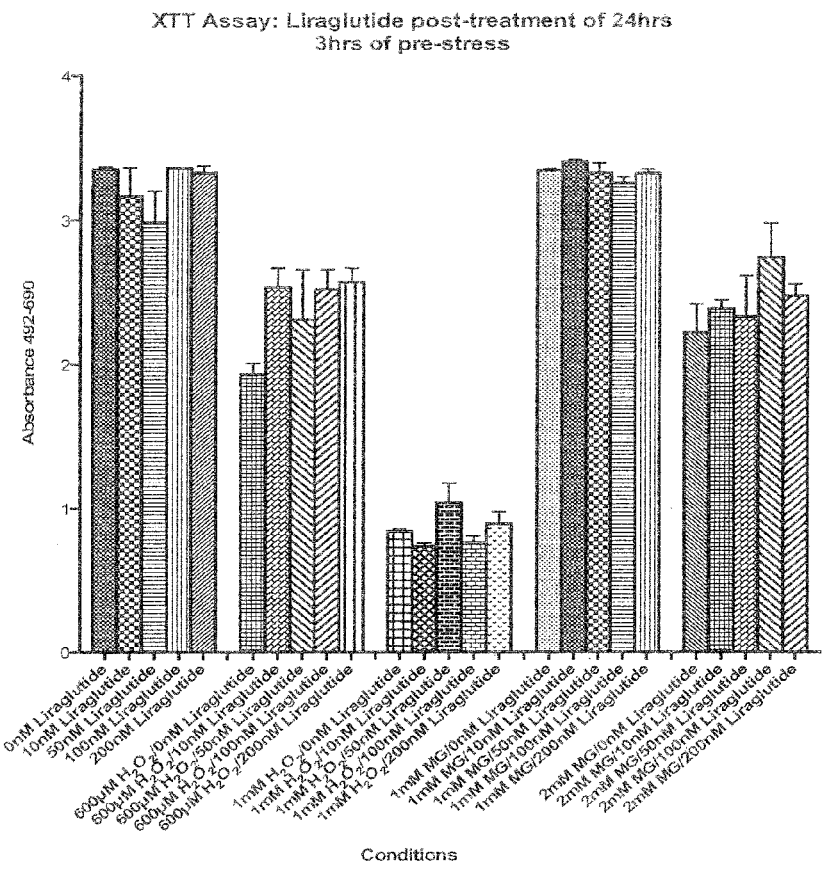

FIG. 7 demonstrates that the posttreatment with Lixisenatide significantly increased the number of surviving cells after stress with MG or $H_2O_2$ in a dose-dependent way (see in particular data obtained with 600 µM $H_2O_2$, and 2 mM MG in FIG. 7A). Liraglutide did not protect cells from the stress by MG or $H_2O_2$ (FIG. 7B).

Pre-Treatment with Lixisenatide or Liraglutide Followed by Methyl Glyoxal (MG) Stress SHSY-5Y cells were seeded in 96 well plates and after 12 hours of serum starvation and were treated with 0, 1, 10, 50 and 100 nM of Lixisenatide and 0, 10, 50, 100 and 200 nM of Liraglutide and Exendin-4 for 4 hrs, after being stressed with 400 µM and 600 µM of MG for 14 hrs. 50 µL of XTT reagent was added and plates incubated for 8 hrs.

Figure 8A:
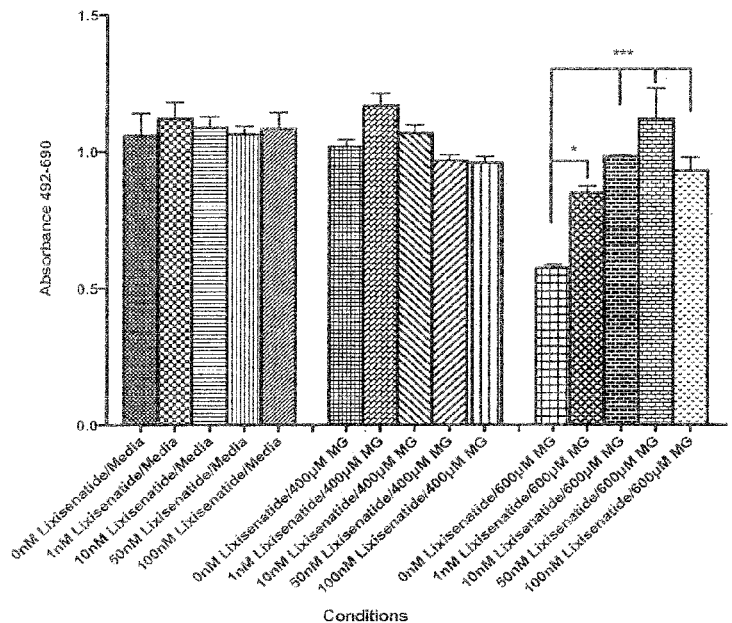
Figure 8B:
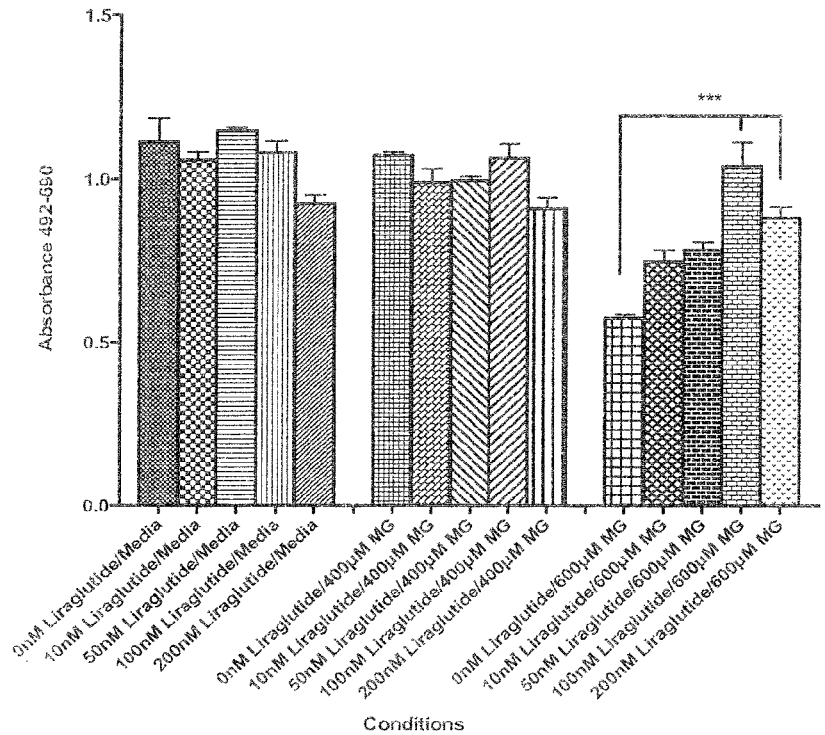
Figure 8C:
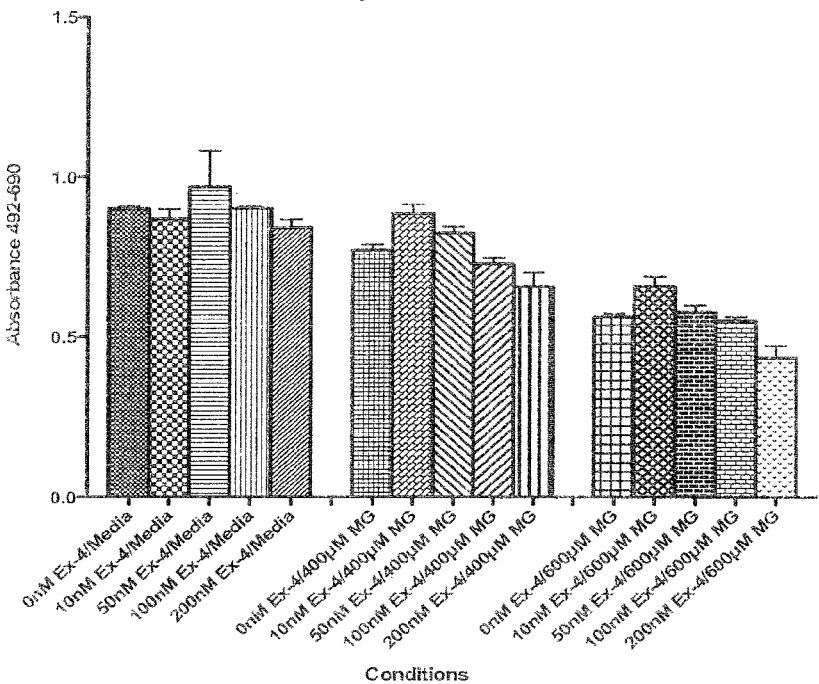

FIG. 8 demonstrates that the pre-treatment with Lixisenatide before stress with MG or $H_2O_2$ significantly increased the number of surviving cells in a dose-dependent way, starting with the lowest dose of 1 nM with best results at 50 nM (FIG. 8A). Liragutide also protected the cells, but only at a higher dose of 100 nM (FIG. 8B). Exendin-4 did not protect cells from the stress by MG or $H_2O_2$ (FIG. 8C).

Material and Methods

Pre-Treatment Assay with SHSY-5Y Cells Using Methyl Glyoxal as Stressor

1. SHSY-5Y cells were maintained in DMEM+F12 Glutamax media (Cat No. 313310, Invitrogen Inc.) with 10% FBS (Cat No. 10437, Invitrogen Inc.) and 1% Penn Strep (Cat No. 15070063, Invitrogen Inc.).

2. 80-90% confluent cultures were trypsinized using 0.25× trypsin EDTA solution and were seeded in 96 well plates (Cat No. 55301, Orange Scientific) which were previously coated with Laminin (L2020, Sigma) at a concentration of 1 µg/cm² for 2 hours at 37° C. in a $CO_2$ incubator and were washed 2 times with sterile double distilled water.

3. After 12-15 hours media was changed from 10% FBS containing to serum free media (SFM) for next 12 hours.

4. Cells were pre-treated with incretins for 4 hours, the assay was performed in 150 µl volume format of different concentrations and fresh SFM was added to the controls respectively, for 4 hrs.

5. The wells were washed with 1×HBSS and 150 µl of 600 µM Methyl Glyoxal (Cat No. M0252, Sigma) and SFM was added to the test wells and controls respectively for 12 hrs.

6. The supernatant was collected to perform the LDH assay and stored at −20° C.
7. 75 µl of XTT solution (Cat No. 11465015001, Roche Inc.) (Containing the coupling reagent) was added to the remaining cells and incubated at 37° C. for 4 hours. The assay is based on the ability of metabolic active cells to reduce the tetrazolium salt XTT to colored compounds which can be determined by absorbance measurement. An increased absorbance indicates an increased number of metabolic active cells.
8. Absorbance was obtained by measuring at 492 nm and 690 nm for each well and subtracting $A_{690}$ from $A_{492}$.
9. For the LDH (Cat No. G1780, Promega) assay the 50 µl of the supernatant was added to a 96 well plate along with 50 µl of the substrate and incubated in dark at room temperature for 60 minutes.
10. 50 µl of Stop solution was added and the absorbance measured at 490 nm.
11. The data for XTT and LDH assays was analyzed using Prism V.

Summary

The data of example 2 demonstrates that lixisenatide is suitable for the treatment or/and prevention of neurodegenerative diseases, such as Alzheimer's disease, Parkinson's disease, progressive supranuclear palsy, multiple system atrophy, Lewy body dementia, Parkinson's disease dementia or stroke. Furthermore, lixisenatide has superior properties compared to the GLP-1 analogs liraglutide and exenatide.

A pre-treatment with a dose of 10 nM lixisenatide was sufficient in protecting SH-SY5Y neuroblastoma cells from 600 µM Methyl Glyoxal stress. A dose of 100 nM-200 nM liraglutide was sufficient in protecting cells from 600 µM Methyl Glyoxal stress, indicating that a lower dose of lixisenatide is sufficient to induce protection. Lixisenatide is thus suitable for the prevention of the diseases as indicated above. These data are in line with the data obtained in Example 1 (FIGS. 6A and B), demonstrating that lixisenatide showed superior neuroprotective effects (against cellular stress) in SH-SY5Y neuroblastoma cells when compared with liraglutide.

Furthermore, a post-treatment with lixisenatide was sufficient in protecting SH-SY5Y neuroblastoma cells after from 2 mM Methyl Glyoxal stress or 1 mM $H_2O_2$ stress. In contrast, Liraglutide did not protect cells from the stress by MG or $H_2O_2$.

EXAMPLE 3

Treatment with the Glucagon-Like peptide-1 Receptor (GLP-1R) Agonist Lixisenatide Protects Human Neuronal Cells Against Rotenone Toxicity In this Example, neuroprotection experiments in cellular models are described supporting the use of Lixisenatide in the treatment of Parkinson's disease, Parkinson's disease dementia, progressive supranuclear palsy, multiple system atrophy, and Lewy body dementia. The Example demonstrates that Lixisenatide could slow-down, arrest or reverse the progression of Parkinson's disease, Parkinson's disease dementia, progressive supranuclear palsy, multiple system atrophy, and Lewy body dementia by protecting the neurons vulnerable in this disease. These diseases are associated with loss of neurons utilizing dopamine as neurotransmitter.

The Example refers to in vitro cultures assays using a human cell line that is being dopaminergic in nature called Lund Human Mesencephalic neurons (LUHMES cells). These cells are described in Lotharius et al. (2002). Cultures from these cells were exposed in vitro to rotenone known to kill dopaminergic cells and to be associated with Parkinson's disease upon accidental or environmental exposure to humans. The association of rotenone with Parkinson's disease is described in Sherer et al., 2003 and Tanner et al., 2011. Rotenone can cause parkinsonism by killing dopamine-producing neurons and thereby experimentally reproducing the major features of the human Parkinson's disease.

In the present Example, the glucagons-like peptide-1 receptor (GLP-1R) agonist Lixisenatide exhibits significant neuroprotective effects in LUHMES cells against neurodegeneration induced by rotenone (FIG. 9). Lixisenatide provides advantages compared with other GLP-1 receptor (GLP-1R) agonists. The neuroprotective effect of Lixisenatide against rotenone in LUHMES cells is significantly active at 3-fold lower concentrations than Liraglutide (FIGS. 9 and 11), a result comforting the unexpected superior activity effect of Lixisenatide seen previously in the Methyl Glyoxal model of Example 1.

Exenatide does not induce an improved viability at a concentration of 0.3 µM or 1 µM. In contrast, Lixisenatide provides a significant improvement of viability at these concentrations (FIGS. 9 and 10).

Material and Methods

To assess neuroprotection against rotenone, LUHMES cells were grown at 37° C. in a humidified 95% air, 5% $CO_2$ atmosphere in standard cell-culture media. After 2 days culture in plastic flasks, differentiation medium containing growth factors was added and cells were incubated for another 2 days. Cells were dissociated and seeded into coated multi-well plates and fresh differentiation medium was added for another 4 days. On day 6 of differentiation, cells were treated with various concentrations of Lixisenatide, Exenatide (Exendin-4) or Liraglutide 1 hour before treatment with rotenone (0.75 µM). Neuroprotection was measured after 72 hrs. with a resazurin-based assay, an indicator of metabolically active cells generating a fluorescent product through cellular oxidation-reduction. The fluorescence produced is proportional to the number of viable cells in the cultures and thus measures the degree of protection of the neuronal LUHMES cells provided by the treatments. Data from n=12 measurements were compared following normalization of cell viability readings with respect to controls without rotenone. A one-way analysis of variance followed by a Dunnett's test was used for statistical comparisons between experimental groups. Values of $p<0.05$ were considered as significant and denoted in the graphs with asterisks as follows: *=$p<0.05$; =$p<0.01$; *=$p<0.001$; NS=not significant. Neuroprotection was expressed as percent reversal of viability decrease induced by rotenone.

Summary

The data of example 3 demonstrates that lixisenatide is suitable for the treatment or/and prevention of neurodegenerative diseases, such as Parkinson's disease, progressive supranuclear palsy (PSP), multiple system atrophy (MSA), Lewy body dementia, Parkinson's disease dementia or stroke. Furthermore, lixisenatide has superior properties compared to the GLP-1 analog liraglutide and to exendin-4.

In the present Example, Lixisenatide exhibits significant neuroprotective effects in LUHMES cells against neurodegeneration induced by rotenone (FIG. 9). Lixisenated provides advantages compared with other GLP-1 receptor (GLP-1R) agonists. In rotenone treated LUHMES cells, Lixisenatide is significantly active at 3-fold lower concentrations than Liraglutide. At a concentration of 0.3 µM or 1 µM Exenatide, no significant effect could be observed. In contrast, Lixisenatide provides a dose-dependent improvement of viability at these concentrations.

EXAMPLE 4

The Effect of Lixisenatide in $APP_{swe}/PS1_{\Delta E9}$ Transgenic Mice

To further demonstrate the interest of lixisenatide for the treatment of neurodegenerative diseases such as Alzheimer's Disease, in the present example, it is described the effect of lixisenatide treatment in transgenic mice bearing amyloid plaques in their brain. $APP_{swe}/PS1_{\Delta E9}$ transgenic mice are a well characterized model of Alzheimer's disease showing an amyloid brain pathology. Lixisenatide treatment (10 nmol/kg, i.p., daily) was initiated in 7-month old APP/PS1 transgenic mice at an age when amyloid plaques have already developed in the brain and lasted for 70 days.

Transgenic Animals $APP_{swe}/PS1_{\Delta E9}$ mice with a C57Bl/6 background were obtained from the Jackson lab (Bar Harbor, Me., USA). Heterozygous males were bred with wild-type C57/Bl6 females bought locally (Harlan, UK). Offspring were ear punched and genotyped using PCR with primers specific for the APP-sequence (Forward "GAATTCCGACATGACTCAGG, SEQ ID NO:4", Reverse: "GTTCTGCTGCATCTTGGACA, SEQ ID NO:5"). Mice not expressing the transgene were used as wild-type controls. Male animals were used in all studies. Animals were caged individually and maintained on a 12/12 light-dark cycle (lights on at 08 h00, off at 20 h00), in temperature-controlled room (T:21.5° C.±1). Food and water were available ad libitum. Animals were handled daily for two weeks prior to commencement of the study.

Treatment with Lixisenatide

Mice were 7 months of age when treatment began. At that time, mice already showed amyloid brain pathology. Mice were injected intraperitoneally (i.p.) once daily with Lixisenatide (10 nmol/kg body weight) or Saline (0.9% w/v) for 70 days. Experiments were licensed by the UK home office in accordance with the Animal (scientific procedures) Act of 1986.

Lixisenatide was supplied by Sanofi. Lyophylised peptide was reconstituted in Milli-Q water at a concentration of 1 mg/ml. Aliquots were stored in the freezer and reconstituted in 0.9% saline for injection.

Histological Preparation

Animals were perfused transcardially with PBS buffer followed by ice-cold 4% paraformaldehyde in PBS. Brains were removed and fixed in 4% paraformaldehyde for at least 24 h before being transferred to 30% sucrose solution overnight. Brains were then snap frozen using Envirofreez™ and coronal sections of 40-micron thickness were cut at a depth of −2 to −3 Bregma using a Leica cryostat. Sections were chosen according to stereological rules with the first section taken at random and every 6th section afterwards.

Using standard methods (see McClean et al. 2011 for details), beta amyloid was stained using rabbit polyclonal anti amyloid beta peptide (1:200, Invitrogen, UK, 71-5800), and dense core plaques were stained using congo red. Beta amyloid and congo red were analysed by taking 2 images (using a 10x objective) of cortex per section (with 7-10 sections per brain; n=6 for Lixisenatide 10 nmol/kg bw, n=12 for saline).

All staining was visualized by Axio Scope 1 (Zeiss, Germany) and analyzed using a multi threshold plug-in with Image J (NIH, USA).

Results

In $APP_{swe}/PS1_{\Delta E9}$ transgenic mice already bearing amyloid brain pathology at initiation of treatment, lixisenatide treatment for 70 days lead to a reduction of beta amyloid plaque load as measured by beta amyloid immunoreactivity by 62% (p<0.0039; repeated measures t-test), compared with Saline-treated mice (FIG. 12).

Similarly, lixisenatide treatment reduced dense core amyloid plaque load as quantified by Congo red histological staining by 52% (p=0.0419; repeated measures t-test) compared with respective Saline-treated APP/PS1 mice (FIG. 13).

The activity was observed at lower dose (10 nmol/kg) than previously described for liraglutide (25 nmolm/kg, McClean et al 2011).

Summary

These data using two independent techniques demonstrate that lixisenatide can reduce brain amyloid pathology in an animal model of Alzheimer's disease. The data demonstrates that lixisenatide is suitable for the treatment or/and prevention of neurodegenerative diseases, such as Alzheimer's disease by decreasing brain amyloid plaque pathology. Therefore in addition to its neuroprotective properties, lixisenatide can decrease pathological lesions such as amyloid plaques and represent therefore an attractive treatment or/and prevention for Alzheimer's disease. Furthermore, activity is achieved at dose lower than those previously described for the GLP-1 analog liraglutide as expected from the data of Example 1.

REFERENCES

1. Bertram L, Lill C M, and Tanzi R E, 2010. The Genetics of Alzheimer Disease: Back to the Future, *Neuron*, 68, 270-281.
2. Mancuso M, Orsucci D, LoGerfo A, Calsolaro V, Siciliano G, 2010, Clinical features and pathogenesis of Alzheimer's disease: involvement of mitochondria and mitochondrial DNA, *Adv Exp Med. Biol.*, 685, 34-44.
3. Varadarajan S, Yatin S, Aksenova M, and Butterfield D A, 2000, Review: Alzheimer's Amyloid b-Peptide-Associated Free Radical Oxidative Stress and Neurotoxicity, *Journal of Structural Biology*, 130, 184-208.
4. Higginsa G C, Beart P M, Shin Y S, Chene M J, Cheunge N S and Nagley P, 2010, Oxidative Stress: Emerging Mitochondrial and Cellular Themes and Variations in Neuronal Injury, *Journal of Alzheimer's Disease*, 20, S453-S473.
5. Wollen K A, 2010, Alzheimer's disease: the pros and cons of pharmaceutical, nutritional, botanical, and stimulatory therapies, with a discussion of treatment strategies from the perspective of patients and practitioners, *Altern Med. Rev.*, 15(3), 223-44.
6. Aderinwale O G, Ernst H W, Mousa S A, 2010, Current therapies and new strategies for the management of Alzheimer's disease, *Am J Alzheimers Dis Other Demen.*, 25(5), 414-24.
7. Kaduszkiewicz, H., Zimmermann T, Beck-Bornholdt H P, van den Bussche H (2005). Cholinesterase inhibitors for patients with Alzheimer's disease: systematic review of randomised clinical trials. BMJ 331: 321 doi: 10.1136/bmj.331.7512.321
8. Hölscher C, 2005, Development of Beta-Amyloid-induced neurodegeneration in Alzheimer's disease and novel neuroprotective strategies, *Reviews in Neuroscience*, 16, 181-212.

9. De Rosa, Garcia R, Braschi A A, Capsoni C, Maffei S, Berardi L, Cattaneo N, 2005, Intranasal administration of nerve growth factor (NGF) rescues recognition memory deficits in A D11 anti-NGF transgenic mice. Proc Natl Acad. Sci., 102, 3811-3816.
10. Hölscher C, Li L, 2010, New roles for insulin-like hormones in neuronal signaling and protection: New hopes for novel treatments of Alzheimer's disease? *Neurobiology of Aging,* 31, 1495-1502.
11. Hölscher C, (2010b), The role of GLP-1 in neuronal activity and neurodegeneration, *Vitamins and hormones,* 84, 331-54.
12. McClean P L, Parthsarathy V, Faivre E, Hölscher C (2011): The diabetes drug Liraglutide prevents degenerative processes in a mouse model of Alzheimer's disease. J. Neurosci., 31: 6587-6594.
13. Li H, Lee C H, Yoo K Y, Choi J H, Park O K, Yan B C. Byun K, Lee B, Hwang J K, Won M H (2010) Chronic treatment of exendin-4 affects cell proliferation and neuroblast differentiation in the adult mouse hippocampal dentate gyrus. Neurosci Lett 19: 1205-1219.
14. Li Y, Duffy K, Ottinger M, Ray B, Bailey J, Holloway H, Tweedie D, Perry T, Mattson M, Kapogiannis D, Sambamurti K, Lahiri D, Greig N (2010) GLP-1 Receptor Stimulation Reduces Amyloid-beta Peptide Accumulation and Cytotoxicity in Cellular and Animal Models of Alzheimer's Disease. J Alzheimers Dis 19:1205-1219.
15. Gandhi S, Wood N W (2005) Molecular pathogenesis of Parkinson's disease. Hum Mol Genet. 14: 2749-2755.
16. Schapira A H (2001) Causes of neuronal death in Parkinson's disease. Adv Neurol 86: 155-162.
17. Perry T, Lahiri D K, Chen D, Zhou J, Shaw K T Y, Egan J M, Grieg N H (2002) A novel neurotrophic property of glucagon-like peptide 1: a promoter of nerve cell growth factor mediated differentiation on PC12 cells. J Pharmacol exp 300: 958-966.
18. Perry T A, Haughey N J, Mattson M P, Egan J M, Grieg N N (2002) Protection and reversal of excitotoxic neuronal damage by glucagon-like peptide-1 and exendin-4. J Pharmacol Exp Ther 302: 881-888.
19. Harkavyi A, Abuirmeileh A, Lever R, Kingsbury A E, Biggs C S. Whitton P S. (2008) Glucagon-like peptide I receptor stimulation reverses key deficits in distinct rodent models of Parkinson's disease. J Neuroinflamm 5: 19, 1-9.
20. Li A, Perry T A, Kindy M S, Harvey B K, Tweedie D, Holloway H W, Powers K, Shen H, Egan J M, Sambamurti K, Brossi A, Lahiri D K, Mattson M P, Hoffer B J, Wang Y, Greig N H (2009) GLP-1 receptor stimulation preserves primary cortical and dopaminergic neurons in cellular and rodent models of stroke and Parkinsons. PNAS106: 4 1285-1290.
21. Martin B, Golden E, Carlson O D, Pistell P, Zhou J, Kim W, Frank B P, Thomas S, Chadwick A, Greig N H, Bates G P, Sathasivam K, Bernier M, Maudsley S, Mattson M P, Eagn J M (2009) Exendin-4 improves glycemic control, ameliorates brain and pancreatic pathologies and extends survival in a mouse model of Huntington's Disease. Diabetes 58: 2, 318-328.
22. Mattson M P (2007) Calcium and neurodegeneration. Aging Cell 6: 337-350
23. Lee C H, Yan B, Yo K Y, Choi J H, Kwon S H, Her S, Hwang I K, Cho J H, Kim Y M, Won M H (2011) Ischemia-induced changes in glucagon-like peptide-1 receptor and neuroprotective effect of its agonist exendin-4, in experimental transient cerebral ischemia. J Neurosc Res 89: 1103-1113.
24. Teramoto S, Miyamoto N, Yatomi K, Tanaka Y, Oishi H, Arai H, Hattori N, Urabe T (2011) Exendin-4, a glucagon-like peptide-1 receptor agonist, provides neuroprotection in mice transient focal cerebral ischemia. J Cerebr Blood Flow Metab 31:8, 1696-1705.
25. Nakagawa A, Satake H, Nakabayashi H (2004) Receptor gene expression of glucagon-like peptide-1, but not of glucose-dependent insulinotropic polypeptide, in rat nodose ganglion cells. Auton Neurosci 110: 36-43.
26. Perry T A, Holloway H, Weerasuriya A, Mouton P R, Duffy K, Mattison J A, Greig N H (2007) Evidence of GLP-1-mediated neuroprotection in an animal model of pyridoxine-induced peripheral sensory neuropathy. Exp Neurol 203: 2, 293-301.
27. During M H, Cao L, Zuzga D S, Francis J S, Fitzsimons H L, Jiao X, Bland R J, Klugmann M, Banks W A, Drucker D J, Haile C N (2003) Glucagon-like peptide-1 receptor is involved in learning and neuroprotection. Nat Med 9: 1173-1179.
28. Isacson R, Nielsen E, Dannaeus K, Bertilsson G, Patrine C, Zachrisson O, Wikström L (2009) The glucagon-like peptide 1 receptor agonist exendin-4 improves reference memory performance and decreases immobility in the forced swim test. Eur J Pharmacol 10: 650, 249-55.
29. Himeno T, Kamiya H, Naruse K, Harada N, Ozaki N, Seino Y, Shibata T, Kondo M, Kato J, Okawa T, Fukami A, Hamada Y, Inagaki N, Drucker D J, Oiso Y, Nakamura J (2011) Beneficial effects of exendin-4 on experimental polyneuropathy in diabetic mice. Diabetes 60:2397-2406.
30. Porter D W, Kerr B D, Flatt P R, Hölscher C, Gault V A (2010) Four weeks administration of Liraglutide improves memory and learning as well as glycemic control in mice with high fat dietary-induced obesity and insulin resistance. Diab Obes Metab 12: 891-899, 2010.
31. Doyle M E, Egan J M., Mechanisms of action of glucagon-like peptide 1 in the pancreas. Pharmacol Ther. 2007 March; 113β):546-93. Epub 2006 Dec. 28.
32. Hoist (1999), Curr. Med. Chem. 6: 1005
33. Nauck et al. (1997) Exp Clin Endocrinol Diabetes 105: 187
34. Lopez-Delgado et al. (1998) Endocrinology 139:2811.
35. McClean P L, Gault V A, Harriott P, Hölscher C, 2010, Glucagon-like peptide-1 analogues enhance synaptic plasticity in the brain: A link between diabetes and Alzheimer's disease, *European Journal of Pharmacology,* 630, 158-162.
36. Kastin A J, Akerstrom V, Pan W, 2001, Interactions of Glucagon-like peptide (GLP-1) with blood brain barrier, *Journal of Molecular Neuroscience,* 18(2), 7-14.
37. Perry T and Greig N, 2003, The glucagon-like peptides: a double-edged therapeutic sword? *Trends in Pharmacological Sciences,* 24, 377-383.
38. Li H, Lee C H, Yoo K Y, Choi J H, Park O K, Yan B C. Byun K, Lee B, Hwang J K, Won M H (2010) Chronic treatment of exendin-4 affects cell proliferation and neuroblast differentiation in the adult mouse hippocampal dentate gyrus. Neurosci Lett 19: 1205-1219.
39. Hamilton A., S. Patterson, D. Porter, V. A. Gault and C. Hölscher (2011): Novel GLP-1 mimetics developed to treat type 2 diabetes promote progenitor cell proliferation in the brain. J Neurosci Res, 89:481-489.
40. Gengler S, McClean P, McCurtin R, Gault V, Hölscher C (2012) Val(8)GLP-1 rescues synaptic plasticity and reduces dense core plaques in APP/P S1 mice. Neurobiol Aging 33:265-276.
41. Sherer, T. B. Kim, J.-H, Betarbet, R. and Greenamyre, J. T., Subcutaneous Rotenone Exposure Causes Highly Selective Dopaminergic Degeneration and α-Synuclein Aggregation, 2003, *Experimental Neurology*, 179: 9-16.

42. Lotharius, J., Barg, S., Wiekop, P., Lundberg, C., Raymon, H. K., and Brundin, P., Effect of Mutant α-Synuclein on Dopamine Homeostasis in a New Human Mesencephalic Cell Line, 2002, *Journal of Biological Chemistry*, 277: 38884-38894.

43. Lotharius, J., Falsig, J., van Beek, J., Payne, S., Dringen, R., Brundin, P., and Leist, M., Progressive Degeneration of Human Mesencephalic Neuron-Derived Cells Triggered by Dopamine-Dependent Oxidative Stress Is Dependent on the Mixed-Lineage Kinase Pathway, 2005, *Journal of Neuroscience*, 25: 6329-6342.

44. Tanner, C. M., Kamel, F., Ross, G. W. Hoppin, J. A., Goldman, S. M., Korell, M., Marras, C., Bhudhikanok, G. S., Kasten, M., Chade, A. R. Comyns, K., Richards, M. B., Meng, C., Priestley, B., Fernandez, H. H., Cambi, F., Umbach, D. M., Blair, A., Sandier, D. P., and Langston, J. W., Rotenone, Paraquat, and Parkinson's Disease, 2011, *Environmental Health Perspectives*, 119: 866-872.

45. Kim, S., Moon, M. and Park, S., Exendin-4 protects dopaminergic neurons by inhibition of microglial activation and matrix metalloproteinase-3 expression in an animal model of Parkinson's disease, 2009, *J. Endocrinology*, 202: 431-439.

46. Dubois B. et al. Revising the definition of Alzheimer's disease: a new lexicon. *Lancet Neurol.* 2010; 9: 1118-27.

The invention claimed is:

1. A method for treating Alzheimer's disease in a patient in need thereof, comprising administering to said patient a therapeutically effective amount of a pharmaceutical composition comprising desPro$^{36}$-Exendin-4(1-39)Lys$_6$-NH$_2$ or a pharmaceutically acceptable salt thereof, and optionally a pharmaceutically acceptable carrier, adjuvant, auxiliary substance, or a combination thereof.

2. The method of claim 1, wherein the progression of the Alzheimer's disease is slowed down.

3. The method according to claim 1, wherein the Alzheimer's disease is an early-stage Alzheimer's disease.

4. The method of claim 1, comprising administering desPro$^{36}$Exendin-4(1-39)-Lys$_6$-NH$_2$ or the pharmaceutically acceptable salt thereof in a daily dose selected from the range of 10 μg to 20 μg.

* * * * *

SEQUENCE LISTING

```
<160> NUMBER OF SEQ ID NOS: 5

<210> SEQ ID NO 1
<211> LENGTH: 44
<212> TYPE: PRT
<213> ORGANISM: Artificial
<220> FEATURE:
<223> OTHER INFORMATION: desPro36-Exendin-4(1-39)-Lys6-NH2

<400> SEQUENCE: 1

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Ser Lys Lys Lys Lys Lys Lys
        35                  40

<210> SEQ ID NO 2
<211> LENGTH: 39
<212> TYPE: PRT
<213> ORGANISM: Heloderma suspectum

<400> SEQUENCE: 2

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 3
<211> LENGTH: 30
<212> TYPE: PRT
<213> ORGANISM: artificial
<220> FEATURE:
<223> OTHER INFORMATION: GLP-1(7-36)

<400> SEQUENCE: 3

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg
            20                  25                  30

<210> SEQ ID NO 4
<211> LENGTH: 20
<212> TYPE: DNA
<213> ORGANISM: artificial
<220> FEATURE:
<223> OTHER INFORMATION: forward primer
```

```
<400> SEQUENCE: 4
gaattccgac atgactcagg                                        20

<210> SEQ ID NO 5
<211> LENGTH: 20
<212> TYPE: DNA
<213> ORGANISM: artificial
<220> FEATURE:
<223> OTHER INFORMATION: reverse primer

<400> SEQUENCE: 5
gttctgctgc atcttggaca                                        20
```